US005565352A

United States Patent [19]
Hochstrasser et al.

[11] Patent Number: 5,565,352
[45] Date of Patent: Oct. 15, 1996

[54] DEUBIQUITINATING ENZYME: COMPOSITIONS AND METHODS

[75] Inventors: Mark Hochstrasser; Feroz Papa, both of Chicago, Ill.

[73] Assignee: Arch Development Corporation, Chicago, Ill.

[21] Appl. No.: 159,340

[22] Filed: Nov. 24, 1993

[51] Int. Cl.$^6$ ............................. C12N 15/53; C12N 1/19; C12N 1/18; C12N 1/16; C12N 1/21; C12N 5/10; C12N 15/63

[52] U.S. Cl. ..................... 435/240.1; 435/252.3; 435/201; 435/254.11; 435/254.2; 435/254.21; 435/255.2; 435/255.1; 435/320.1; 435/172.3; 536/23.2; 935/69; 935/10; 935/14

[58] Field of Search ........................... 435/320.1, 252.3, 435/252.33, 254.2, 254.21, 255.2, 255.1, 69.1, 240.1, 201; 536/23.2

[56] References Cited

U.S. PATENT DOCUMENTS

| | | | |
|---|---|---|---|
| 5,093,242 | 3/1992 | Bachmair | 435/69.7 |
| 5,122,463 | 6/1992 | Varshavsky et al. | 435/172.3 |
| 5,132,213 | 7/1992 | Bachmair et al. | 435/69.7 |
| 5,196,321 | 3/1993 | Bachmair et al. | 435/69.7 |
| 5,212,058 | 5/1993 | Baker et al. | 435/252.33 |

OTHER PUBLICATIONS

Geubank/EMBL database accession #L08070 (1992).
Latterich et al (1991) Molecular Microbiology 5:2417–2426.
Wilkinson et al. 1989 Science 246:670–673.
Watson et al (1993) J. Cellular Biochem. 17C:43.
Glover (1984) Gene Cloning New York: Chapman and Hall pp. 110–127.
Bachmair et al., "In Vivo Half–Life of a Protein Is a Function of Its Amino–Terminal Residue," *Science*, 234:179–186, 1986.
Baker et al., "Ubiquitin–specific Proteases of *Saccharomyces cerevisiae*," *The Journal of Biological Chemistry*, 267(32):23364–23375, 1992.
Eytan et al., "Ubiquitin C–terminal Hydrolase Activity Associated with the 26 S Protease Complex," *Journal of Biological Chemistry*, 268(7):4668–4674, 1993.
Glotzer et al., "Cyclin is degraded by the ubiquitin pathway," *Nature*, 349:132–138, 1991.
Gupta et al., "Unp, a mouse gene related to the tre oncogene," *Oncogenic*, 8:2307–2310, 1993.
Hadari et al., "A Ubiquitin C–terminal Isopeptidase That Acts on Polyubiquitin Chains," *The Journal of Biological Chemistry*, 267(2):719–727, 1992.

Hochstrasser, "Ubiquitin and intracellular protein degradation," *Current Opinion in Cell Biology*, 4:1024–1031, 1992.
Hochstrasser and Varshavsky, "In Vivo Degradation of a Transcriptional Regulator: The Yeast α2 Repressor," *Cell*, 61:697–708, 1990.
Holloway et al., "Anaphase Is Initiated by Proteolysis Rather Than by the Inactivation of Maturation–Promoting Factor," *Cell*, 73:1393–1402, 1993.
Jentsch, "The Ubiquitin–Conjugation System," *Annu. Rev. Genet.*, 26:179–207, 1992.
Mayer and Wilkinson, "Detection, Resolution, and Nomenclature of Multiple Ubiquitin Carboxyl–Terminal Esterases from Bovine Calf Thymus," *Biochemistry*, 28:166–172, 1989.
Miller et al., "Cloning and Expression of a Yeast Ubiquitin–Protein Cleaving Activity in *Escherichia Coli*," *Bio/Technology*, 7:698–709, 1989.
Miller et al., "*c–fos* Protein Can Induce Cellular Transformation: A Novel Mechanism of Activation of a Cellular Oncogene," *Cell*, 36:51–60, 1984.
Nakamura et al., "A novel transcriptional unit of the tre oncogene widely expressed in human cancer cells," *Oncogene*, 7:733–741, 1992.
Okazaki et al., "Differential occurrence of CSF–like activity and transforming activity of Mos during the cell cycle in fibroblasts," The EMBO Journal, 11(7):2447–2456, 1992.
Scheffner et al., "The E6 Oncoprotein Encoded by Human Papillomavirus Types 16 and 18 Promotes the Degradation of p53," *Cell*, 63:1129–1136, 1990.
Tobias and Varshavsky, "Cloning and Functional Analysis of the Ubiquitin–specific Protease Gene *UBP1* of *Saccharomyces cerevisiae*," *The Journal of Biological Chemistry*, 18:12021–12028, 1991.

*Primary Examiner*—Robert A. Wax
*Assistant Examiner*—G. E. Bugaisky
*Attorney, Agent, or Firm*—Arnold, White & Durkee

[57] ABSTRACT

The invention relates generally to compositions of and methods for obtaining deubiquitinating enzyme polypeptides. The invention relates as well to polynucleotides encoding deubiquitinating enzyme polypeptides, the recombinant vectors carrying those sequences, the recombinant host cells including either the sequences or vectors, and recombinant deubiquitinating enzyme polypeptides. By way of example, the invention discloses the cloning and functional expression if at least three different deubiquitinating enzyme polypeptides. The invention includes as well, methods for using the isolated, recombinant enzyme polypeptides in assays designed to select and improve substances capable of interacting with deubiquitinating enzyme polypeptides for use in diagnostic, drug design and therapeutic applications.

7 Claims, 27 Drawing Sheets

```
-270  TATCTATATAAGTGCAAAACTATATAACCATTATTTATTTGCTTTCC
-180  CGAATGGCTAAGCCCTTGGTAGTATTAGTAAAGCCTAGAAAAAAAA
 -90  ATGTATTTATCTTCGGTAGTATAGGGCAGATTAAGACTGAGTGT
   1  ATGGAGCAGAATATTAGTACTACCATAAGGATGAGTGTATTCGT
      M  E  Q  N  I  I  S  T  I  R  D  E  C  I  R    15
  91  GAGGCTAAAATTAACGAATTCATCATAACTGGTAAGGCAAAAGAT
      E  A  K  I  N  E  F  I  I  T  G  K  A  K  D    45
 181  ATTTACAAGAAGAACTCGAAATCAAAAATATTATATCGTGC
      I  Y  K  K  N  S  K  D  I  K  N  I  I  S  C    75
 271  CAATTAAAATTATGTTTACTACAAGTAATTCACATTATTGTAACA
      Q  L  N  Y  V  Y  Y  K  V  I  H  I  I  V  T   105
 361  AAGAGCACGAGTGATGAGGGCAACGGTAATAACAACAATAATGAA
      K  S  T  S  D  E  G  N  G  N  N  N  N  N  E   135
 451  AAAGATGAAAACATTGCAAAATAAAAGTTTCATTAAGTCTTCC
      K  D  E  N  I  A  K  I  K  S  F  I  K  S  S   165
 541  ATGAGAACGGGTTCCTATATCGATCAAGTTGGAATTCAACAAGTCACATATT
      M  R  T  G  S  Y  I  T  S  N  Q  L  N  S  L   195
 631  CTGATAGATATCAGATCATGATTTGGAGAAAAATCATTAATTACTTCT
      L  I  D  I  R  S  R  L  E  F  N  K  S  H  I   225
 721  TCATATTCAGATCATGATTTGGAGAAAAATCATTAATTACTTCT
      S  Y  S  D  H  D  L  E  K  K  S  L  I  T  S   255
 811  TTTATCATTCTCTATACAGACGCAAACGAATACAATGTTAAACAG
      F  I  I  L  Y  T  D  A  N  E  Y  N  V  K  Q   285
 901  CCAATATCCGATGACTTTACCAAAATTTCATTCTGGAATCTGGT
      P  I  S  D  D  F  T  K  I  F  I  L  E  S  G   315
 991  TCTTTTCCATCAAATAACATTCAATGATGATAGTGTTTATATT
      S  F  P  S  N  N  N  I  K  D  D  S  V  Y  I   345
1081  TCTCCCAGTATAAGACATTCAATGGACGACTCTATGAAAGAAATG
      S  P  S  I  R  H  S  M  D  D  S  M  K  E  M   375
```

FIG 1B

```
      ACATTGTTTACTTCATTGCTTCAATATCGTTCATTACGTTTAG       30
      AAAAAAAAAAAAAAGGATATGATGTTATATGATACGTGTAGTTC       60
      GCACGCTTCCAAAGTTTTTTACTATTTGATACATGCTTAAGTT
      CACCGGTCGAAGTACCTTACGATAGCACAACTAACCGCTATTGCA       90
 16   H   R   S   K   Y   L   T   I   A   Q   L   T   A   I   A
      CAAGATTTGAGCAGTCTTCTAGATAAATGCATCGATATTTTATCT      120
 46   Q   D   L   S   S   L   L   D   K   C   I   D   I   L   S
      AAAAATAAGGGTGCAATGATTAGTTCAAATTCCGTAATGATTATT      150
 76   K   N   K   G   A   M   I   S   S   N   S   V   M   I   I
      ACCAATATTCCTCATTTAAGTGAATTCGCCAAGATTAAATTACAT      180
106   T   N   I   P   H   L   S   E   F   A   K   I   K   L   H
      TTTCAACTCATGAACATTTACAACTTTGCTGGAAACCTTATTA       210
136   F   Q   L   M   N   I   Y   N   T   L   L   E   T   L   L
      ATAAAACAAACAAAATTGAACCATGAGCAAGAAGAATGTAACCTG      240
166   I   K   Q   T   K   L   N   H   E   Q   E   E   C   N   L
      ATAAGTTCATCAGCAAATTCTGCTTCCTCCCAAATGGAGATACTA      270
196   I   S   S   A   N   S   A   S   S   Q   M   E   I   L
      GATACAAAAAATATTATATGCCCTGGAGCCTATTTCTTTTAAAATG     300
226   D   T   K   N   I   I   C   L   E   P   I   S   F   K   M
      CCTAATAGTGAGATTAAAATGTTTCAAAGTAGAAATCTTTTCAAG      330
256   P   N   S   E   I   K   M   F   Q   S   R   N   L   F   K
      CAGTCTCTGTCCTGTTGGACATTCTGGTGAATCATTCCTTTGAAAAA    360
286   Q   S   V   L   D   I   L   V   N   H   S   F   E   K
      TTTCCAGGTTGGCTTAAGTCAAATTATGGGAGGCAAGTATCATCA      390
316   F   P   G   W   L   K   S   N   Y   G   R   Q   V   S   S
      AATGGTAACACTTCTGGCCTAAGTTTACAACATTTACCTAAGATG
346   N   G   N   T   S   G   L   S   L   Q   H   L   P   K   M
      CTAGTTGCGCCTACTCCATTAAATCATCTTCAACAACAGCAACAA
376   L   V   A   P   T   P   L   N   H   L   Q   Q   Q   Q   Q
```

FIG 1C

```
1171  CAGCAATCAGACAATGATCATGTGCTAAAAAGATCTTCAAGTTTC  405
      Q  Q  S  D  N  D  H  V  L  K  R  S  S  S  F
1261  AATTCAAACTTATATTCTATATCTTCGTTGTCCATATCTAGTTCA  435
      N  S  N  L  Y  S  I  S  S  L  S  I  S  S  S
1351  TCATTGCCAATCAATTATCCGGAAACGCCACATCTTTGGAAAAAC  465
      S  L  P  I  N  Y  P  E  T  P  H  L  W  K  N
1441  AACTCTTTTGCTCACATAGCTCCTATCAACGAAGGCCATCACT    495
      N  S  F  A  H  I  A  P  I  N  T  K  A  I  T
1531  ACAATTAGTATGAACTTAATATGAACTCCAATGGACACAGTTCT   525
      T  I  S  M  N  L  N  M  N  S  N  G  H  S  S
1621  GACTCTTTAGATCATACAGATGTTACACCAACTTCTTCTCATAAT  555
      D  S  L  D  H  T  D  V  T  P  T  S  S  H  N
1711  TGTTACATGAACTGTATCATTCAGTGTATCTTAGGTACACACGAA  585
      (C) Y  M  N  C  I  I  Q  C  I  L  G  T  H  E
1801  ATTAATAGTAAGTTGGGATCGAAGGTATTCTGGCAAAATATTTT   615
      I  N  S  K  L  G  S  K  G  I  L  A  K  Y  F
1891  AAGAAAATTCCATATCACCGATAAAATTTAAATTGGCATGTGGA   645
      K  K  I  S  I  S  P  I  K  F  K  L  A  C  G
1981  GAGTTTTGCCAATTCCTTCCTTCTAGATGGTCTTCATGAAGACTTGAAC  675
      E  F  C  Q  F  L  L  D  G  L  H  E  D  L  N
2071  GAGGCGAGAGAAAAACTGTCTTTGGAATTGCCTCGTCAATT      705
      E  A  R  E  K  L  S  L  R  I  A  S  S  I
2161  TTATTTCAGGGACAATACGCCTCACGACTAAAATGTAAAGTCTGT  735
      L  F  Q  Q  Y  A  S  R  L  K  C  K  V  C
2251  CCTATTCCTAAAAAAAATTCCCGAAATATTACCATTGAAGAT    765
      P  I  P  K  K  N  S  R  N  N  I  T  I  E  D
2341  CAATGGTTGTGCCCACATTGTGAAAAAGGCAGCCCTCCACGAAA  795
      Q  W  L  C  P  H  C  E  K  R  Q  P  S  T  K
2431  AAGAGATTTGATAATTTATTAAACAAAAATAATGACTTCGTCATA
```

FIG 1D

```
         AAAAATTATTCTCAAATTATACGTCTCCTAATCCGAAGAATTCA
         K  K  L  F  S  N  Y  T  S  P  N  P  K  N  S             420
         CCATCGCCTTTACCTCTACATTCGCCTGACCCAGTTAAGGCAAT
406      P  S  P  L  P  L  H  S  P  D  P  V  K  G  N             450
         AGTGAGACAGATTTATGACAAATCAAAGAGAACAGTTGAATCAC
436      S  E  T  D  F  M  T  N  Q  R  E  Q  L  N  H             480
         TCTCCATCAAGAACTGCCACCGAAGTTACAACGCTTCCCGCAA
466      S  P  S  R  T  A  T  P  K  L  Q  R  F  P  Q             510
         GCCACCTCTACCATTCAACCTTCGTGTCTTGGTTTGGAAAATCTAGGAAATTCG
496      A  T  S  T  I  Q  P  S  C  L  S  L  S  N  N             540
         TATGACCTTGATTTCGCGGTTGGTTTGGAAATCTAGGAAATTCG
526      Y  D  L  D  F  A  V  G  L  E  N  L  G  N  S             570
         TTAACCCAAATCTTTTTGGACGATTCATATGCTAAACACATCAAT
556      L  T  Q  I  F  L  D  D  S  Y  A  K  H  I  N             600
         GCAAGGTTGGTTCATATGATGTATAAGGAACAGGTTGATGGTTCA
586      A  R  L  V  H  M  M  Y  K  E  Q  V  D  G  S             630
         TCTGTTAACTCATTATTTAAGACTGCATCCCAACAGGACTGCCAA
616      S  V  N  S  L  F  K  T  A  S  Q  Q  D  C  Q             660
         CAATGCGGTTCAAACCCACCTTTGAAGGAGCTTTCTCAAGAAGCT
646      Q  C  G  S  N  P  P  L  K  E  L  S  Q  E  A             690
         GAGTGGGAACGATTCTTGACTACTGATTTCAGTGTTATTGTCGAG
676      E  W  E  R  F  L  T  T  D  F  S  V  I  V  D             720
         AGTCATACCTCGACAACATACCAACCTTTTACGGTGCTGTCAATC
706      S  H  T  S  T  T  Y  Q  P  F  T  V  L  S  I             750
         TGTTTCAGAGAGTTCACCAAATGTGAGAACTTGGAAGTGGATGAG
736      C  F  R  E  F  T  K  C  E  N  L  E  V  D  E             780
         CAATTGACACAATAACGAGATTACCGAGGAATCTGATAGTCCATTTA
766      Q  L  T  I  T  R  L  P  R  N  L  I  V  H  L             810
         TACCCTTTTTTGTTGGACTTGACTTCCATTTGGGCCAATGATTTT
796
```

FIG 1E

```
        K   R   F   D   N   L   L   N   K   N   N   D   F   V   I    825
2521 GACGGGGTTTTCCTCCAGGTGTTAATGACGATGAACTACCAATA
        D   G   V   F   P   P   G   V   N   D   D   E   L   P   I    855
2611 TGCCACTTTGGTACTTTGTATGGTGGTCATTATACAGCCTATGTG
        C   H   F   G   T   L   Y   G   G   H   Y   T   A   Y   V    885
2701 TATAAACCTGTCAAAAACAAAGCCGATGCAATTAACTCTAATGCA
        Y   K   P   V   K   N   K   A   D   A   I   N   S   N   A    915
2791 ATAAATAACTGAAAACCGTTGTCTATACACTTTTTTCCCGTTCA
2881 TAAATACAAATGATTTATTTTAACGGTAACAAACGAACTTTTTT
2971 TGTGCATCTCTTGGATTGATGATTTTCCTTTCTACCATAATACGT
```

FIG 1F

```
826  Y  P  F  L  L  D  L  T  P  F  W  A  N  D  F
     AGGGGACAAATACCACCTTTTAAGTATGAATTATATGGTGTAGCA        840
866  R  G  Q  I  P  P  F  K  Y  E  L  Y  G  V  A
     AAAAAGGGATTAAAGAAGGGATGGCTATATTTTGATGATACCAAA        870
886  K  K  G  L  K  K  G  W  L  Y  F  D  D  T  K
     TACGTTTTGTTTTATCACCGGTCTACGGTGTTTGATTCATTTGA         900
916  Y  V  L  F  Y  H  R  V  Y  G  V  *
     ACATGGCATATCATTATTTCCATCTAAGGTCAAAGTAAAAAACCC        926
     TAGAAGGTGTAAAGATGAGATCACGCCCAGATTTGTCTTCCTCC
     CATGAAAAGTATGTAAATATTTATAGCATTACATATATCTTTTAT
```

FIG 1G

Block 1

```
561 AVGLENLGNSCYMNCIIQCILGTHELTQIFLDDSYAKHININSKLGSKGIL 611
    |.||.||||.|.||.  .|..  .|:.  ..|::..|  ...:||  |||
214 ATGLSNLGNTCFMNSSIQCVSNTQPLTQYFISGRHLYELNRTNPIGMKGHM 264

651 FKTASQQDCQEFCQFLLDGLHEDLNQCGSNPPLKELSQEAEARREKLSLRI 701
    |..  |||:||: .||||||||||||  .||  :  :  :: :|  |
299 FDGFQQQDSQELLAFLLDGLHEDLNRVHEKPYVELKDSDGRPDWE...... 343

741 TYQPFFTVLSIPIP 753      761 ITIEDCFREFTKCEN 775
    ::  ||:.||:|:|              |:..:.||.||.|:.|
383 RFDPFNFLSLPLP  395      714 INLDSCLRAFTSEEE 728
```

FIG 2C-1

```
        ||::: ||:: ::    |:::|:::|::  ...  ...  ..
612     AKYFARLVHMMYKEQVDGSKKISISPIKFKLACGSVNSL   650
        ||:::||:::   :   |::::|:|::  .|.::|::..|::.|:.
265     AKCYGDLVQELW......SGTQKSVAPLKLRRTIAKYAPK   298

...  .|::  .   :  |:::|:|::  ..|:|:||.  ..|:|.|:.
702     ASSIEWERFLTTDFSVIVDLFQGQYASRLKCKVCSHTST   740
         ..:..|::|:::|:|:|:||::|||:||::|:|:||:|:|::
344     VAAEAWDNHLRRNRSIIVDLFHGQLRSQVKCKTCGHISV   382

Block 2

|:: .|..|.|..  .|::  |||  ||::|  |||||
776     LEVDEQWLCPHCEKRQPSTKQLTITRLPRNLIVHLKRFD   814
         |:.|..|:|:::|:|.|:||.|.|:|:|||:||:|||:|
729     LGESEMYYCSKCKTHCLATKKLDLWRLPPFLIHLKRFQ   767
```

FIG 2C-2

His Domain

| | | | | | | |
|---|---|---|---|---|---|---|
| Ubp1 | 681 | YSLRSVIVHYGTHN.YGHYIAFR...KYR..GC..WWRISDETVYVDEAEVLS........ | TPGVFMLFY | 735 |
| Ubp2 | 1185 | YSLFSVFIHRGEAS.YGHYWIYI..KDR.NRNGIWRKYNDETISEVQFEEVFNFNEGN.. | TATHYFLVY | 1247 |
| Unp | 696 | YDLIAVSNHYGAMG.VGHYTAYA..KNRLNGK..WYYFDDSSVSLASEDQIV........ | TKAAYVLFY | 751 |
| tre-2 | 995 | YNLYAISCHSGILS.GGHYITYA..KNP.NCK..WYCYNDSSCEELHFDEID........ | TDSAYILFY | 1049 |
| Doa4 | 864 | YELYGVACHFGTLY.GGHYTAYV..KK..GLKKGWLYFDDTKYKPVKNKADAI....... | NSNAYVLFY | 920 |
| Faf | 1969 | YELTGIVVHSGQAS.GGHYFSYILSKNPANGKCQWYKFDDGEVTECKMHEDEEMKAECFGGENAYMLFY | | 2058 |
| Ubp3 | 844 | YKLTGVIYHHGVSSDGGHYTADVY.HSEHN.K..WYRIDDVNITELEDDVLKGGEEASDSRTAYIIMY | | 908 |
| Cons | | Y-L-nV--H-G---S-GGHY-AY---K---N-K--WY-hDD--h-E----E-------T--AYhLFY | | |

FIG. 2E

|  | MHY102 | MH11D5-8a | MHY501 | MHY623 | MHY105 | MHY490 |
|---|---|---|---|---|---|---|
| Doubling time (h) | 1.7 | 2.4 | nd | nd | nd | nd |
| Heat stress (38.5°C) | +++ | +/- | +++ | +/- | nd | nd |
| 100 μM Cd²⁺ | ++ | +/- | ++ | +/- | nd | nd |
| Canavanine (% control) | 92 | <0.2 | 99 | <0.2 | nd | nd |
| uv or γ-irradiation | +++ | + | +++ | + | nd | nd |
| Sporulation (%) |  |  |  |  | 40-50 | <0.001 |

FIG. 4C

DEUBIQUITINATING ENZYME: COMPOSITIONS AND METHODS

The U.S. Government may own rights in the present invention pursuant to NIH Grant No. GM46904.

FIELD OF THE INVENTION

This invention relates generally to compositions of and methods for obtaining and using deubiquitinating enzymes. The invention relates as well to the DNA sequences encoding those enzymes, recombinant vectors carrying those sequences, recombinant host cells including either the sequences or vectors, and recombinant deubiquitinating enzyme polypeptides. The invention includes as well methods for using the isolated, recombinant deubiquitinating enzyme polypeptides in assays designed to select and improve among candidate substances for use in diagnostic, drug design and therapeutic applications.

BACKGROUND OF THE INVENTION

For many short-lived eukaryotic proteins, covalent attachment to the polypeptide ubiquitin is a prerequisite for their degradation; examples include the destruction of cyclins in cell cycle control (Glotzer et al., 1991) and degradation of proteins that regulate development, e.g., the vertebrate c-mos protein kinase (Okazaki et al., 1992) or the yeast MATα2 transcription factor (Hochstrasser et al., 1991; Chen et al., 1993). The ubiquitin system is essential for phenomena as diverse as the heat shock response and DNA repair, and both ubiquitin and the enzymes involved in ubiquitin metabolism are highly conserved among eukaryotic phyla (Finley and Chau, 1991; Hershko and Ciechanover, 1992; Hockstrasser et al., 1992; Jentsch, 1992; Varshavsky, 1992). Using a MATα2 derivative as substrate, a ubiquitin-dependent degradation pathway in the yeast *Saccharomyces cerevisiae*, the DOA (degradation of alpha) pathway has recently been identified (Chen et al., 1993; Hochstrasser & Varshavsky, 1990). This pathway, which requires two ubiquitin-conjugating (Ubc) enzymes, Ubc6 (Doa2) and Ubc7, targets α2 via an element within the first 67 residues of the α2 repressor, the Deg1 degradation signal. Many more gene products have been implicated in α2 degradation, based on genetic analyses (Chen et al., 1993).

Deubiquitinating enzymes serve a number of functions (Hochstrasser, 1992; Rose, 1988). First, ubiquitin must be cleaved from a set of biosynthetic precursors, which occur either as a series of ubiquitin monomers in head-to-tail linkage or as fusions to certain ribosomal proteins (Finley & Chau, 1991). Secondly, ubiquitin must be recycled from intracellular conjugates, both to maintain adequate pools of free ubiquitin and, in principle at least, to reverse the modification of inappropriately targeted proteins. Finally, deubiquitinating reactions may be integral to the degradation of ubiquitinated proteins by the 26S proteasome, a complex ATP-dependent enzyme whose exact composition and range of activities remain poorly characterized (Hershko & Ciechanover, 1992; Hardari et al., 1992; Murakami, 1992; Rechsteiner, 1993).

Consistent with these diverse functions, eukaryotic cells have been shown to contain many distinct deubiquitinating enzymes (Rose, 1988; May & Wilkinson, 1989; Jonnalagadda, 1989; Baker et al., 1992). Previously, four deubiquitinating enzyme genes, YUH1, UBP1, UBP2, and UBP3, had been identified in *S. cerevisiae* (Baker et al., 1992; Miller, 1989; Tobias & Varshavsky, 1992). A mutant strain lacking all four genes grows normally and shows continued high deubiquitinating activity (Baker et al., 1992).

BRIEF SUMMARY OF THE INVENTION

In one aspect, the present invention provides an isolated and purified polynucleotide that encodes a deubiquitinating enzyme polypeptide. In a preferred embodiment, a polynucleotide of the present invention is a DNA molecule. More preferably, a polynucleotide of the present invention encodes a polypeptide comprising the amino acid residue sequence of DOA4 (SEQ ID NO: 2). Most preferably, an isolated and purified polynucleotide of the invention comprises the nucleotide base sequence of SEQ ID NO: 1 from about nucleotide position 271 to about nucleotide position 3048 or SEQ ID NO: 1.

Yet another aspect of the present invention contemplates an isolated and purified polynucleotide comprising a base sequence that is identical or complementary to a segment of at least 10 contiguous bases of SEQ ID NO: 1, wherein the polynucleotide hybridizes to a polynucleotide that encodes an deubiquitinating enzyme polypeptide. Preferably, the isolated and purified polynucleotide comprises a base sequence that is identical or complementary to a segment of at least 25 to 70 contiguous bases of SEQ ID NO: 1 from about nucleotide position 271 to about nucleotide position 3048 or SEQ ID NO: 1. For example, the polynucleotide of the invention can comprise a segment of bases identical or complementary to 40 or 55 contiguous bases of the disclosed nucleotide sequences.

In still another embodiment of the present invention, there is provided an isolated and purified polynucleotide comprising a base sequence that is identical or complementary to a segment of at least 10 contiguous bases of SEQ ID NO: 1 from about nucleotide position 271 to about nucleotide position 3048 or SEQ ID NO: 1. The polynucleotide of the invention hybridizes to SEQ ID NO: 1 from about nucleotide position 271 to about nucleotide position 3048 or SEQ ID NO: 1, or a complement of SEQ ID NO: 1 from about nucleotide position 271 to about nucleotide position 3048 or SEQ ID NO: 1. Preferably, the isolated and purified polynucleotide comprises a base sequence that is identical or complementary to a segment of at least 25 to 70 contiguous bases of SEQ ID NO: 1 from about nucleotide position 271 to about nucleotide position 3048 or SEQ ID NO: 1. For example, the polynucleotide of the invention can comprise a segment of bases identical or complementary to 40 or 55 contiguous bases of SEQ ID NO: 1 from about nucleotide position 271 to about nucleotide position 3048 or SEQ ID NO: 1.

In another embodiment, the present invention contemplates an isolated and purified deubiquitinating enzyme polypeptide. Preferably, an deubiquitinating enzyme polypeptide of the invention is a recombinant polypeptide. More preferably, an deubiquitinating enzyme polypeptide of the present invention is a yeast deubiquitinating enzyme polypeptide. Even more preferably, an deubiquitinating enzyme polypeptide of the present invention comprises the amino acid residue sequence of DOA4 (SEQ ID NO: 2).

In an alternative embodiment, the present invention provides an expression vector comprising a polynucleotide that encodes an deubiquitinating enzyme polypeptide. Preferably, an expression vector of the present invention comprises a polynucleotide that encodes a polypeptide comprising the amino acid residue sequence of SEQ ID NO: 2. More preferably, an expression vector of the present invention comprises a polynucleotide comprising the nucleotide base sequence of SEQ ID NO: 1 from about nucleotide position 271 to about nucleotide position 3048 or SEQ ID NO: 1. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes an deubiquitinating enzyme polypeptide. Preferably, a recombinant host cell of the present invention is transfected with the polynucleotide of SEQ ID NO: 1 from about nucleotide position 271 to about nucleotide position 3048 or SEQ ID NO: 1. Even more preferably, a host cell of the invention is a eukaryotic host cell. Still more preferably, a recombinant host cell of the present invention is a yeast cell.

In another aspect, a recombinant host cell of the present invention is a prokaryotic host cell. Preferably, a recombinant host cell of the invention is a bacterial cell of the DH5α strain of *Escherichia coli*. More preferably, a recombinant host cell comprises a polynucleotide under the transcriptional control of regulatory signals functional in the recombinant host cell, wherein the regulatory signals appropriately control expression of an deubiquitinating enzyme polypeptide in a manner to enable all necessary transcriptional and post-transcriptional modification.

In yet another embodiment, the present invention contemplates a process of preparing an deubiquitinating enzyme polypeptide comprising transfecting a cell with polynucleotide that encodes an deubiquitinating enzyme polypeptide to produce a transformed host cell; and maintaining the transformed host cell under biological conditions sufficient for expression of the polypeptide. The transformed host cell can be a eukaryotic cell. Alternatively, the host cell is a prokaryotic cell. Even more preferably, a polynucleotide transfected into the transformed cell comprises the nucleotide base sequence of SEQ ID NO: 1 from about nucleotide position 271 to about nucleotide position 3048 or SEQ ID NO: 1.

In still another embodiment, the present invention provides an antibody immunoreactive with an deubiquitinating enzyme polypeptide. Preferably, an antibody of the invention is a monoclonal antibody. More preferably, an deubiquitinating enzyme polypeptide comprises the amino acid residue sequence of SEQ ID NO: 2.

In another aspect, the present invention contemplates a process of producing an antibody immunoreactive with an deubiquitinating enzyme polypeptide comprising the steps of (a) transfecting a recombinant host cell with a polynucleotide that encodes an deubiquitinating enzyme polypeptide; (b) culturing the host cell under conditions sufficient for expression of the polypeptide; (c) recovering the polypeptide; and (d) preparing the antibody to the polypeptide. Preferably, the host cell is transfected with the polynucleotide of SEQ ID NO: 1 from about nucleotide position 271 to about nucleotide position 3048 or SEQ ID NO: 1. Even more preferably, the present invention provides an antibody prepared according to the process described above.

Alternatively, the present invention provides a process of detecting an deubiquitinating enzyme polypeptide, wherein the process comprises immunoreacting the polypeptide with an antibody prepared according to the process described above, to form an antibody-polypeptide conjugate, and detecting the conjugate.

In yet another embodiment, the present invention contemplates a process of detecting a messenger RNA transcript that encodes an deubiquitinating enzyme polypeptide, wherein the process comprises (a) hybridizing the messenger RNA transcript with a polynucleotide sequence that encodes the deubiquitinating enzyme polypeptide to form a duplex; and (b) detecting the duplex. Alternatively, the present invention provides a process of detecting a DNA molecule that encodes an deubiquitinating enzyme polypeptide, wherein the process comprises (a) hybridizing DNA molecules with a polynucleotide that encodes an deubiquitinating enzyme polypeptide to form a duplex; and (b) detecting the duplex.

In another aspect, the present invention contemplates a diagnostic assay kit for detecting the presence of an deubiquitinating enzyme polypeptide in a biological sample, where the kit comprises a first container containing a first antibody capable of immunoreacting with an deubiquitinating enzyme polypeptide, with the first antibody present in an amount sufficient to perform at least one assay. Preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label or an enzyme.

In an alternative aspect, the present invention provides a diagnostic assay kit for detecting the presence, in biological samples, of a polynucleotide that encodes an deubiquitinating enzyme polypeptide, the kits comprising a first container that contains a second polynucleotide identical or complementary to a segment of at least 10 contiguous nucleotide bases of SEQ ID NO: 1 from about nucleotide position 271 to about nucleotide position 3048 or SEQ ID NO: 1.

In another embodiment, the present invention contemplates a diagnostic assay kit for detecting the presence, in a biological sample, of an antibody immunoreactive with an deubiquitinating enzyme polypeptide, the kit comprising a first container containing an deubiquitinating enzyme polypeptide that immunoreacts with the antibody, with the polypeptide present in an amount sufficient to perform at least one assay.

In yet another aspect, the present invention contemplates a process of screening substances for their ability to interact with an deubiquitinating enzyme polypeptide comprising the steps of providing an deubiquitinating enzyme polypeptide, and testing the ability of selected substances to interact with the deubiquitinating enzyme polypeptide.

In a preferred embodiment, providing an deubiquitinating enzyme polypeptide is transfecting a host cell with a polynucleotide that encodes an deubiquitinating enzyme polypeptide to form a transformed cell and maintaining the transformed cell under biological conditions sufficient for expression of the deubiquitinating enzyme polypeptide.

BRIEF DESCRIPTION OF THE DRAWINGS

In the drawings, which form a portion of the specification:

FIGS. 1a–1g show the DOA4 gene. FIG. 1a shows the restriction map of a ~11 kb genomic fragment containing DOA4 and identification of DNA subclones that complement the doa4-1 proteolytic defect. +, rescue of the Deg1-bgal degradation defect; –, failure to reverse the defect. Restriction enzyme sites: B, BamHI; Bg, BglII; C, ClaI; H, HinDIII; K, KpnI; P, PstI; R, EcoRV; S, SalI; Sa, Sau3AI. FIG. 1b shows the nucleotide sequence of DOA4 and predicted amino acid sequence of the Doa4 protein. The conserved domains that include a Cys (circled) and two His (boxed) residues (FIG. 2d,e) are bracketed. Upstream of the ORF, two sequences that may play a role in transcription initiation are highlighted, a poly(dA) tract (double underline) (Struhl, 1985) and a potential TATA element (underline) (Singer et al., 1990).

FIGS. 2a–2e show the deubiquitinating enzyme family. FIG. 2a shows DOTPLOTs of Doa4 vs. human tre-2 and yeast Ubp2. Window=30; stringency-16. FIG. 2b shows the open reading frames of the yeast DOA4 and human tre-2 (Nakamura, 1992) genes, the latter predicted from two cDNA clones, which differ by two segments present in the TRE213 clone but absent from TRE210 (boxes in cDNA; indents in TRE210/ORF1). The Cys (stippled) and His (hatched) domains are highlighted. FIG. 2c shows sequence conservation between two long elements in Doa4 and tre-2 (TRE213/ORF2). The more amino-terminal region, Block 1 (39% identity/60% similarity (Dayhoff et al., 1988)), includes the Cys domain (FIG. 2d); the smaller element is called Block 2 (43%/61%). A third region, Block 3, is referred to as the His domain (FIG. 2e). Weaker sequence similarities between various family members was observed in Blocks 1 and 2, e.g., the region corresponding to residues 656–675 of Doa4. The sequences in FIG. 2c are represented by SEQ ID NO: 3 through SEQ ID NO:8. FIG. 2d and 2e show conserved elements in Doa4 and other deubiquitinating enzymes around the presumptive active site Cys and His residues (arrowheads), including consensus sequences ($\geq 4$ identities). Residues are boxed if present in at least three of the proteins or, in the case of small uncharged (n) or hydrophobic (h) residues, share the indicated property in at least six of the proteins. Sequences compared to Doa4 are yeast Ubp1-Ubp3 (Baker et al., 1992; Tobia & Varshavsky, 1991); mouse Unp (Gupta et al., 1993); human tre-2 (TRE213/ORF2)(Nakamaur, 1992); and *Drosophila fat facets* (fail (Fischer-Vize et al., 1992) (a 22-residue segment was deleted after residue 2029 of faf). Sequences were aligned initially with PILEUP. Many partial cDNA sequences in the GenBank database, identified with BLAST (Altschulet at., 1990), also show significant similarity to regions within Blocks 1–3; these include human (T04867, T09031, Z12710, Z15701, Z21167), *Caenorhabditis elegans* (M80041, Z14720, Z14811), *Arabidopsis thaliani* (Z17750, Z25610), and canine (L03387) sequences. The sequences in FIG. 2d are represented by SEQ ID NO: 9 through SEQ ID NO: 16. The sequences in FIG. 2e are represented by SEQ ID NO: 17 through SEQ ID NO: 44.

FIG. 3a shows deubiquitination of ubiquitin-bgal fusion proteins expressed in bacteria. Substrate was Ub-Met-bgal in lanes 1–5, 7–14 and Ub-Leu-bgal in lane 6. Co-expressed plasmids were: 1, YCplac33; 2, pJT60 (UBP1); 3, pDOA4–8; 4, pDOA4–8$^{Ala571}$; 5, pDOA4–8$^{Ser571}$; 6, pDOA4–8; 7, pGEX-KG; 8, pGEX-DOA4; 9, pGEX-DOA4$^{Ala571}$; 10, pGEX-DOA4$^{Ser571}$; 11, pGEX-KG; 12, pGEX-TRE2 10/ORF 1; 13, pGEX-TRE2 13/ORF2; and 14, pGEX-TRE 210/ORF1-TRE213-ORF2. FIG. 3b shows comparable levels of GST-Doa4 and GST-doa4 point routants in bacteria, as measured by anti-GST immunoblot analysis. Cells carried the following plasmids: 1, pGEX-KG; 2, pGEX-DOA4; 3, pGEX-DOA4$^{Ala571}$; and 4, pGEX-DOA4$^{Ser571}$. Asterisk marks a GST-Doa4 fragment. Full-length GST-TRE210/ORF1 and GSTTRE213/ORF2 proteins were both present at lower but detectable levels. FIG. 3c shows liberation of ubiquitin (Ub) from an isopeptide-linked ubiquitin dimer (Ub2) by GST-Doa4 and GST-tre-2 proteins partially purified from *E. coli*. Lanes 1 and 7, untreated Ub2 and ubiquitin, respectively. Protein added: 2, GST; 3, GST-doa4$^{Ser571}$; 4, GST-Doa4; 5, GST-TRE213/ORF2; and 6, GST-TRE210/ORF1. FIG. 3d shows inactivity of doa4$^{Ser571}$ and doa4$^{Ala571}$ in yeast. Deg1-bgal activity was measured in mutant MH11D5–8a cells bearing the following plasmids: YCplac33 (–); pDOA4–8 (C571); pDOA4–8$^{Ala571}$ (A571); pDOA4–8$^{Ser571}$ (S571). Values are the average of $\geq 3$ measurements from 2–3 transformants; error bars indicate standard deviations. The doa4$^{Ser571}$ and doa4$^{Ala571}$ plasmids also fail to correct the doa4 growth and sporulation defects.

FIGS. 4a–4c. FIG. 4a shows structure of the doa4-DI::LEU2 null allele. FIG. 4b shows Northern RNA hybridization analysis of DOA4 gene expression. Lane 1, wild-type (DBY1705) cells carrying YEpDOA4; 2, DBY1705 carrying the YEplac195 vector; 3, doa4-1 (MH11D5–8a); 4, doa4D (MHY622); 5, wild-type (MHY501); 6, MHY501 shifted to 38.5° C. for 30 min; 7, MHY501 treated with 100 mM cadmium acetate for 30 min; 8, MHY501 treated with 20 mg/ml canavanine sulfate for 90 min; and 9, MHY501 grown to stationary phase. 25S, 25S ribosomal RNA. Bottom panel shows the same filter hybridized to a yeast actin sequence. FIG. 4c shows phenotype of doa4 routants.

FIG. 5a shows the degradation of a2 and Deg1-bgal in wild-type (MHY102) and congenic doa4-1 (MH11D5–7b) cells. Proteins from radiolabeled cell extracts were precipitated with an antibody to α2 (Hochstrasser & Varshavsky, 1990). Molecular masses (in kilodaltons) of marker proteins are indicated at right. FIG. 5e shows a dominant-negative allele of DOA4. Degradation rates were measured in MHY102 cells carrying high-copy plasmids that expressed either Doa4 or doa4$^{Ser571}$ proteins. Half-lives calculated by linear regression analysis were 5.8, 3.7, and 17 min for cells carrying YEplac195, YEpDOA4, and YEpDOA4$^{Ser571}$ respectively. FIG. 5f shows Ub-Pro-bgal degradation in cells carrying high-copy pRS424 or pRSDOA4$^{Ser571}$.

FIG. 6a shows an anti-ubiquitin immunoblot analysis of doa4- and DOA$^+$ yeast cells and of DOA$^+$ cells overproducing Doa4. Lane 1, wild-type DBY1705 cells carrying the high-copy YEpDOA4 plasmid; 2, DBY1705 carrying the YEIplac195 vector; 3, doa4-1 cells (MH11D5-8a) carrying YEplac195; 4, wild-type MHY501 (Chen et al.,1993); 5, doa4-D1 cells (MHY623). Free ubiquitin (Ub) is indicated, as is a heterogeneous set of ubiquitin-containing species larger than ubiquitin (arrowhead and bracket). Migration of unanchored multiubiquitin chains ($Ub_2$, $Ub_3$, $Ub_4$, $Ub_5$) was determined using purified Lys48-linked ubiquitin multimers (provided by S. Van Nocker). FIG. 6b shows a model of Doa4 action in the ubiquitin-dependent proteolytic pathway. Doa4 is seen as the prototype of a specialized class of deubiquitinating enzymes whose deubiquitinating activity is coupled to protein breakdown by the 26S proteasome. The possibility of release of relatively large cleavage products, e.g., the M, 90K product of Leu-bgal (FIG. 5), from the protease is indicated in step III.

DETAILED DESCRIPTION OF THE INVENTION

I. The Invention

The present invention shows that one component of the DOA pathway, Doa4, is a deubiquitinating enzyme. Doa4 is a member of what appears to be a large family of deubiquitinating enzymes found in yeast, plants, and animals. Elimination of Doa4 from yeast results in poor growth and many additional defects. Proteolysis of all tested ubiquitin-dependent substrates is strongly inhibited in doa4 mutants. The Doa4 enzyme likely functions late in the proteolytic pathway in conjunction with (or as part of) the 26S proteasome. Doa4 is more similar in sequence to a product of the human tre-2 oncogene (Nakamura, 1992) than to any of the known yeast Ubp proteins, and tre-2, whose function was previously unknown, also encodes a deubiquitinating enzyme. Moreover, a mutation in DOA4 has properties that parallel those of an oncogenic allele of tre-2. Perturbation of ubiquitin-dependent proteolysis in mammalian cells can lead to tumorigenic growth.

The present invention provides DNA segments, purified polypeptides, methods for obtaining antibodies, methods of cloning and using recombinant host cells necessary to obtain and use recombinant deubiquitinating enzymes. Accordingly, the present invention concerns generally compositions and methods for the preparation and use of deubiquitinating enzymes.

II. Polynucleotide

A. Isolated and purified polynucleotide that encode deubiquitinating enzyme polypeptides In one aspect, the present invention provides an isolated and purified polynucleotide that encodes an deubiquitinating enzyme polypeptide. In a preferred embodiment, the polynucleotide of the present invention is a DNA molecule. More preferably, the polynucleotide of the present invention encodes polypeptides that are yeast deubiquitinating enzymes. Even more preferred, a polynucleotide of the present invention encodes a polypeptide comprising the amino acid residue sequence of DOA4 (SEQ ID NO: 2). Most preferably, an isolated and purified polynucleotide of the invention comprises the nucleotide base sequence of SEQ ID NO: 1 from about nucleotide position 271 to about nucleotide position 3048 or SEQ ID NO: 1.

Figure 1A:
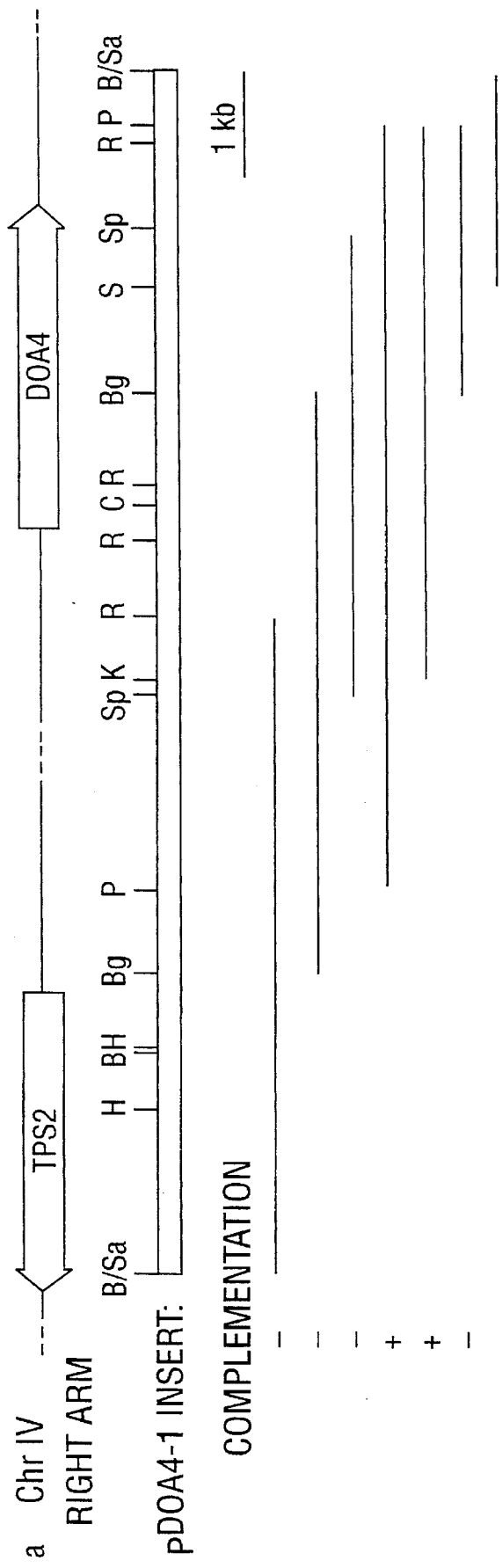

FIG. 1a shows the restriction map of a ~11 kb genomic fragment containing DOA4 and identification of DNA subclones that complement the doa4-1 proteolytic defect. FIG. 1b shows the nucleotide sequence of DOA4 and predicted amino acid sequence of the Doa4 protein. The conserved domains that include a Cys (circled) and two His (boxed) residues (FIG. 2d,e) are bracketed. Upstream of the ORF, two sequences that may play a role in transcription initiation are highlighted, a poly(dA) tract (double underline) (Struhl, 1985) and a potential TATA element (underline) (Singer et al., 1990).

As used herein, the term "polynucleotide" means a sequence of nucleotides connected by phosphodiester linkages. Polynucleotides are presented herein in the direction from the 5' to the 3' direction. A polynucleotide of the present invention can comprise from about 2700 to about several hundred thousand base pairs. Preferably, a polynucleotide comprises from about 2700 to about 150,000 base pairs. Preferred lengths of particular polynucleotide are set forth hereinafter.

A polynucleotide of the present invention can be a deoxyribonucleic acid (DNA) molecule or ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), inosine (I) and uracil (U).

A polynucleotide of the present invention can be prepared using standard techniques well known to one of skill in the art. The preparation of a cDNA molecule encoding an deubiquitinating enzyme polypeptide of the present invention is described hereinafter in the Examples. A polynucleotide can also be prepared from genomic DNA libraries using lambda phage technologies.

In another aspect, the present invention provides an isolated and purified polynucleotide that encodes an deubiquitinating enzyme polypeptide, where the polynucleotide is preparable by a process comprising the steps of constructing a library of cDNA clones from a cell that expresses the polypeptide; screening the library with a labelled cDNA probe prepared from RNA that encodes the polypeptide; and selecting a clone that hybridizes to the probe. Preferably, the polynucleotide of the invention is prepared by the above process. More preferably, the polynucleotide of the invention encodes a polypeptide that has the amino acid residue sequence of SEQ ID NO: 2. More preferably still, the polynucleotide comprises the nucleotide sequence of SEQ ID NO: 1 from about nucleotide position 271 to about nucleotide position 3048 or SEQ ID NO: 1.

B. Probes and Primers

In another aspect, DNA sequence information provided by the present invention allows for the preparation of relatively short DNA (or RNA) sequences having the ability to specifically hybridize to gene sequences of the selected polynucleotide disclosed herein. In these aspects, nucleic acid probes of an appropriate length are prepared based on a consideration of a selected nucleotide sequence, e.g., a sequence such as that shown in SEQ ID NO: 1 from about nucleotide position 271 to about nucleotide position 3048 or SEQ ID NO: 1. The ability of such nucleic acid probes to specifically hybridize to a polynucleotide encoding an deubiquitinating enzyme lends them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of a gene or polynucleotide that encodes an deubiquitinating enzyme polypeptide from mammalian cells using polymerase chain reactive (PCR) technology.

To provide certain of the advantages in accordance with the present invention, a preferred nucleic acid sequence employed for hybridization studies or assays includes probe molecules that are complementary to at least a 10 to 70 or so long nucleotide stretch of a polynucleotide that encodes an deubiquitinating enzyme polypeptide, such as that shown in SEQ ID NO: 2. A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 25 to 40 nucleotides, 55 to 70 nucleotides, or even longer where desired. Such fragments can be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction enzyme sites.

In another aspect, the present invention contemplates an isolated and purified polynucleotide comprising a base sequence that is identical or complementary to a segment of at least 10 contiguous bases of SEQ ID NO: 1, wherein the polynucleotide hybridizes to a polynucleotide that encodes an deubiquitinating enzyme polypeptide. Preferably, the isolated and purified polynucleotide comprises a base sequence that is identical or complementary to a segment of at least 25 to 70 contiguous bases of SEQ ID NO: 1 from about nucleotide position 271 to about nucleotide position 3048 or SEQ ID NO: 1. For example, the polynucleotide of the invention can comprise a segment of bases identical or complementary to 40 or 55 contiguous bases of the disclosed nucleotide sequences.

Accordingly, a polynucleotide probe molecule of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids. For example, one will select relatively low salt and/or high temperature conditions, such as provided by 0.02 M–0.15 M NaCl at temperatures of 50° C. to 70° C. Those conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate an deubiquitinating enzyme polypeptide coding sequence from other cells, functional equivalents, or the like, less stringent hybridization conditions are typically needed to allow formation of the heteroduplex. In these circumstances, one can desire to employ conditions such as 0.15 M–0.9 M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The :selected conditions depend as is well known in the art on the particular circumstances and criteria required (e.g., on the G+C contents, type of target nucleic acid, source of nucleic acid, size of hybridization probe). Following washing of the matrix to remove nonspecifically bound probe molecules, specific hybridization is detected, or even quantified, by means of the label.

II. Deubiquitinating enzyme Polypeptide

In one embodiment, the present invention contemplates an isolated and purified deubiquitinating enzyme polypeptide. Preferably, an deubiquitinating enzyme polypeptide of the invention is a recombinant polypeptide. More preferably, an deubiquitinating enzyme polypeptide of the present invention is a yeast deubiquitinating enzyme polypeptide. Even more preferably, an deubiquitinating enzyme polypeptides of the present invention comprises the amino acid residue sequence of DOA4 (SEQ ID NO: 2). An deubiquitinating enzyme polypeptide preferably comprises less than about 4000 amino acid residues, preferably less than about 2500 amino acid residues and, more preferably less than about 1000 amino acid residues.

Figure 2A:
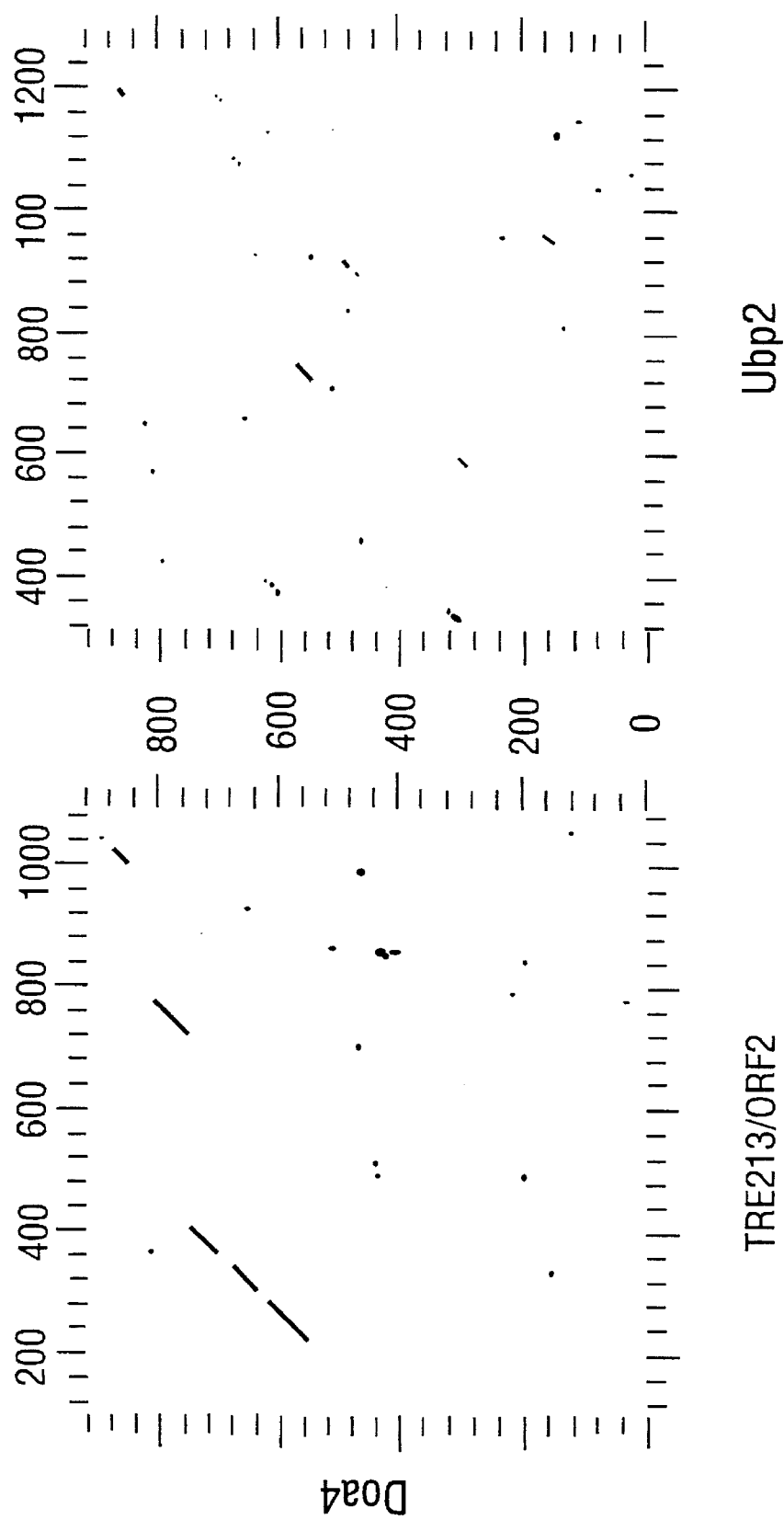
Figure 2B:
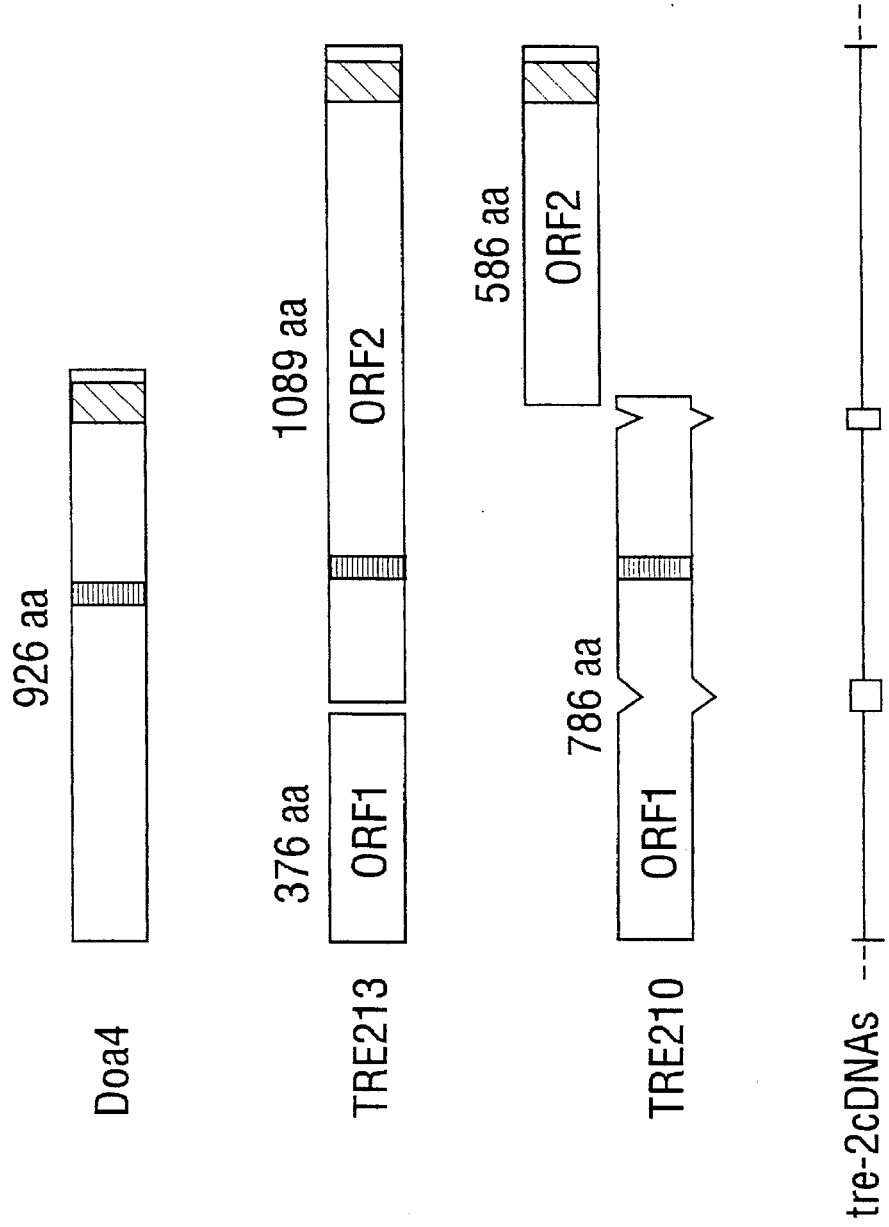
Figure 2D:
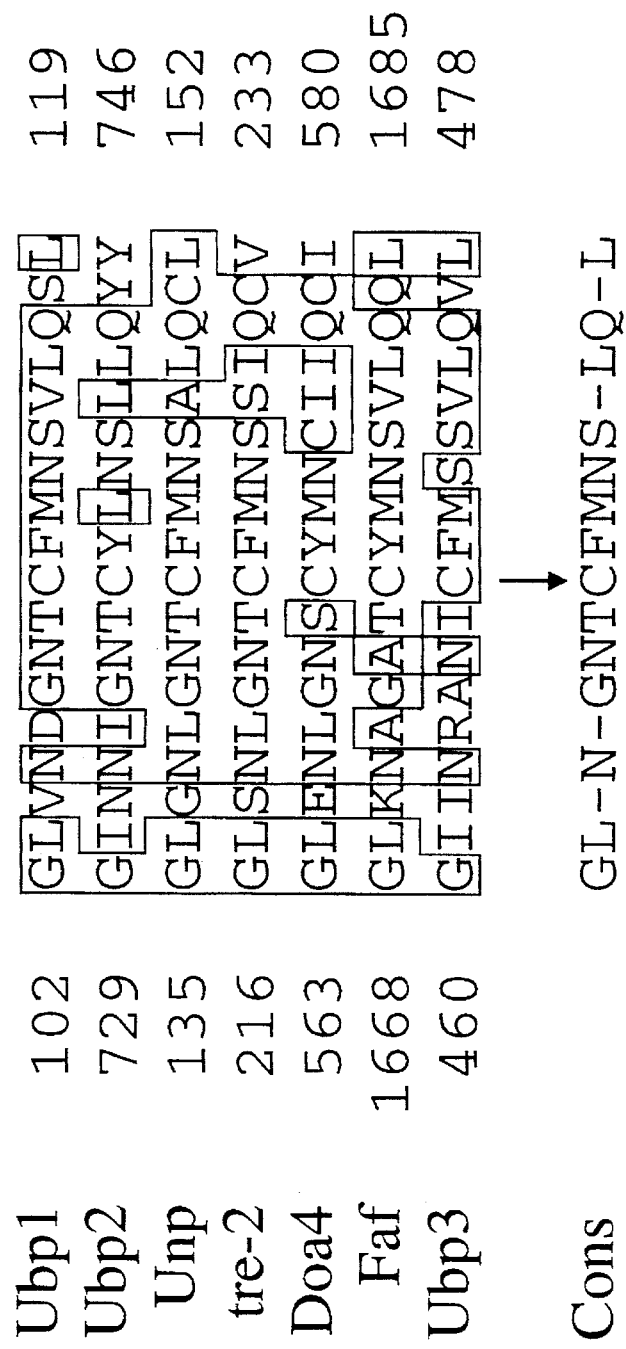

FIG. 2b shows the open reading frames of the yeast DOA4 and human tre-2 (Nakamura, 1992) genes, the latter predicted from two cDNA clones, which differ by two segments present in the TRE213 clone but absent from TRE210 (boxes in cDNA; indents in TRE210/ORF1). The Cys (stippled) and His (hatched) domains are highlighted. FIG. 2c shows sequence conservation between two long elements in Doa4 and tre-2 (TRE213/ORF2). The more amino-terminal region, Block 1 (39% identity/60% similarity (Dayhoff et al., 1988)), includes the Cys domain (FIG. 2d); the smaller element is called Block 2 (43%/61%). A third region, Block 3, is referred to as the His domain (FIG. 2e). Weaker sequence similarities between various family members was observed in Blocks 1 and 2, e.g., the region corresponding to residues 656–675 of Doa4. FIG. 2d and 2e show conserved elements in Doa4 and other deubiquitinating enzymes around the presumptive active site Cys and His residues (arrowheads), including consensus sequences ($\geq 4$ identities). Residues are boxed if present in at least three of the proteins or, in the case of small uncharged (n) or hydrophobic (h) residues, share the indicated property in at least six of the proteins. Sequences compared to Doa4 are yeast Ubp1-Ubp3 (Baker et al., 1992; Tobia & Varshavsky, 1991); mouse Unp (Gupta et al., 1993); human tre-2 (TRE213/ORF2)(Nakamuar, 1992); and *Drosophila fat fac-*

*ets* (*faf*) (Fischer-Vize et al., 1992) (a 22-residue segment was deleted after residue 2029 of faf). Sequences were aligned initially with PILEUP. Many partial cDNA sequences in the GenBank database, identified with BLAST (Altschul et al., 1990), also show significant similarity to regions within Blocks 1–3; these include human (T04867, T09031, Z12710, Z15701, Z21167), *Caenorhabditis elegans* (M80041, Z14720, Z14811), *Arabidopsis thaliani* (Z17750, Z25610), and canine (L03387) sequences.

The present results demonstrate that Doa4 is a central component of the yeast ubiquitin-dependent proteolytic system. Deletion of the DOA4 gene leads to multiple abnormalities (FIG. 4c) despite the fact that *S. cerevisiae* cells have at least four additional deubiquitinating enzymes (Baker et al., 1992). The functional diversity of deubiquitinating enzymes implied by our in vivo data may reflect differences in their substrate specificity or in their mechanistic roles within the ubiquitin pathway. A priori, Doa4/Ubp4-catalyzed deubiquitination reactions could be important in ubiquitin precursor processing, in removing ubiquitin from substrates prior to their commitment to proteolysis, and/or in the proteolytic phase of the degradation pathway. Activity assays with isolated Doa4 (FIG. 3) are consistent with all three roles. However, the data in FIGS. 4–6 strongly suggest that Doa4 functions primarily, if not exclusively, in the late stages of proteolysis in vivo.

Polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated below.

| Amino Acid Residue | 3-Letter Code | 1-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Modifications and changes can be made in the structure of a polypeptide of the present invention and still obtain a molecule having like deubiquitinating enzyme characteristics. For example, certain amino acids can be substituted for other amino acids in a sequence without appreciable loss of enzyme activity. Because it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like properties.

In making such changes, the hydropathic index of amino acids can be considered. The importance of the hydropathic amino acid index in conferring interactive biologic function on a polypeptide is generally understood in the art (Kyte & Doolittle, *J. Mol. Biol.*, 157:105–132, 1982). It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent polypeptide or peptide thereby created is intended for use in immunological embodiments. U.S. Pat. No. 4,554,101, incorporated herein by reference, states that the greatest local average hydrophilicity of a polypeptide, as governed by the hydrophilicity of its adjacent amino acids, correlates with its immunogenicity and antigenicity, i.e. with a biological property of the polypeptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See Table 1, below). The present invention thus contemplates functional or biological equivalents of an deubiquitinating enzyme polypeptide as set forth above.

TABLE 1

| Original Residue | Exemplary Substitutions |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Biological or functional equivalents of a polypeptide can also be prepared using site-specific mutagenesis. Site-specific mutagenesis is a technique useful in the preparation of second generation polypeptides, or biologically functional equivalent polypeptides or peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by Adelman, et al. (1983). As will be appreciated, the technique typically employs a phage vector which can exist in both a single stranded and double stranded form. Typical vectors useful in site-directed mutagenesis include vectors such as the M13 phage (Messing, et al. 1981). These phage are commercially available and their use is generally known to those of skill in the art.

In general, site-directed mutagenesis in accordance herewith is performed by first obtaining a single-stranded vector which includes within its sequence a DNA sequence which encodes all or a portion of the deubiquitinating enzyme polypeptide sequence selected. An oligonucleotide primer bearing the desired mutated sequence is prepared, generally synthetically, for example, by the method of Crea, et al. (1978). This primer is then annealed to the singled-stranded vector, and extended by the use of enzymes such as E. coli polymerase I Klenow fragment, in .order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as E. coli cells and clones are selected which include recombinant vectors bearing the mutation. Commercially available kits come with all the reagents necessary, except the oligonucleotide primers. Examples of mutated deubiquitinating enzymes are set forth hereinafter in the Examples.

An deubiquitinating enzyme polypeptide of the present invention is understood to be any deubiquitinating enzyme polypeptide capable of catalyzing the removal of ubiquitin from protein-ubiquitin conjugates. In addition, an deubiquitinating enzyme polypeptide of the invention is not limited to a particular source. As disclosed herein, the techniques and compositions of the present invention provide, for example, the identification and isolation of de from mouse sources. Thus, the invention provides for the general detection and isolation of the genus of deubiquitinating enzyme polypeptides from a variety of sources while identifying specifically three species of that genus. It is believed that a number of species of the family of deubiquitinating enzyme polypeptides are amenable to detection and isolation using the compositions and methods of the present inventions. See Example 5, hereinafter, showing that tre-2 is a member of the deubiquitinating enzyme family disclosed herein.

A polypeptide of the present invention is prepared by standard techniques well known to those skilled in the art. Such techniques include, but are not limited to, isolation and purification from tissues known to contain that polypeptide, and expression from cloned DNA that encodes such a polypeptide using transformed cells (See the Examples, hereinafter).

Deubiquitinating enzyme polypeptides are found in virtually all plants and animals. As shown by the amino acid sequence homology data herein, there is likely little variation between the structure and function of deubiquitinating enzymes in different species. Where there is a difference between species, identification of those differences is well within the skill of an artisan. Thus, the present invention contemplates an deubiquitinating enzyme polypeptide from any mammal. A preferred mammal is a rodent or a human.

III. Expression Vectors

In an alternate embodiment, the present invention provides expression vectors comprising polynucleotide that encode deubiquitinating enzyme polypeptides. Preferably, the expression vectors of the present invention comprise polynucleotide that encode polypeptides comprising the amino acid residue sequence of SEQ ID NO: 2. More preferably, the expression vectors of the present invention comprise polynucleotide comprising the nucleotide base sequence of SEQ ID NO: 1 from about nucleotide position 271 to about nucleotide position 3048 or SEQ ID NO: 1. Even more preferably, the expression vectors of the invention comprise polynucleotide operatively linked to an enhancer-promoter. More preferably still, the expression vectors of the invention comprise polynucleotide operatively linked to a prokaryotic promoter. Alternatively, the expression vectors of the present invention comprise polynucleotide operatively linked to an enhancer-promoter that is a eukaryotic promoter, and the expression vectors further comprise a polyadenylation signal that is positioned 3' of the carboxy-terminal amino acid and within a transcriptional unit of the; encoded polypeptide.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

A coding sequence of an expression vector is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA). Transcription-terminating regions are well known in the art. A preferred transcription-terminating region used in an adenovirus vector construct of the present invention comprises a polyadenylation signal of SV40 or the profamine gene.

An expression vector comprises a polynucleotide that encodes an deubiquitinating enzyme polypeptide. Such a polypeptide is meant to include a sequence of nucleotide bases encoding an deubiquitinating enzyme polypeptide sufficient in length to distinguish said segment from a polynucleotide segment encoding a non-deubiquitinating enzyme polypeptide. A polypeptide of the invention can also encode biologically functional polypeptides or peptides which have variant amino acid sequences, such as with changes selected based on considerations such as the relative hydropathic score of the amino acids being exchanged. These variant sequences are those isolated from natural sources or induced in the: sequences disclosed herein using a mutagenic procedure such as site-directed mutagenesis.

Preferably, the expression vectors of the present invention comprise polynucleotide that encode polypeptides comprising the amino acid residue sequence of SEQ ID NO: 2. An expression vector can include an deubiquitinating enzyme polypeptide coding region itself of any of the deubiquitinating enzyme polypeptides noted above or it can contain coding regions bearing selected alterations or modifications in the basic coding region of such an deubiquitinating enzyme polypeptide. Alternatively, such vectors or fragments can code larger polypeptides or polypeptides which nevertheless include the basic coding region. In any event, it should be appreciated that due to codon redundancy as well as biological functional equivalence, this aspect of the invention is not limited to the particular DNA molecules corresponding to the polypeptide sequences noted above.

Exemplary vectors include the mammalian expression vectors of the pCMV family including pCMV6b and pCMV6c (Chiron Corp., Emeryville Calif.). In certain cases, and specifically in the case of these individual mammalian expression vectors, the resulting constructs can require co-transfection with a vector containing a selectable marker such as pSV2neo. Via co-transfection into a dihydrofolate reductase-deficient Chinese hamster ovary cell line, such as DG44, clones expressing polypeptides by virtue of DNA incorporated into such expression vectors can be detected.

A DNA molecule of the present invention can be incorporated into a vector by a number of techniques which are well known in the art. For instance, the vector pUC 18 has been demonstrated to be of particular value. Likewise, the related vectors M13mp18 and M13mp19 can be used in certain embodiments of the invention, in particular, in performing dideoxy sequencing.

An expression vector of the present invention is useful both as a means for preparing quantities of the deubiquitinating enzyme polypeptide-encoding DNA itself, and as a means for preparing the encoded polypeptide and peptides. It is contemplated that where deubiquitinating enzyme polypeptides of the invention are made by recombinant means, one can employ either prokaryotic or eukaryotic expression vectors as shuttle systems. However, in that prokaryotic systems are usually incapable of correctly processing precursor polypeptides and, in particular, such systems are incapable of correctly processing membrane associated eukaryotic polypeptides, and since eukaryotic deubiquitinating enzyme polypeptides are anticipated using the teaching of the disclosed invention, one likely expresses such sequences in eukaryotic hosts. However, even where the DNA segment encodes a eukaryotic deubiquitinating enzyme polypeptide, it is contemplated that prokaryotic expression can have some additional applicability. Therefore, the invention can be used in combination with vectors which can shuttle between the eukaryotic and prokaryotic cells. Such a system is described herein which allows the use of bacterial host cells as well as eukaryotic host cells.

Where expression of recombinant deubiquitinating enzyme polypeptides is desired and a eukaryotic host is contemplated, it is most desirable to employ a vector such as a plasmid, that incorporates a eukaryotic origin of replication. Additionally, for the purposes of expression in eukaryotic systems, one desires to position the deubiquitinating enzyme encoding sequence adjacent to and under the control of an effective eukaryotic promoter such as promoters used in combination with Chinese hamster ovary cells. To bring a coding sequence under control of a promoter, whether it is eukaryotic or prokaryotic, what is generally needed is to position the 5' end of the translation initiation side of the proper translational reading frame of the polypeptide between about 1 and about 50 nucleotides 3' of or downstream with respect to the promoter chosen. Furthermore, where eukaryotic expression is anticipated, one would typically desire to incorporate into the transcriptional unit which includes the deubiquitinating enzyme polypeptide, an appropriate polyadenylation site.

The pCMV plasmids are a series of mammalian expression vectors of particular utility in the present invention. The vectors are designed for use in essentially all cultured cells and work extremely well in SV40-transformed simian COS cell lines. The pCMV1, 2, 3, and 5 vectors differ from each other in certain unique restriction sites in the polylinker region of each plasmid. The pCMV4 vector differs from these 4 plasmids in containing a translation enhancer in the sequence prior to the polylinker. While they are not directly derived from the pCMV 1–5 series of vectors, the functionally similar pCMV6b and c vectors are available from the Chiron Corp. of Emeryville, Calif. and are identical except for the orientation of the polylinker region which is reversed in one relative to the other.

The universal components of the pCMV plasmids are as follows. The vector backbone is pTZ18R (Pharmacia), and contains a bacteriophage f1 origin of replication for production of single stranded DNA and an ampicillin-resistance gene. The CMV region consists of nucleotides −760 to +3 of the powerful promoter-regulatory region of the human cytomegalovirus (Towne stain) major immediate early gene (Thomsen et al., 1984; Boshart et al., 1985). The human growth hormone fragment (hGH) contains transcription termination and poly-adenylation signals representing sequences 1533 to 2157 of this gene (Seeburg, 1982). There is an Alu middle repetitive DNA sequence in this fragment. Finally, the SV40 origin of replication and early region promoter-enhancer derived from the pcD-X plasmid (HindII to PstI fragment) described in (Okayama et al., 1983). The promoter in this fragment is oriented such that transcription proceeds away from the CMV/hGH expression cassette.

The pCMV plasmids are distinguishable from each other by differences in the polylinker region and by the presence or absence of the translation enhancer. The starting pCMV1 plasmid has been progressively modified to render an increasing number of unique restriction sites in the polylinker region. To create pCMV2, one of two EcoRI sites in pCMV1 were destroyed. To create pCMV3, pCMV1 was modified by deleting a short segment from the SV40 region (StuI to EcoRI), and in so doing made unique the PstI, SalI, and BamHI sites in the polylinker. To create pCMV4, a synthetic fragment of DNA corresponding to the 5′-untranslated region of a mRNA transcribed from the CMV promoter was added C. The sequence acts as a translational enhancer by decreasing the requirements for initiation factors in polypeptide synthesis (Jobling et al., 1987); Browning et al., 1988). To create pCMV5, a segment of DNA (HpaI to EcoRI) was deleted from the SV40 origin region of pCMV1 to render unique all sites in the starting polylinker.

The pCMV vectors have been successfully expressed in simian COS cells, mouse L cells, CHO cells, and HeLa cells. In several side by side comparisons they have yielded 5- to 10-fold higher expression levels in COS cells than SV40-based vectors. The pCMV vectors have been used to express the LDL receptor, nuclear factor 1, $G_s$ alpha polypeptide, polypeptide phosphatase, synaptophysin, synapsin, insulin receptor, influenza hemmagglutinin, androgen receptor, sterol 26-hydroxylase, steroid 17- and 21-hydroxylase, cytochrome P-450 oxidoreductase, beta-adrenergic receptor, folate receptor, cholesterol side chain cleavage enzyme, and a host of other cDNAs. It should be noted that the SV40 promoter in these plasmids can be used to express other genes such as dominant selectable markers. Finally, there is an ATG sequence in the polylinker between the HindIII and PstI sites in pCMU that can cause spurious translation initiation. This codon should be avoided if possible in expression plasmids. A paper describing the construction and use of the parenteral pCMV1 and pCMV4 vectors has been published (Anderson et al., 1989b).

The making and using of expression vectors comprising a polynucleotide that encodes a deubiquitinating enzyme of the present invention described in detail hereinafter in the Examples.

IV. Transfected Cells

In yet another embodiment, the present invention provides recombinant host cells transformed or transfected with polynucleotide that encode deubiquitinating enzyme polypeptides, as well as transgenic cells derived from those transformed or transfected cells. Preferably, the recombinant host cells of the present invention are transfected with polynucleotide of SEQ ID NO: 1 from about nucleotide position 271 to about nucleotide position 3048 or SEQ ID NO: 1. Means of transforming or transfecting cells with exogenous polynucleotide such as DNA molecules are well known in the art and include techniques such as calcium-phosphate- or DEAE-dextran-mediated transfection, protoplast fusion, electroporation, liposome mediated transfection, direct microinjection and adenovirus infection (Sambrook, Fritsch and Maniatis, 1989).

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

In the protoplast fusion method, protoplasts derived from bacteria carrying high numbers of copies of a plasmid of interest are mixed directly with cultured mammalian cells. After fusion of the cell membranes (usually with polyethylene glycol), the contents of the bacteria are delivered into the cytoplasm of the mammalian cells and the plasmid DNA is transported to the nucleus. Protoplast fusion is not as efficient as transfection for many of the cell lines that are commonly used for transient expression assays, but it is useful for cell lines in which endocytosis of DNA occurs inefficiently. Protoplast fusion frequently yields multiple copies of the plasmid DNA tandemly integrated into the host chromosome.

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Liposome transfection involves encapsulation of DNA and RNA within liposomes, followed by fusion of the liposomes with the cell membrane. The mechanism of how DNA is delivered into the cell is unclear but transfection efficiencies can be as high as 90%.

Direct microinjection of a DNA molecule into nuclei has the: advantage of not exposing DNA to cellular compartments such as low-pH endosomes. Microinjection is therefore used primarily as a method to establish lines of cells that carry integrated copies of the DNA of interest.

The use of adenovirus or baculoviruses as a vector for cell transfection is well known in the art. Adenovirus vector-mediated cell transfection has been reported for various cells (Stratford-Perricaudet, et al. 1992).

A transfected cell can be prokaryotic or eukaryotic. Preferably, the host cells of the invention are eukaryotic host cells. More preferably, the recombinant host cells of the invention are COS-1 cells. Where it is of interest to produce a human deubiquitinating enzyme polypeptides, cultured mammalian or human cells are of particular interest.

In another aspect, the recombinant host cells of the present invention are prokaryotic host cells. Preferably, the recombinant host cells of the invention are bacterial cells of the DH5α strain of *Escherichia coli*. In general, prokaryotes are preferred for the initial cloning of DNA sequences and constructing the vectors useful in the invention. For example, *E. coli* K12 strains can be particularly useful. Other microbial strains which can be used include *E. coli* B, and *E. coli* X1776 (ATCC No. 31537). These examples are, of course, intended to be illustrative rather than limiting.

Prokaryotes can also be used for expression. The aforementioned strains, as well as *E. coli* W3110 (F-, lambda-, prototrophic, ATCC No. 273325), bacilli such as *Bacillus subtilus*, or other enterobacteriaceae such as *Salmonella typhimurium* or *Serratus marcesans*, and various Pseudomonas species can be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* can be transformed using pBR322, a plasmid derived from an *E. coli* species (Bolivar, et al. 1977). pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

Those promoters most commonly used in recombinant DNA construction include the β-lactamase (penicillinase) and lactose promoter systems (Chang, et al. 1978; Itakura, et al. 1977; Goeddel, et al. 1979; Goeddel, et al. 1980) and a tryptophan (TRP) promoter system (EPO Appl. Publ. No. 0036776; Siebwenlist et al., 1980). While these are the most commonly used, other microbial promoters have been discovered and utilized, and details concerning their nucleotide sequences have been published, enabling a skilled worker to introduce functional promoters into plasmid vectors (Siebwenlist, et al. 1980).

In addition to prokaryotes, eukaryotic microbes such as yeast can also be used. *Saccharomyces cerevisiae* or common baker's yeast is the most commonly used among eukaryotic microorganisms, although a number of other strains are commonly available. For expression in Saccharomyces, the plasmid YRp7, for example, is commonly used (Stinchcomb, et al. 1979; Kingsman, et al. 1979, Tschemper, et al. 1980). This plasmid already contains the trpl gene which provides a selection marker for a mutant strain of yeast lacking the ability to grow in tryptophan, for example ATCC No. 44076 or PEP4-1 (Jones, 1977). The presence of the trp1 lesion as a characteristic of the yeast host cell genome then provides an effective environment for detecting transformation by growth in the absence of tryptophan.

Suitable promoter sequences in yeast vectors include the promoters for 3-phosphoglycerate kinase (Hitzeman, et al. 1980) or other glycolytic enzymes (Hess, et al. 1968; Holland, et al. 1978) such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the: sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable.

In addition to microorganisms, cultures of cells derived from multicellular organisms can also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years (Kruse and Peterson, 1973). Examples of such useful host cell lines are AtT-20, VERO and HeLa cells, Chinese hamster ovary (CHO) cell lines, and W138, BHK, COSM6, COS-7, 293 and MDCK cell lines. Expression vectors for such cells ordinarily include (if necessary) an origin of replication, a promoter located upstream of the gene to be expressed, along with any necessary ribosome binding sites, RNA splice sites, polyadenylation site, and transcriptional terminator sequences.

For use in mammalian cells, the control functions on the expression vectors are often derived from viral material. For example, commonly used promoters are derived from polyoma, Adenovirus 2, Cytomegalovirus and most frequently Simian Virus 40 (SV40). The early and late promoters of SV40 virus are particularly useful because both are obtained easily from the virus as a fragment which also contains the SV40 viral origin of replication (Fiers, et al. 1978). Smaller or larger SV40 fragments can also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication can be provided with by construction of the vector to include an exogenous origin, such as can be derived from SV40 or other viral (e.g., Polyoma, Adeno, VSV, BPV, CMV) source, or can be provided by the host cell chromosomal replication mechanism. If the vector is integrated into the host cell chromosome, the latter is often sufficient.

V. Preparing Recombinant Deubiquitinating Enzyme Polypeptides.

In yet another embodiment, the present invention contemplates a process of preparing deubiquitinating enzyme polypeptides comprising transfecting cells with polynucleotide that encode deubiquitinating enzyme polypeptides to produce transformed host cells; and maintaining the transformed host cells under biological conditions sufficient for expression of the polypeptide. The transformed host cells can be eukaryotic cells such as COS-1 cells. Alternatively, the host cells are prokaryotic cells. More preferably, the prokaryotic cells are bacterial cells of the DH5α strain of *Escherichia coli*. Even more preferably, the polynucleotide transfected into the transformed cells comprise the nucleotide base sequence of SEQ ID NO: 1 from about nucleotide position 271 to about nucleotide position 3048 or SEQ ID NO: 1. Most preferably transfection is accomplished using a hereinbefore disclosed expression vector.

A host cell used in the process is capable of expressing a functional, recombinant deubiquitinating enzyme polypeptide. A variety of cells are amenable to a process of the invention, for instance, yeasts cells, human cell lines, and other eukaryotic cell lines known well to those of skill in the art.

Following transfection, the cell is maintained under culture conditions for a period of time sufficient for expression of an deubiquitinating enzyme polypeptide. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C., more preferably from about 30° C. to about 40° C. and, even more preferably about 37° C.

pH is preferably from about a value of 6.0 to a value of about 8.0, more preferably from about a value of about 6.8 to a value of about 7.8 and, most preferably about 7.4. Osmolality is preferably from about 200 milliosmols per liter (mosm/L) to about 400 mosm/l and, more preferably from about 290 mosm/L to about 310 mosm/L. Other biological conditions needed for transfection and expression of an encoded protein are well known in the art.

Transfected cells are maintained for a period of time sufficient for expression of an deubiquitinating enzyme polypeptide. A suitable time depends inter alia upon the cell type used and is readily determinable by a skilled artisan. Typically, maintenance time is from about 2 to about 14 days.

Recombinant deubiquitinating enzyme polypeptide is recovered or collected either from the transfected cells or the medium in which those cells are cultured. Recovery comprises isolating and purifying the deubiquitinating enzyme polypeptide. Isolation and purification techniques for polypeptides are well known in the art and include such procedures as precipitation, filtration, chromatography, electrophoresis and the like.

VI. Antibodies

In still another embodiment, the present invention provides antibodies immunoreactive with deubiquitinating enzyme polypeptides. Preferably, the antibodies of the invention are monoclonal antibodies. More preferably, the deubiquitinating enzyme polypeptides comprise the amino acid residue sequence of SEQ ID NO: 2. Means for preparing and characterizing antibodies are well known in the art (See, e.g., *Antibodies "A Laboratory Manual"*, E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of nonspecific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a process of producing an antibody immunoreactive with an deubiquitinating enzyme polypeptide comprising the steps of (a) transfecting recombinant host cells with polynucleotide that encode deubiquitinating enzyme polypeptides; (b) culturing the host cells under conditions sufficient for expression of the polypeptides; (c) recovering the polypeptides; and (d) preparing the antibodies to the polypeptides. Preferably, the host cell is transfected with the polynucleotide of SEQ ID NO: 1 from about nucleotide position 271 to about nucleotide position 3048 or SEQ ID NO: 1. Even more preferably, the present invention provides antibodies prepared according to the process described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptide. The selected clones can then be propagated indefinitely to provide the monoclonal antibody.

By way of specific example, to produce an antibody of the present invention, mice are injected intraperitoneally with between about 1–200 μg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thyroidinc). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

VII. Pharmaceutical Compositions

In a preferred embodiment, the present invention provides pharmaceutical compositions comprising deubiquitinating enzyme polypeptides and physiologically acceptable carriers. More preferably, the pharmaceutical compositions comprise deubiquitinating enzyme polypeptides comprising the amino acid residue sequence of SEQ ID NO: 2. Even more preferably, the pharmaceutical compositions of the invention comprise polynucleotide that encode deubiquitinating enzyme polypeptides, and physiologically acceptable carriers. Still more preferably, the pharmaceutical compositions of the present invention comprise deubiquitinating enzyme polypeptides comprising the amino acid residue sequence of SEQ ID NO: 2. Alternatively, the pharmaceutical compositions comprise polynucleotide comprising the nucleotide sequence of SEQ ID NO: 1 from about nucleotide position 271 to about nucleotide position 3048 or SEQ ID NO: 1.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art [See, e.g. Gabizon et al., 1990; Ferruti et al., 1986, and Ranade, V. V., 1989].

A transfected cell can also serve as a carder. By way of example, a liver cell can be removed from an organism, transfected with a polynucleotide of the present invention using methods set forth above and then the transfected cell returned to the organism (e.g. injected intravascularly).

VIII. Detecting Polynucleotide and the Polypeptides Encoded.

Alternatively, the present invention provides a process of detecting deubiquitinating enzyme polypeptides, wherein the process comprises immunoreacting the polypeptides with antibodies prepared according to the process described above to form antibody-polypeptide conjugates, and detecting the conjugates.

In yet another embodiment, the present invention contemplates a process of detecting messenger RNA transcripts that encode deubiquitinating enzyme polypeptides, wherein the process comprises (a) hybridizing the messenger RNA transcripts with polynucleotide sequences that encode the deubiquitinating enzyme polypeptides to form duplexes; and (b) detecting the duplex. Alternatively, the present invention provides a process of detecting DNA molecules that encode deubiquitinating enzyme polypeptides, wherein the process comprises (a) hybridizing DNA molecules with polynucleotide that encode deubiquitinating enzyme polypeptides to form duplexes; and (b) detecting the duplexes.

IX. Screening Assays

In yet another aspect, the present invention contemplates a process of screening substances for their ability to interact with deubiquitinating enzyme polypeptides comprising the steps of providing deubiquitinating enzyme polypeptides, and testing the ability of selected substances to interact with the deubiquitinating enzyme polypeptides.

Utilizing the methods and compositions of the present invention, screening assays for the testing of candidate substances such as agonists and antagonists of deubiquitinating enzymes can be derived. A candidate substance is a substance which potentially can interact with or modulate, by binding or other intramolecular interaction, an deubiquitinating enzyme polypeptide. In some instances, such a candidate substance will be an agonist of the enzyme and in other instances can exhibit antagonistic attributes when interacting with the enzyme polypeptide. In other instances, such substances can have mixed agonistic and antagonistic properties or can modulate the deubiquitinating enzyme in other ways such as by interacting with a protein or protein fragment attached to a deubiquitinating enzyme.

Recombinant enzyme expression systems of the present invention possess definite advantages over tissue-based systems. The methods of the present invention make it possible to produce large quantities of deubiquitinating enzymes for use in screening assays. More important, however, is the relative purity of the enzyme polypeptides provided by the present invention. A relatively pure polypeptide preparation for assaying a protein-protein interaction makes it possible to use elutive methods without invoking competing, and unwanted, side-reactions.

Traditionally, screening assays employed the use of crude enzyme preparations. Typically, animal tissue slices thought to be rich in the enzyme of interest was the source of the enzyme. Alternatively, investigators homogenized the tissue and used the crude homogenate as a enzyme source. A major difficulty with this approach is that there are no tissue types where only one enzyme type is expressed. The data obtained therefore could not be definitively correlated with a particular enzyme. With the availability of cloned enzymes, recombinant enzyme screening systems have several advantages over tissue based systems. A major advantage is that the investigator can now control the type of enzyme that is utilized in a screening assay. Specific enzyme sub-types and sub-sub-types can be preferentially expressed and its interaction with a ligand can be identified. Other advantages include the availability of large amounts of enzyme, the availability of rare enzymes previously unavailable in tissue samples, and the lack of expenses associated with the maintenance of live animals.

Screening assays of the present invention generally involve determining the ability of a candidate substance to bind to the enzyme and to affect the activity of the enzyme, such as the screening of candidate substances to identify those that inhibit or otherwise modify the enzyme's function. Typically, this method includes preparing recombinant enzyme polypeptide, followed by testing the recombinant polypeptide or cells expressing the polypeptide with a candidate substance to determine the ability of the substance to affect its physiological function. In preferred embodiments, the invention relates to the screening of candidate substances to identify those that affect the enzymatic activity of a human enzyme, and thus can be suitable for use in humans.

As is well known in the art, a screening assay provides a enzyme under conditions suitable for the binding of an agent to the enzyme or the substate of that enzyme (e.g., a protein). These conditions include: but are not limited to pH, temperature, tonicity, the presence of relevant co-factors, and relevant modifications to the polypeptide such as glycosylation or prenylation. It is contemplated that the enzyme can be expressed and utilized in a prokaryotic or eukaryotic cell. The host cell expressing the enzyme can be used whole or the enzyme can be isolated from the host cell. The enzyme can be membrane bound in the membrane of the host cell or it can be free in the cytosol of the host cell. The host cell can also be fractionated into sub-cellular fractions where the enzyme can be found. For example, cells expressing the enzyme can be fractionated into the nuclei, the endoplasmic reticulum, vesicles, or the membrane surfaces of the cell.

pH is preferably from about a value of 6.0 to a value of about 8.0, more preferably from 7.4. about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of co-factors can be required for the proper functioning of the enzyme. Typical co-factors include sodium, potassium, calcium, magnesium, and chloride. In addition, small, non-peptide molecules, known as prosthetic groups can be required. Other biological conditions needed for enzyme function are well known in the art.

It is well known in the art that proteins can be reconstituted in artificial membranes, vesicles or liposomes. (Danboldt, et al. 1990). The present invention contemplates that the enzyme can be incorporated into artificial membranes, vesicles or liposomes. The reconstituted enzyme can be utilized in screening assays.

It is further contemplated that the enzyme of the present invention can be coupled to a solid support. The solid support can be agarose beads, polyacrylamide beads, polyacrylic beads or other solid matrices capable of being coupled to proteins. Well known coupling agents include cyanogen bromide, carbonyldiimidazole, tosyl chloride, and gluteraldehyde.

In a typical screening assay for identifying candidate substances, one employs the same recombinant expression host as the starting source for obtaining the enzyme polypeptide, generally prepared in the form of a crude homogenate. Recombinant cells expressing the enzyme are washed and homogenized to prepare a crude polypeptide homogenate in a desirable buffer such as disclosed herein. In a typical assay, an amount of polypeptide from the cell homogenate is placed into a small volume of an appropriate assay buffer at an appropriate pH. Candidate substances, such as agonists and antagonists, are added to the admixture in convenient concentrations and the interaction between the candidate substance and the enzyme polypeptide is monitored.

Where one uses an appropriate known substrate for the enzyme, one can, in the foregoing manner, obtain a baseline activity for the recombinantly produced enzyme. Then, to test for inhibitors or modifiers of the enzyme function, one can incorporate into the admixture a candidate substance whose effect on the enzyme is unknown. By comparing reactions which are carried out in the presence or absence of the candidate substance, one can then obtain information regarding the effect of the candidate substance on the normal function of the enzyme.

Accordingly, it is proposed that this aspect of the present invention provides those of skill in the art with methodology that allows for the identification of candidate substances having the ability to modify the action of deubiquitinating enzyme polypeptides in one or more manners.

Additionally, screening assays for the testing of candidate substances are designed to allow the investigation of structure activity relationships of other molecules with the enzyme, e.g., study of binding of naturally occurring hormones or other substances capable of interacting or otherwise modulating with the enzyme versus studies of the activity caused by the binding of such molecules to the enzyme. In certain embodiments, the polypeptides of the invention are crystallized in order to carry out x-ray crystallographic studies as a means of evaluating interactions with candidate substances or other molecules with the deubiquitinating enzyme polypeptide. For instance, the purified recombinant polypeptides of the invention, when crystallized in a suitable form, are amenable to detection of intra-molecular interactions by x-ray crystallography.

An important aspect of the invention is the use of recombinantly produced deubiquitinating enzyme polypeptide in screening assays for the identification of substances which can inhibit or otherwise modify or alter the function of the enzyme. The use of recombinantly produced enzyme is of particular benefit because the naturally occurring enzyme is present in only small quantities and has proven difficult to purify. Moreover, this provides a ready source of enzyme, which has heretofore been unavailable.

The enzyme can be expressed in a prokaryotic or a eukaryotic cell. Many biologically active molecules such as receptors have been expressed in E. coli (Berlin, et al. 1992), in yeast (King, et al. (1990) and in mammalian cells (Bouvier, et. al. 1988).

A cell expressing a enzyme can be used whole to screen agents. For example, cells expressing the enzyme of the present invention can be exposed to radiolabelled agent and the amount of binding of the radiolabelled agent to the cell can be determined.

The cell expressing the enzyme can be fractionated into sub-cellular components which contain the enzyme of the present invention. Methods for purifying sub-cellular fractions are well known in the art. Sub-cellular fractions include but are not limited to the cytoplasm, cellular membrane, other membranous fractions such as the endoplasmic reticulum, golgi bodies, vesicles and the nucleus. Enzymes isolated as sub-cellular fractions can be associated with cellular membranes. For example, if cellular membrane vesicles are isolated from the cell expressing the enzyme, the enzyme molecule can be membrane bound. It is further contemplated that the enzyme of the present invention can be purified from a cell that expresses the enzyme. Methods of purification are well known in the art. The purified enzyme can be used in screening assays.

There are believed to be a wide variety of embodiments which can be employed to determine the effect of the candidate substance on the enzyme polypeptides of the invention, and the invention is not intended to be limited to any one such method. However, it is generally desirable to employ a system wherein one can measure the ability of the enzyme polypeptide to bind to and or be modified by the effector employed in the presence of a particular substance.

The detection of an interaction between an agent and a enzyme can be accomplished through techniques well known in the art. These techniques include but are not limited to centrifugation, chromatography, electrophoresis and spectroscopy. The use of isotopically labelled reagents in conjunction radioactive isotopes include $^3$H, $^{14}$C, $^{22}$Na, with these techniques or alone is also contemplated. Commonly used radioactive isotopes includes $^3$H, $^{14}$C, $^{22}$Na, $^{32}$P, $^{35}$S, $^{45}$Ca, $^{60}$Co, $^{125}$I, and $^{131}$I. Commonly used stable isotopes include $^2$H, $^{13}$C, $^{15}$N, $^{18}$O.

For example, if an agent can bind to the enzyme of the present invention, the binding can be detected by using radiolabelled agent or radiolabelled enzyme. Briefly, if radiolabelled agent or radiolabelled enzyme is utilized, the agent-enzyme complex can be detected by liquid scintillation or by exposure to X-Ray film.

When an agent modifies the enzyme, the modified enzyme can be detected by differences in mobility between the modified enzyme and the unmodified enzyme through the use of chromatography, electrophoresis or centrifugation. When the technique utilized is centrifugation, the differences in mobility is known as the sedimentation coefficient. The modification can also be detected by differences between the spectroscopic properties of the modified and unmodified enzyme. As a specific example, if an agent covalently modifies a enzyme, the difference in retention times between modified and unmodified enzyme on a high pressure liquid chromatography (HPLC) column can easily be detected.

The interaction of an agent and a enzyme can be detected by providing a reporter gene. Well known reporter genes include β-galactosidase (β-Gal), chloramphenicol transferase (CAT) and luciferase. The reporter gene is expressed by the host and the enzymatic reaction of the reporter gene product can be detected.

In preferred assays, an admixture containing the polypeptide, effector and candidate substance is allowed to incubate for a selected amount of time, and the resultant incubated mixture subjected to a separation means to separate the unbound effector remaining in the admixture from any effector/enzyme complex so produced. Then, one simply measures the amount of each (e.g., versus a control to which no candidate substance has been added). This measurement can be made at various time points where velocity data is desired. From this, one can determine the ability of the candidate substance to alter or modify the function of the enzyme.

Numerous techniques are known for separating the effector from effector/enzyme complex, and all such methods are intended to fall within the scope of the invention. Use of thin layer chromatographic methods (TLC), HPLC, spectrophotometric, gas chromatographic/mass spectrophotometric or NMR analyses. It is contemplated that any such technique can be employed so long as it is capable of differentiating between the effector and complex, and can be used to determine enzymatic function such as by identifying or quantifying the substrate and product.

The effector/enzyme complex itself can also be the subject of techniques such as x-ray crystallography. Where a candidate substance replaces the effector molecule as the drug's mode of action, studies designed to monitor the replacement and its effect on the enzyme will be of particular benefit.

A. Screening assays for deubiquitinating enzyme polypeptides

The present invention provides a process of screening a biological sample for the presence of an deubiquitinating enzyme polypeptide. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the deubiquitinating enzyme polypeptide whose presence is being assayed. Typically, exposure is accomplished by forming an admixture in a liquid medium that contains both the antibody and the candidate deubiquitinating enzyme polypeptide. Either the antibody or the sample with the deubiquitinating enzyme polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the deubiquitinating enzyme polypeptide.

Exposure time will vary inter alia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$ M, exposure time is from about 10 minutes to about 200 minutes.

The presence of deubiquitinating enzyme polypeptide in the sample is detected by detecting the formation and presence of antibody-deubiquitinating enzyme polypeptide conjugates. Means for detecting such antibody-antigen (e.g., enzyme polypeptide) conjugates or complexes are well known in the art and include such procedures as centrifugation, affinity chromatography and the like, binding of a secondary antibody to the antibody-candidate enzyme complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Means for affixing indicators to antibodies are well known in the art. Commercial kits are available.

B. Screening assay for anti-deubiquitinating enzyme antibody.

In another aspect, the present invention provides a process of screening a biological sample for the presence of antibodies immunoreactive with an deubiquitinating enzyme polypeptide (i.e., an anti-deubiquitinating enzyme antibody). In accordance with such a process, a biological sample is exposed to an deubiquitinating enzyme polypeptide under biological conditions and for a period of time sufficient for antibody-polypeptide conjugate formation and the formed conjugates are detected.

C. Screening assay for polynucleotide that encodes an deubiquitinating enzyme polypeptide A DNA molecule and, particularly a probe molecule, can be used for hybridizing as oligonucleotide probes to a DNA source suspected of possessing an deubiquitinating enzyme polypeptide encoding polynucleotide or gene. The probing is usually accomplished by hybridizing the oligonucleotide to a DNA source suspected of possessing such a enzyme gene. In some cases, the probes constitute only a single probe, and in others, the probes constitute a collection of probes based on a certain amino acid sequence or sequences of the deubiquitinating enzyme polypeptide and account in their diversity for the redundancy inherent in the genetic code.

A suitable source of DNA for probing in this manner is capable of expressing deubiquitinating enzyme polypeptides and can be a genomic library of a cell line of interest. Alternatively, a source of DNA can include total DNA from the cell line of interest. Once the hybridization process of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) means for detecting and isolating other members of the deubiquitinating enzyme family and related polypeptides from a DNA library potentially containing such sequences; (3) primers for hybridizing to related sequences for the purpose of amplifying those sequences; (4) primers for altering the native deubiquitinating enzyme DNA sequences; as well as other techniques which rely on the similarity of the DNA sequences to those of the deubiquitinating enzyme DNA segments herein disclosed.

As set forth above, in certain aspects, DNA sequence information provided by the invention allows for the preparation of relatively short DNA (or RNA) sequences (e.g., probes) that specifically hybridize to encoding sequences of the selected deubiquitinating enzyme gene. In these aspects, nucleic acid probes of an appropriate length are prepared based on a consideration of the selected deubiquitinating enzyme sequence (e.g., a sequence such as that shown in SEQ ID NO: 2). The ability of such nucleic acid probes to specifically hybridize to deubiquitinating enzyme encoding sequences lend them particular utility in a variety of embodiments. Most importantly, the probes can be used in a variety of assays for detecting the presence of complementary sequences in a given sample. However, uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of the deubiquitinating enzyme encoding sequence, such as that shown in SEQ ID NO: 1 from about nucleotide position 271 to about nucleotide position 3048 or SEQ ID NO: 1. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR technology of U.S. Pat. No. 4,603,102, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M–0.15M NaCl at temperatures of 50° C. to 70° C. Such conditions are particularly selective, and tolerate little, if any, mismatch between the probe and the template or target strand.

Of course, for some applications, for example, where one desires to prepare routants employing a mutant primer strand hybridized to an underlying template or where one seeks to isolate deubiquitinating enzyme coding sequences from related species, functional equivalents, or the like, less stringent hybridization conditions are typically needed to allow formation of the heteroduplex. Under such circumstances, one employs conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend inter alia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization; is detected, or even quantified, by means of the label.

X. Assay kits

In another aspect, the present invention contemplates diagnostic assay kits for detecting the presence of deubiquitinating enzyme polypeptides in biological samples, where the kits comprise a first container containing a first antibody capable of immunoreacting with deubiquitinating enzyme polypeptides, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also contemplates a diagnostic kit for screening agents. Such a kit can contain an deubiquitinating enzyme of the present invention. The kit can contain reagents for detecting an interaction between an agent and a enzyme of the present invention. The provided reagent can be radiolabelled. The kit can contain a known radiolabelled agent capable of binding or interacting with a enzyme of the present invention.

In an alternative aspect, the present invention provides diagnostic assay kits for detecting the presence, in biological samples, of polynucleotide that encode deubiquitinating enzyme polypeptides, the kits comprising a first container that contains a second polynucleotide identical or complementary to a segment of at least 10 contiguous nucleotide bases of SEQ ID NO: 1.

In another embodiment, the present invention contemplates diagnostic assay kits for detecting the presence, in a biological sample, of antibodies immunoreactive with deubiquitinating enzyme polypeptides, the kits comprising a first container containing an deubiquitinating enzyme polypeptide that immunoreacts with the antibodies, with the polypeptides present in an amount sufficient to perform at least one assay. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide. When the reagent provided is a dry powder, the powder can be reconstituted by the addition of a suitable solvent. The solvent can be provided.

XI. A Process of Deubiquitinating Proteins

In another aspect, the present invention provides a process of regulating protein degradation by regulating deubiquitination of those proteins. Proteins whose degradation is ubiquitin-dependent are well known in the art. By way of example, many short-lived eukaryotic proteins, covalent attachment to the polypeptide ubiquitin is a prerequisite for their degradation; examples include the destruction of cyclins in cell cycle control (Glotzer et al., 1991) and degradation of proteins that regulate development, e.g., the vertebrate c-mos protein kinase (Okazaki et al., 1992) or the yeast MATα2 transcription factor (Hockstrasser et al., 1991; Chen et al., 1993). The ubiquitin system is essential for phenomena as diverse as the heat shock response and DNA repair, and both ubiquitin and the enzymes involved in ubiquitin metabolism are highly conserved among eukaryotic phyla (Finley and Chau, 1991; Hershko and Ciechanover, 1992; Hockstrasser et al., 1992; Jentsch, 1992; Varshavsky, 1992). Using a MATα2 derivative as substrate, we previously identified a ubiquitin-dependent degradation pathway in the yeast Saccharomyces cerevisiae, the DOA (degradation of alpha) pathway (Chen et al., 1993; Hochstrasser & Varshavsky, 1990). This pathway, which requires two ubiquitin-conjugating (Ubc) enzymes, Ubc6 (Doa2) and Ubc7, targets α2 via an element within the first 67 residues of the α2 repressor, the Deg1 degradation signal. Many more gene products have been implicated in α2 degradation, based on genetic analyses (Chen et al., 1993).

Ubiquitin is a 76 amino acid residue protein that is either free or covalently joined, through its carboxyl-terminal glycine residue, to various cytoplasmic, nuclear, and integral membrane proteins. The attachment of ubiquitin to proteins is catalyzed by ubiquitin-conjugating enzymes (also called E2 enzymes). Ubiquitin is conserved among eukaryotes to an extent unparalled among known proteins.

Ubiquitin is one of several factors required for ATP-dependent protein degradation in eukaryotic cells. Intracellular protein degradation serves to selectively eliminate damaged and otherwise abnormal proteins and to confer short half-lives on undamaged proteins whose concentrations in the cell must vary as functions of time (e.g., regulatory proteins). Many long-lived protein components of larger macromolecular complexes such as ribosomes and oligomeric proteins are metabolically unstable in a free, unassociated state.

Selective degradation of many short-lived proteins requires a preliminary step of ubiquitin conjugation to a targeted proteolytic substrate. Ubiquitin likely servea as a signal for attack by proteases specific for ubiquitin-protein conjugates (reviewed by Finley and Varshavsky, *Trends Biochem. Sci.* 10:343–348 (1985)).

At least some short-lived proteins are recognized as targets for proteolysis because they contain sequences (degradation signals) which make these proteins substrates of specific proteolytic pathways. The first degradation signal to be understood in some detail comprises two distinct determinants: the protein's amino-terminal residue and a specific interval lysine residue (Bachmair et al., Science 243:179–186 (1986)); Bachmair and Varshavsky, Cell 56:1013–1032 (1989)). The N-end rule is a code, that relates the protein's metabolic stability to the identity of its amino-terminal residue (Bachmair et al., Science 234:179 (1986)), is universal in that different versions of the N-end rule operate in all of the eukaryotic organisms examined, from yeast to mammals (Gonda et al., *J. Bol. Chem* 264:16700 (1989)).

The second essential determinant of the N-end rule based degradation signal, referred to as the second determinant, is a specific internal lysine residue in the substrate protein that serves as the site of attachment of a multiubiquitin chain. Formation of the multiubiquitin chain on a targeted short-lived protein is essential for the protein's subsequent degradation.

U.S. Pat. No. 5,122,463 discloses methods and compositions for metabolically destabilizing a protein or peptide of interest (i.e., targeting a protein or peptide for degradation) that contains a second determinant of the N-end rule-based degradation signal. The disclosed method involves contacting the protein or peptide of interest with a targeting protein or peptide which interacts specifically with the protein or peptide of interest. The targeting peptide or protein is characterized as having a destabilized amino-terminal amino acid according to the N=-end rule of protein degradation, but lacking a second determinant of the N-end rule-based degradation signal.

The protein or peptide of interest and the targeting peptide or protein are preferably subunits or portions of subunits of the same oligomeric protein in a living cell. The cell is transformed with an expressible DNA construct encoding a targeting peptide or protein having a destabilizing amino-terminal amino acid according to the N-end rule of protein degradation, but lacking a second determinant of the N-end rule-based degradation signal.

One method for generating a targeting peptide or protein having a destabilizing amino-terminal amino acid residue is to transform a eukaryotic cell with an expressible DNA construct comprising ubiquitin fused in frame to a DNA sequence encoding a peptide or protein which interacts specifically with the protein or peptide of interest.

A requirement of the method is that it is necessary to identify a peptide or protein which interacts specifically with the protein or peptide of interest. Because nearly all proteins specifically interact with other proteins, this is broadly applicable methods for metabolically destabilizing a protein or polypeptide of interest.

Regulating protein degradation by regulating protein deubiquitination can be stimulating or inhibiting degradation. Where protein degradation is to be stimulated a protein whose degradation is ubiquitin-dependent is exposed to a deubiquitinating enzyme of the present invention.

Where protein degradation is to be inhibited, a protein whose degradation is ubiquitin-dependent is exposed to a mutant deubiquitinating enzyme of the present invention, which mutant does not catalyze the deubiquitination of proteins. Deubiquitinating proteins and routants thereof are described in detail hereinafter in the Examples.

Exposing can be accomplished in vitro or in vivo. In vitro deubiquitinating processes have application in the industrial bulk production of proteins such as enzymes. A deubiquitinating enzyme of the present invention can be used in such processes to remove ubiquitin from the produced protein or to direct the removal of selected terminal amino acid residues. The use of deubiquitinating enzymes for generating desired amino-terminal residues of proteins is described in U.S. Pat. No. 5,093,242, the disclosure of which is incorporated herein by reference.

Where exposing is accomplished in vivo, cells lacking an endogenous deubiquitinating system or cells having a mutation or deficiency in a deubiquitinating enzyme are transfected with a polynucleotide comprising a DNA sequence that encodes a deubiquitinating enzyme. Examples 1–5, hereinafter, describe in detail the use of such transfection processes in regulating the removal of ubiquitin or ubiquitin fragments from proteins. Alternatively, a cell can be transfected with an expression vector comprising a DNA sequence that encodes a mutant deubiquitinating enzyme (e.g., DOA4$^{SER571}$) such that the natural protein degradation pathway for a protein is inhibited. Examples of the use of such a mutant deubiquitinating enzyme is described in detail hereinafter in the Examples.

Processes for destabilizing proteins in vivo, producing proteins using ubiquitin fusion and the in vitro cleavage of ubiquitin fusion proteins are well known in the art. Descriptions of such processess can be found in U.S. Pat. Nos. 5,122,463, 5,132,213 and 5,196,321, the disclosures of which are incorporated herein by reference. In addition, the nucleotide and amino acid residue sequences of ubiquitin-specific proteases can be found in U.S. Pat. No. 5,212,058, the disclosure of which is incorporated herein by reference. A deubiquitinating enzyme of the present invention differs from those proteases.

EXAMPLES

Examples have been included to illustrate preferred modes of the invention. Certain aspects of the following examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the following examples are intended to be exemplary only and that numerous changes, modifications and alterations can be employed without departing from the spirit and scope of the invention.

Example 1

The yeast DOA4 gene encodes a deubiquitinating enzyme

The DOA4 gene was isolated by its ability to restore degradation of a MATα2-b-galactosidase fusion protein, Deg1-bgal, in the degradation-defective doa4-1 mutant(Hochstrasser & Varshavsky, 1990) (FIG. 1a). The DOA4 gene was cloned from a yeast genomic library (Rose et al., 1987) by complementation of doa4-1 mutant MH11D5–8a (see FIG. 4). Fragments from plasmid pDOA4-1, which contained the smallest complementing DNA insert, were subcloned into YCplac33 (Geitz & Sugino, 1988). Complementing activity was localized to a 5.4 kb KpnI-PstI fragment (plasmid pDOA4-8). That the complementing gene was indeed DOA4 was verified by showing close linkage of an integrated fragment of the cloned DNA, marked with URA3, and the original doa4-1 mutation (12 tetrads, all parental ditypes).

DNA was sequenced on both strands (Ausubel et al., 1989). Although 24 dA residues in the poly(dA) tract are shown, the number sequenced ranged between 23 and 25 in different M13 subclones. The DNA sequence of DOA4 has been deposited in GenBank (accession no. U02518). The codon adaptation index (Sharp & Li, 1987) of DOA4 is 0.154, which is within the range expected of weakly expressed yeast genes. Recently, an unpublished yeast sequence, SSV7, has appeared in the GenBank database (L08070) that encodes a protein 97% identical to Doa4. The two genes are likely to be the same, with differences due to SSV7 sequencing errors or polymorphisms. The 5' sequence of the pDOA4-1 insert matched a region of the TPS2 gene on chromosome IV (1.6 kb overlap) (De Virgilio et al., 1993).

The nucleotide sequence of the complementing region of the cloned DNA (FIG. 1b) has a single long potential open reading frame (ORF), which would encode a 926-residue (Mr 105K) protein. A search of the sequence databases revealed two short regions of similarity between Doa4 and three ubiquitin-specific processing enzymes from yeast, Ubp1-Ubp3 (Baker et al., 1992; Miller, 1989; Tobias & Varshavsky, 1992) (FIG. 2d, e). These proteins had been identified on the basis of their ability to cleave ubiquitin from linear ubiquitin-protein fusions, including natural ubiquitin precursors. The Ubp1-Ubp3 enzymes are dissimilar to each other except in the; two stretches also shared by Doa4.

FIG. 2b shows the open reading frames of the yeast DOA4 and human tre-2 (Nakamura, 1992) genes, the latter predicted from two cDNA clones, which differ by two segments present in the TRE213 clone: but absent from TRE210 (boxes in cDNA; indents in TRE210/ORF1). The Cys (stippled) and His (hatched) domains are highlighted. FIG. 2c shows the sequence conservation between two long elements in Doa4 and tre-2 (TRE213/ORF2). The more amino-terminal region, Block 1 (39% identity/60% similarity (Dayhoff et al., 1988)), includes the Cys domain (FIG. 2d); the smaller element is called Block 2 (43%/61%). A third region, Block 3, is referred to as the His domain (FIG. 2e). Weaker sequence similarities between various family members was observed in Blocks 1 and 2, e.g.,the region corresponding to residues 656–675 of Doa4. FIGS. 2d and e show conserved elements in Doa4 and other deubiquitinating enzymes around the presumptive active site Cys and His residues (arrowheads), including consensus sequences ($\geq 4$ identities). Residues are boxed if present in at least three of the proteins or, in the case of small uncharged (n) or hydrophobic (h) residues, share the indicated property in at least six of the proteins.

Sequences compared to Doa4 are yeast Ubp1-Ubp3 (Baker et al., 1992; Tobia & Varshavsky, 1991); mouse Unp (Gupta et al., 1993); human tre-2 (TRE213/ORF2)(Nakamuar, 1992); and Drosophila fat facets (faf) (Fischer-Vize et al., 1992) (a 22-residue segment was deleted after residue 2029 of faf). Sequences were aligned initially with PILEUP. Many partial cDNA sequences in the GenBank database, identified with BLAST (Altschul et al., 1990), also show significant similarity to regions within Blocks 1–3; these include human (T04867, T09031, Z12710, Z15701, Z21167), *Caenorhabditis elegans* (M80041, Z14720, Z14811), *Arabidopsis thaliani* (Z17750, Z25610), and canine (L03387) sequences.

To determine whether Doa4 has protein deubiquitinating activity, the DOA4 gene and a gene encoding Ub-Met-bgal, in which ubiquitin is fused to the amino-terminus of bgal (Varshavsky, 1992), were coexpressed in *E. coli* (which lacks a ubiquitin system). Ub-Met-bgal and Ub-Leu-bgal were expressed from pACYC184-based plasmids. Plasmid-bearing *E. coli* MC1061 cells were subjected to anti-bgal (Cappel) immunoblot analysis. As shown by immunoblot analysis (FIG. 3a), Doa4 cleaved Ub-Met-bgal to Met-bgal (lane 3) to an extent comparable to that observed with Ubp 1 (lane 2). When the Met residue in Ub-Met-bgal was replaced by Leu, cleavage was unaffected, but very little Leu-bgal product accumulated (FIG. 3a, lane 6), as predicted if the Doa4-catalyzed scission occurred precisely at the junction between ubiquitin and Leu-bgal because Leu-bgal, unlike Met-bgal, is rapidly degraded in *E. coli* (Varshavsky, 1992).

Deubiquitinating enzymes have properties of thiol proteases (Rose, 1988). The sequence elements shown in FIG. 2d,e include absolutely conserved Cys and His residues. The codon for Cys$^{571}$ of Doa4 was changed to a Ser or Ala codon, and the resulting Doa4 mutants, and the corresponding GST-Doa4 fusion proteins, were tested for deubiquitinating activity. The doa4$^{Ala571}$ and doa4$^{Ser571}$ alleles were constructed by oligonucleotide-directed mutagenesis (Ausubel et al., 1990). GST fusions were made by amplification of DOA4 or tre-2 sequences by PCR (done in duplicate) and insertion into pGEX-KG (Ausubel et al., 1990) downstream of the glutathione-S-transferase (GST) coding element.

Figure 3A:
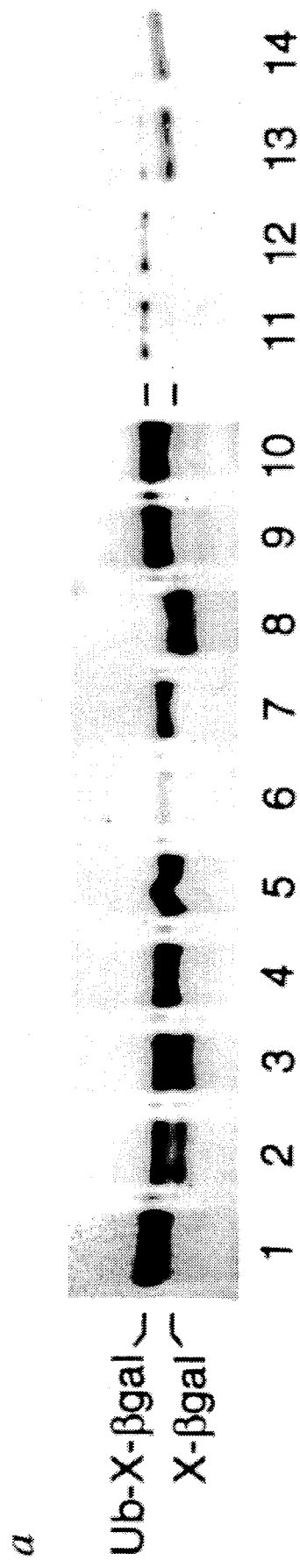
FIGS. 3a–3d show deubiquitination reactions catalyzed by Doa4 and tre-2.
Figure 3B:
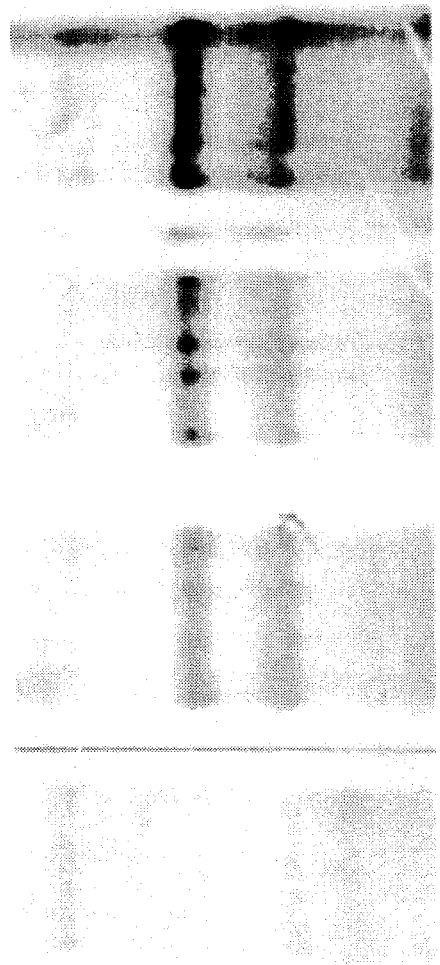
Figure 3C:
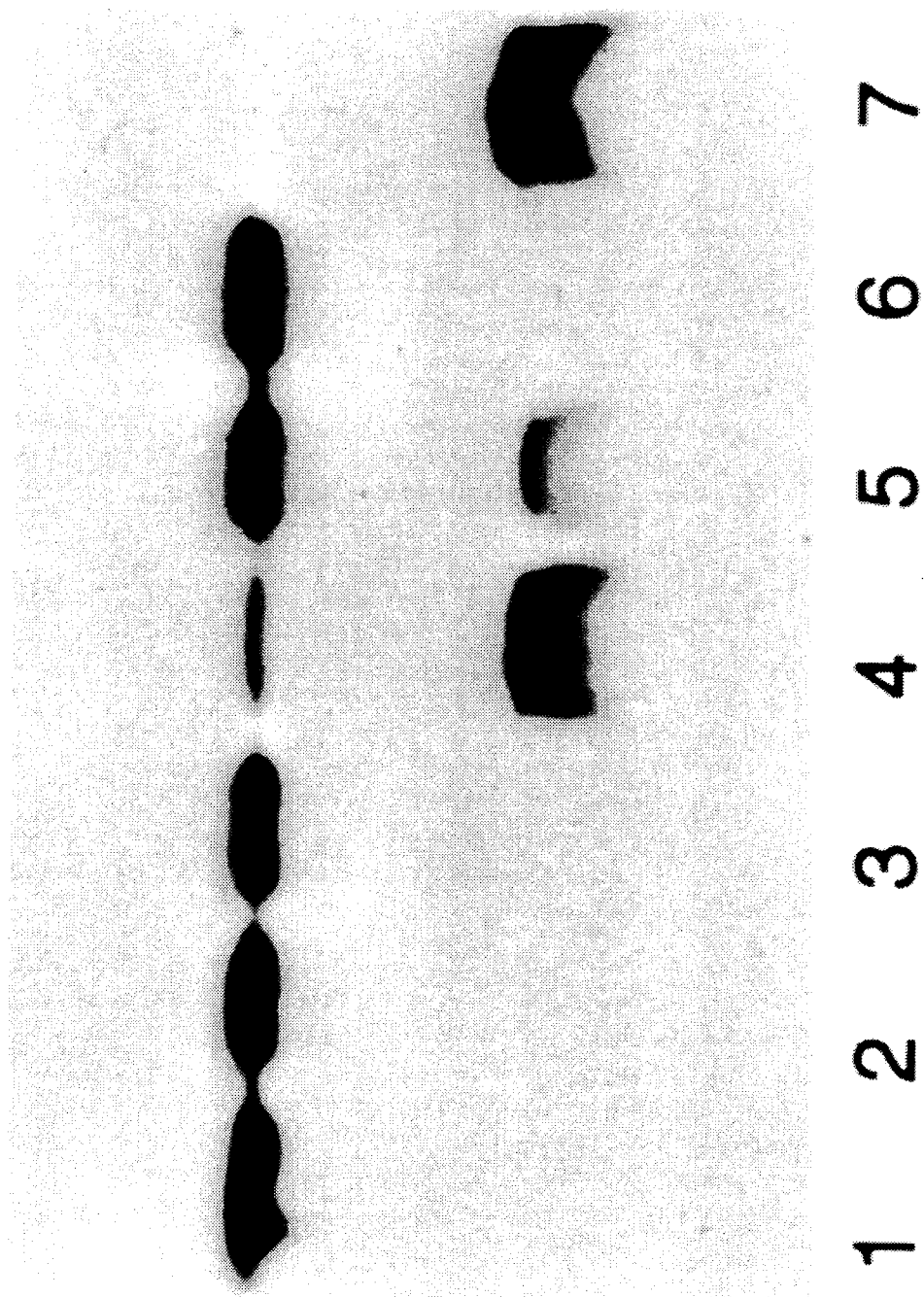
Figure 3D:
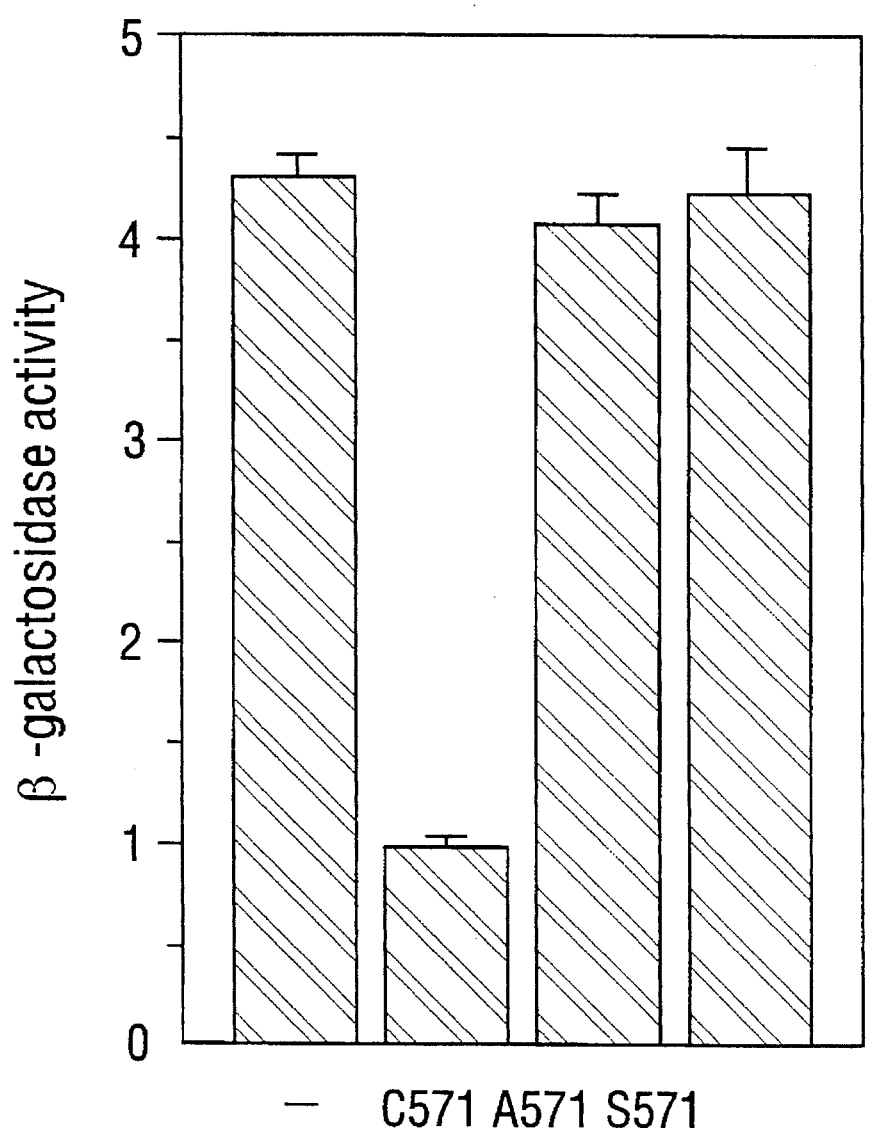

The doa4$^{Ser571}$ and doa4$^{Ala571}$ proteins, as well as their GST derivatives, were unable to process the Ub-Met-bgal substrate (FIG. 3a, lanes 4–5, 9–10). Moreover, neither doa4$^{Ser571}$ nor doa4$^{Ala571}$ was functional in yeast cells (FIG. 3d). Thus, Doa4 can specifically cleave ubiquitin from linear ubiquitin-protein fusions, and this activity, as well as Doa4 function in yeast, requires the conserved Cys residue. Doa4$^{Ser571}$ and doa4$^{Ala571}$ also did not deubiquitinate Ub-Leu-bgal, and the level of Ub-Leu-bgal in these experiments was comparable to that of Ub-Met-bgal; the reduction of unprocessed Ub-Leu-bgal in lane 6 may reflect a mass action effect due to Leu-bgal degradation.

Ubiquitin-dependent proteolytic substrates require attachment of an isopeptide-linked multiubiquitin chain for efficient degradation (Chau, 1989). The ability of Doa4 to deubiquitinate a protein with ubiquitin in isopeptide linkage was tested with a ubiquitin-Lys48-ubiquitin dimer (Cook et al., 1992) as substrate, in which the a-carboxyl group of one ubiquitin is attached to the e-amino group of Lys48 in the second ubiquitin (the same linkage found in the multiubiquitin chains formed on proteolytic substrates (Chau, 1989)). Assays of Ub, cleavage were done with GST-Doa4 or GST-tre-2 proteins partially purified from *E. coli* JM101 (Ausubel et al., 1989). Equal amounts of protein were incubated at 37° C. with 60 ng of Ub$_2$$^{22}$ in 50 mM Tris-HCl (pH 7.6), 4 mM DTT. Proteins were detected by anti-ubiquitin (East Acres Biologicals) immunoblot analysis with the ECL system (Amersham). bgal activity was measured as described (Hochstrasser & Varshavsky, 1990).

GST-Doa4 was isolated from *E. coli* and incubated with ubiquitin dimer. The bulk of the dimer molecules were cleaved to free ubiquitin (FIG. 3d, lane 4). That this activity was due to GST-Doa4, rather than a copurifying *E. coli* enzyme, was demonstrated by the inability of GST-doa4 $_{Ser571}$ to cleave the substrate (FIG. 3d, lane 3). Therefore, Doa4 is able to cleave both peptide and isopeptide-linked ubiquitin moieties from substrates.

Example 2

Inhibition of ubiquitin-dependent proteolysis in doa4 mutants

Figure 4A:
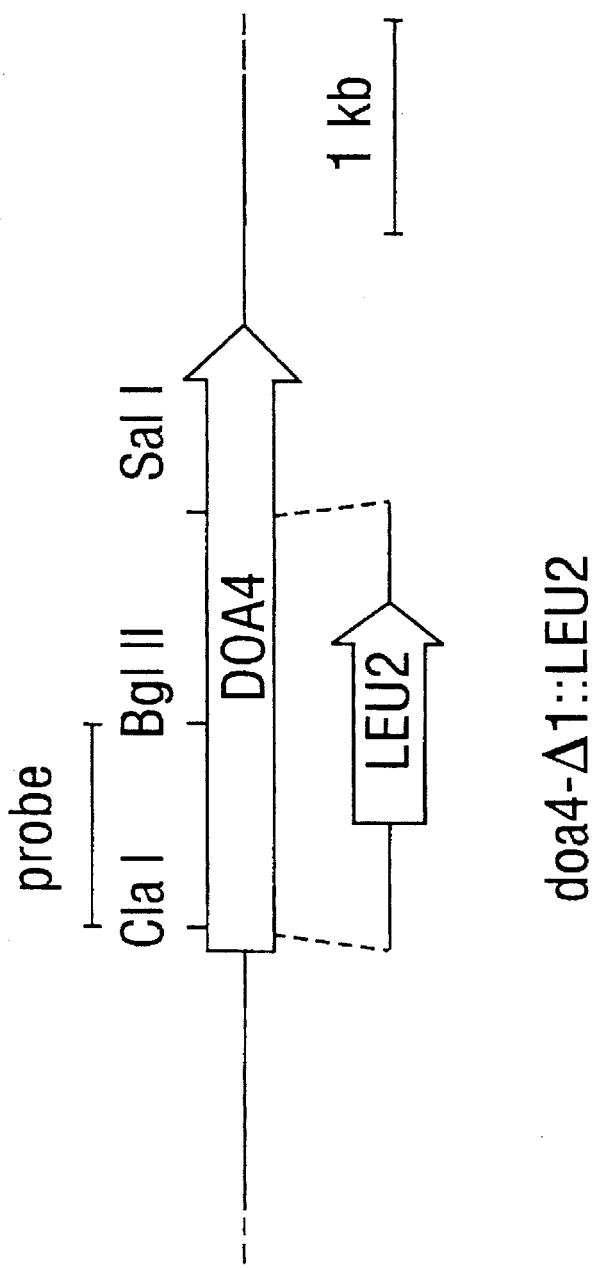

To assess the phenotype of a doa4 null mutant, the DOA4 gene was deleted (FIG. 4a). The following yeast strains were used in this study: wild types DBY1705, MHY102, and MHY501, all described previously (Chen et al., 1993); MHY11D5-8a (MATa doa4-1 lys2-801 ura3-52 leu2-3,112 LEU2::D68-21002-lacZ) and MHY11D5-7b (MATa doa4-1 his3-D200 ade2101 ura3-52 leu2-3,112 LEU2::D68-21002-lacZ), both segregants from a backcross between MHY101 and the original doa4-1 mutant, MHY89 (Hochstrasser & Varshavsky, 1990); the homozygous mutant diploid MHY490 (MH11D5-7b×MH11D5-8a); wild-type diploid strains MHY105 (MHY101×MHY102) and MHY606 (MHY501×MHY500 (Chen et al., 1993)); and two haploid doa4-D1 routants, MHY622 (MATa) and MHY623 (MATa). To make doa4-D1::LEU2, the ClaI-SalI fragment of DOA4 was replaced with a 2.2 kb SmaI-SalI LEU2 fragment. This allele was introduced into MHY606, and haploid doa4-D1::LEU2 segregants were identified; correct integration was confirmed by DNA hybridization analysis. RNA levels were examined by Northern blotting (Ausubel et al., 1989); slight differences in DOA4 mRNA migration are artifactual, due apparently to the nearly comigrating 25S rRNA. Exponentially growing cells cultured in minimal media at 30° C. were used unless otherwise noted. The actin probe was a 0.28 kb ClaI-BglII fragment from ACT1 (Gallwitz & Sures, 1980). Growth measurements were carried out in minimal media. For the heat stress experiments, colony formation on YPD plates was scored after 3 d at 38.5° C. Hypersensitivity to Cd$^{2+}$ was determined after 5 days at 30° C. Hypersensitivity to 0.4 mg/ml canavanine sulfate was determined by growing cells in minimal medium and plating equal volumes of cells on control plates and plates containing the arginine analog. Ultraviolet (uv) sensitivity was quantitated using a uv cross-linker (Hoefer) set at 10 mJ/cm (Okazaki et al., 1992), O-ray sensitivity by exposing cells to a Co$^{60}$ source (1500 Gy). In both cases, doa4 cells were ~10-fold more sensitive than wild-type. pDOA4-8 fully complemented the doa4 slow growth and sporulation defects.

Figure 4B:
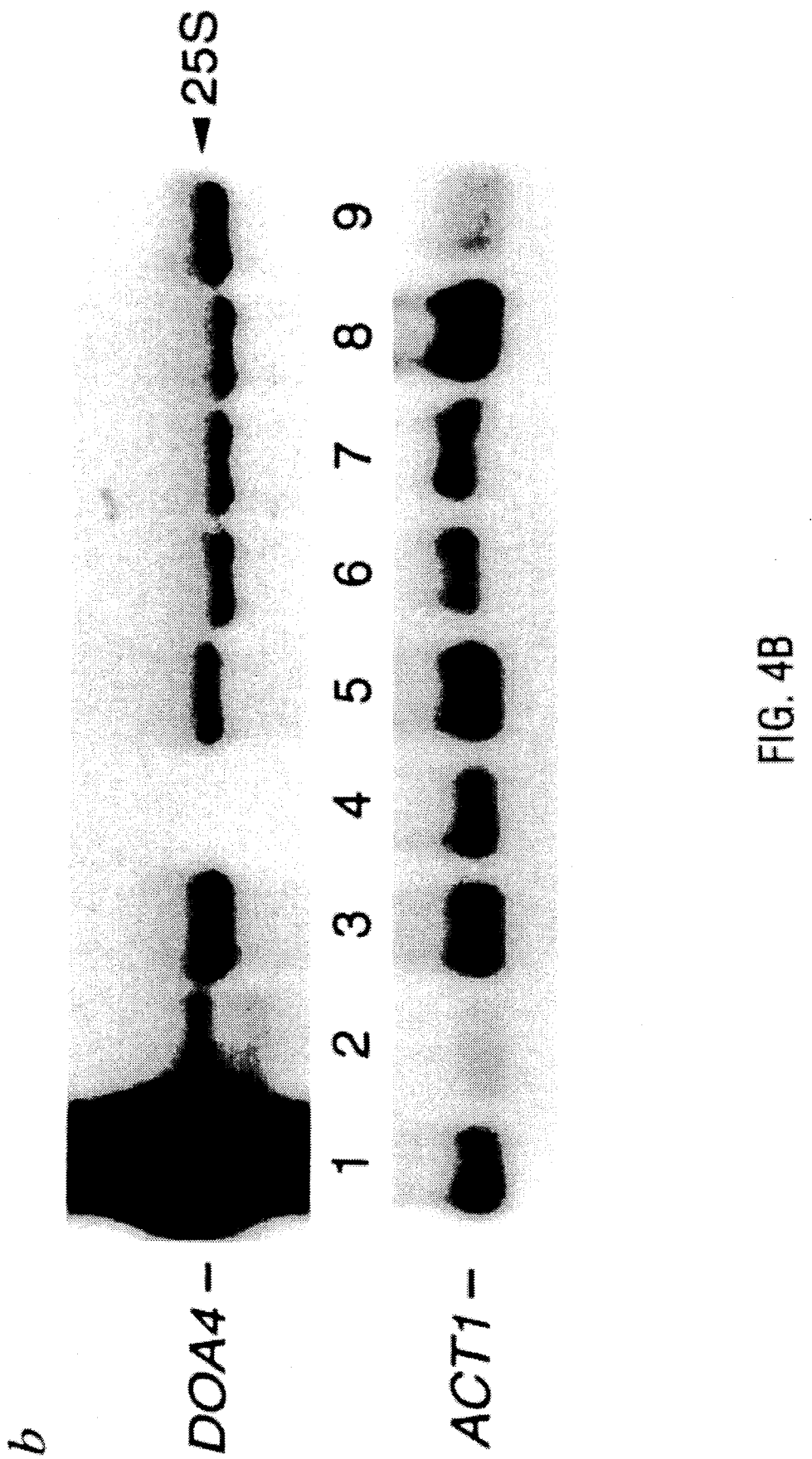

Phenotypically, doa4D cells were indistinguishable from the original doa4-1 mutant. Doa4- cells had multiple defects, with aberrations ranging from slow growth to a defect in DNA repair (based on sensitivity to uv or g radiation) (FIG. 4c). Hence, the Doa4 deubiquitinating enzyme is required in diverse physiological processes. On the other hand, the only condition that appeared to increase DOA4 transcript levels was entry into stationary phase (FIG. 4b). Expression of several other ubiquitin system genes is elevated in stationary phase (Finley & Chau, 1991).

Figure 5A:
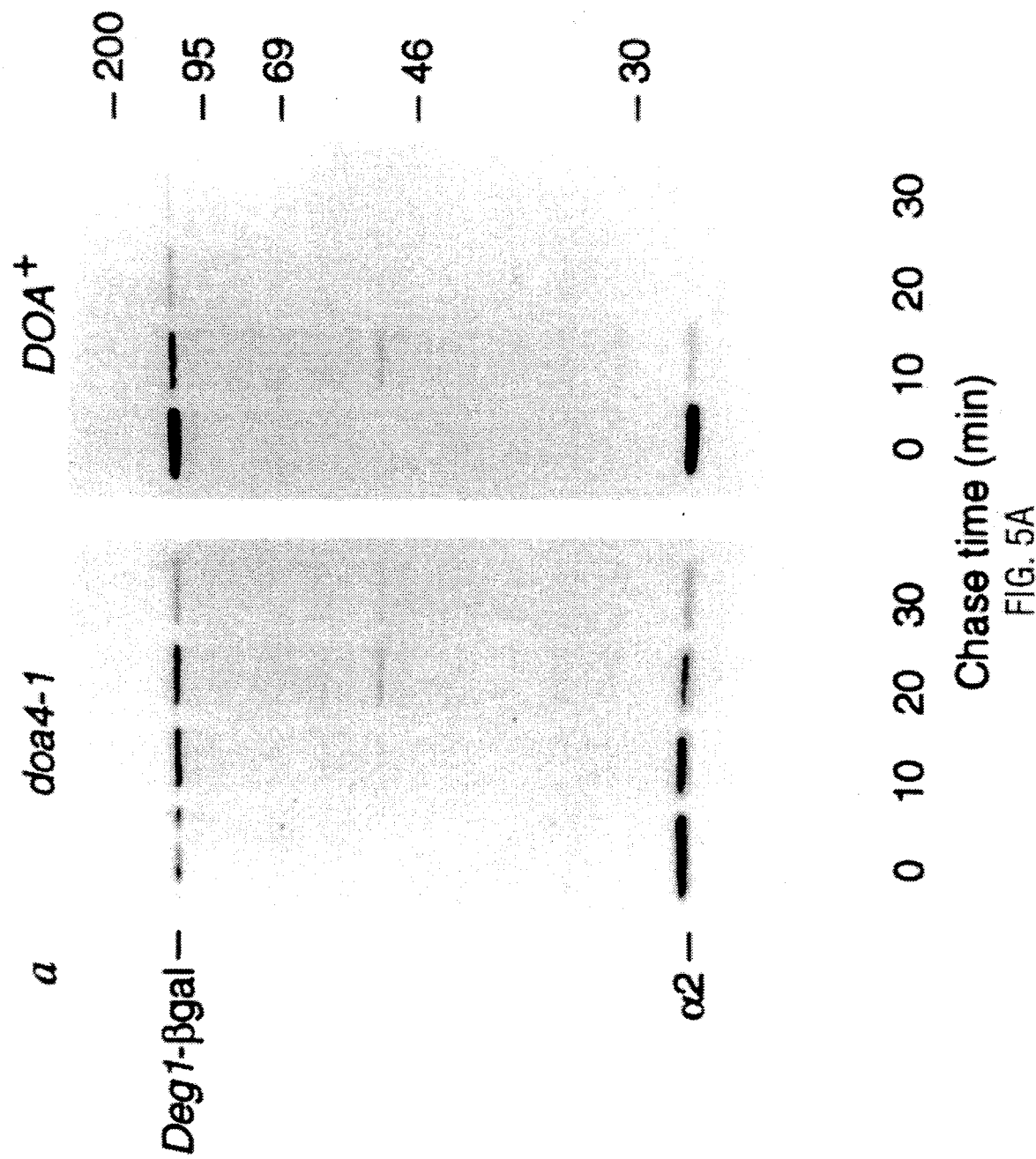
FIGS. 5a and 5f show doa4 routants are impaired in the degradation of multiple ubiquitin-dependent substrates in vivo.
Figure 5B:
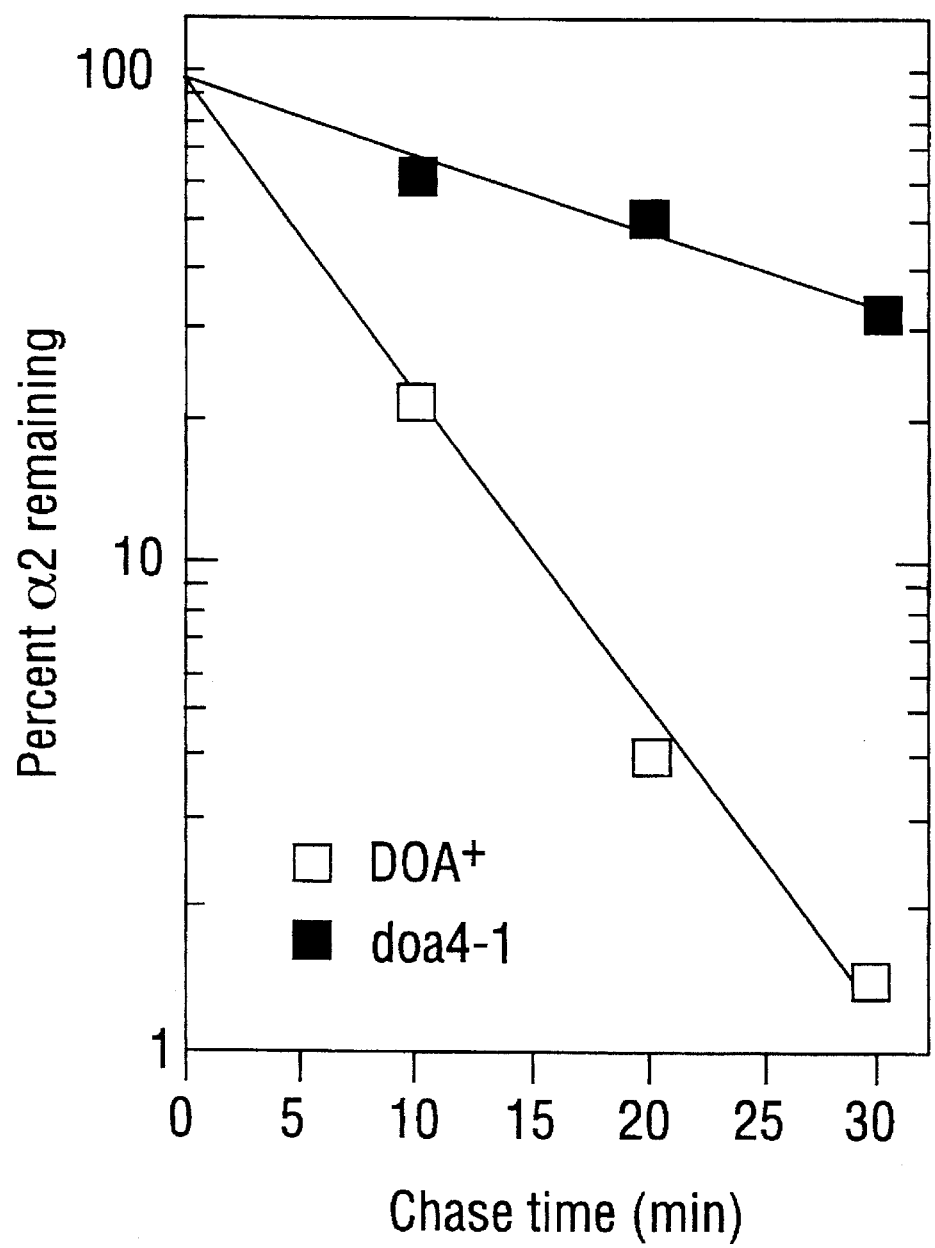
FIG. 5b shows the quantitation of α2 turnover in DOA$^+$ and doa4-1 cells. The half-life of α2 was 4.7 min in DOA$^+$ and 19 min in doa4-1 cells.
Figure 5C:
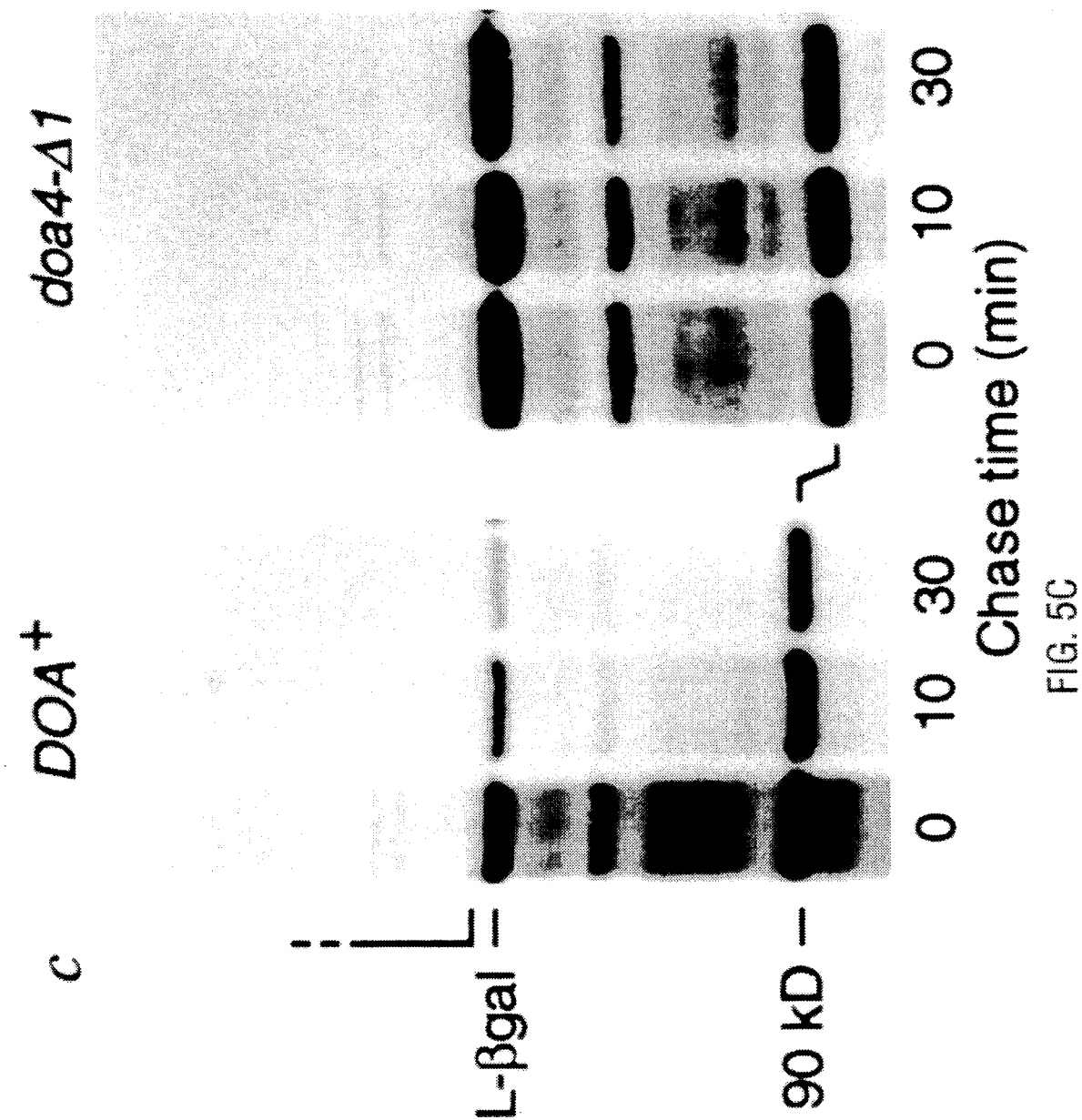
FIG. 5c shows the degradation of Leubgal, an N-end rule substrate, in doa4D (MHY623) and DOA$^+$ (MHY501) cells. The open-ended bracket marks the positions of multiubiquitin-Leubgal conjugates. 90 kD, a cleavage product derived from bgal (Bachmair et al., 1986). Reduced amounts of the Mr 90K product were generated from Leu-bgal and especially from Ub-Pro-bgal in doa4 cells. An anti-bgal antibody (Cappel) was used for immunoprecipitation.
Figure 5D:
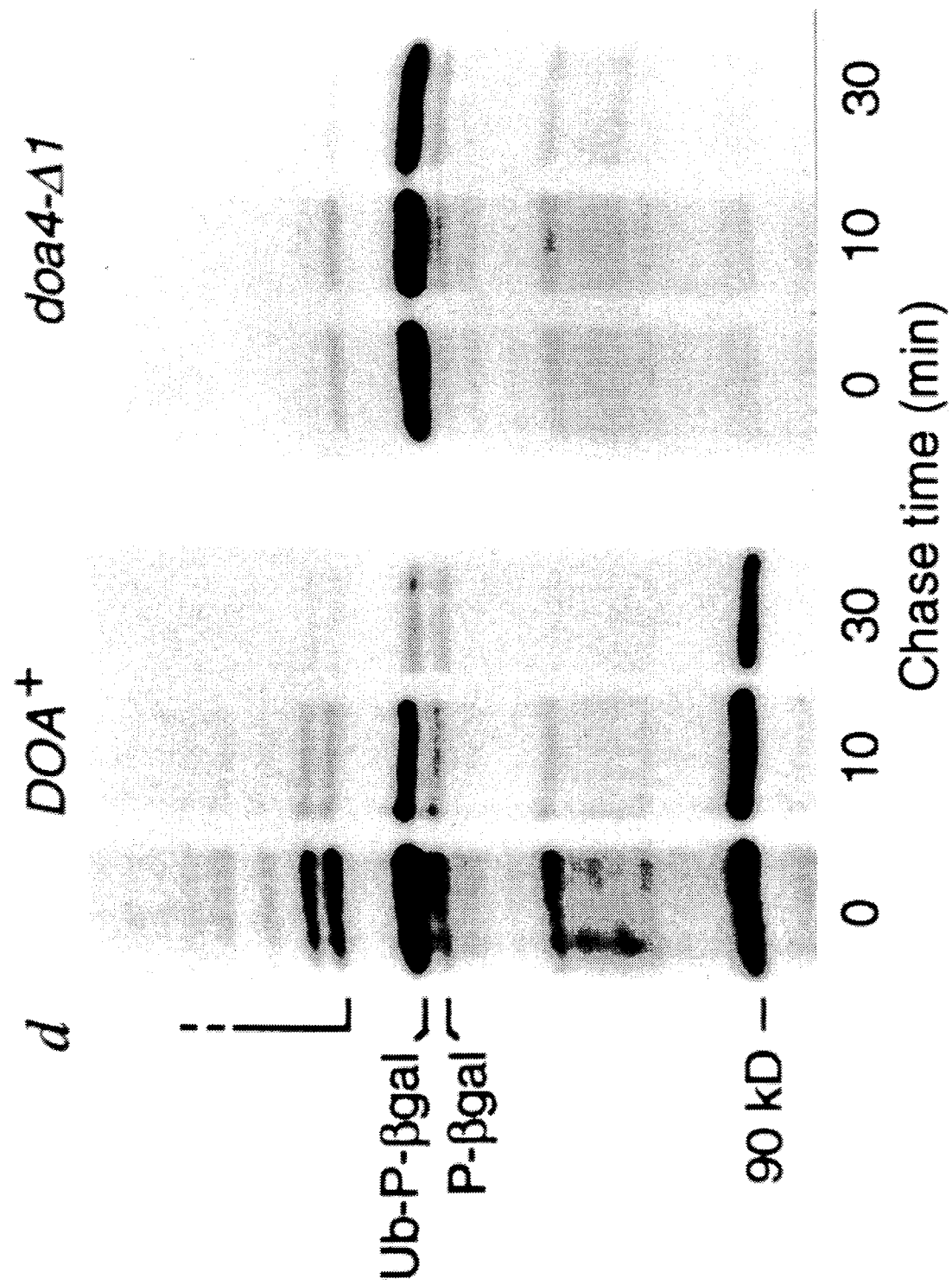
FIG. 5d showsss the degradation of Ub-Pro-bgal in MHY623 and MHY501 cells.
Figure 5F:
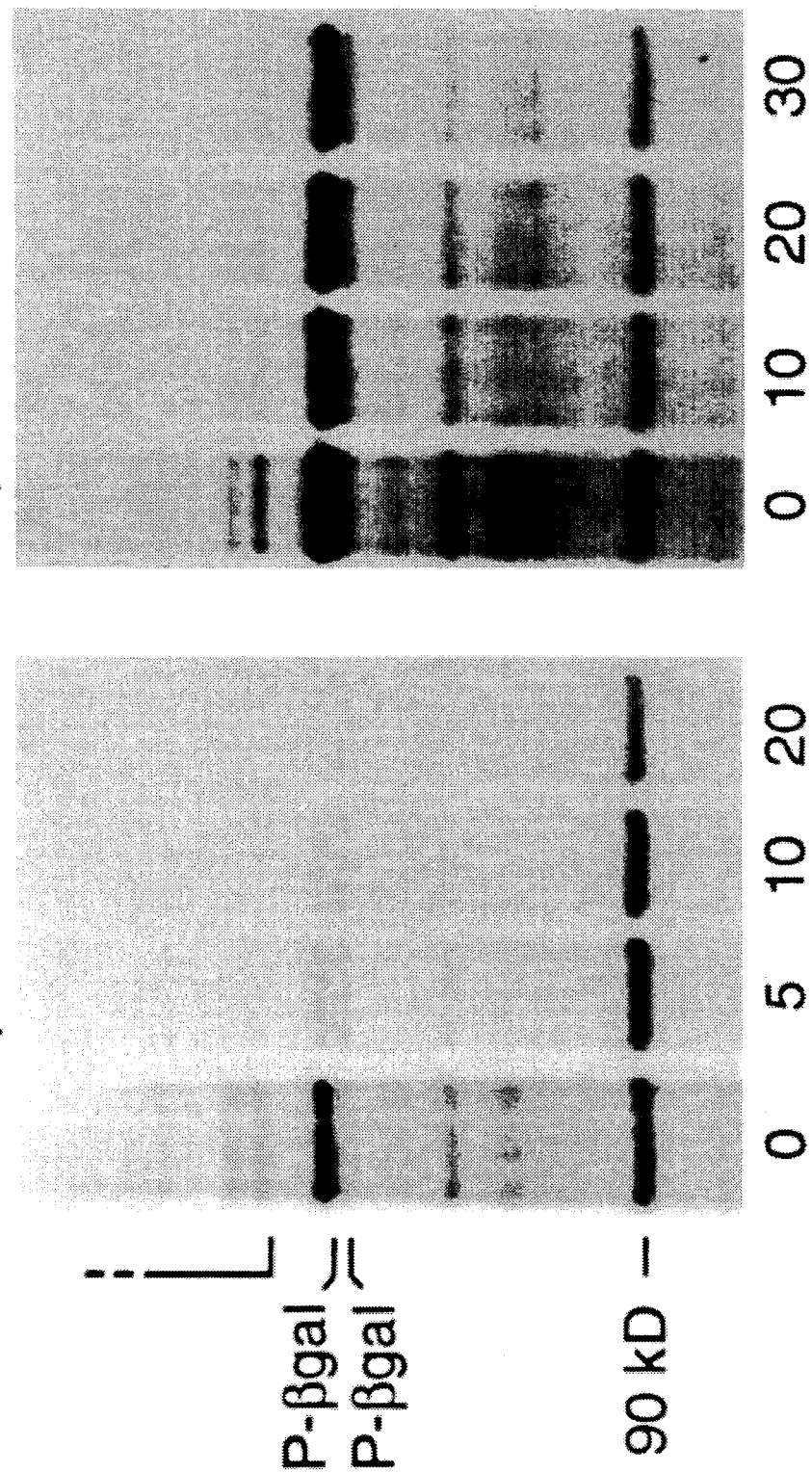

The abnormalities of doa4 cells may reflect defects in ubiquit-independent proteolysis inasmuch as mutations in UBC or proteasomal genes result in many of the same defects (Jentsch, 1992). FIG. 5a,b shows the defect of the doa4-1 mutant in the degradation of Deg1-bgal and of intact α2 repressor. Inactivation of Doa4 resulted in a 4 to 5-fold increase in the half-life of α2 at 30° C. (FIG. 5b), while Deg1-bgal degradation was inhibited at least 10-fold relative to wild-type cells (FIG. 5a). Two well-characterized classes of artificial substrates of the ubiquitin-dependent proteolytic system in yeast have been described (Varshavsky, 1992). One class, the N-end rule substrates, requires Ubc2 for multiubiquitination, while the other, represented by the Ub-Pro-bgal protein, depends on a distinct Ubc enzyme, Ubc4. Degradation of Leu-bgal, an N-end rule substrate, and Ub-Pro-bgal was inhibited ~10-fold and ~20-fold, respectively, in the doa4D mutant (FIG. 5c, d). Multiubiquitinated forms of both Leu-bgal and Ub-Pro-bgal were present at reduced levels in doa4D cells relative to wild-type. Based on the strong inhibitory effects on the turnover of these substrates, which are subject to distinct ubiquitination mechanisms, we conclude that Doa4 plays a key role in the ubiquitin-dependent protein degradation system of *S. cerevisiae*.

If Doa4 functioned in vivo to deubiquitinate proteins prior to their targeting to the 26S proteasome, raising intracellular levels of Doa4 might also be expected to inhibit substrate proteolysis. Overexpression of Ubp2, for instance, inhibits Ub-Pro-bgal degradation (Baker et al., 1992). DOA4 was subcloned into a high copy 2m-based plasmid that was introduced into wild-type yeast cells. Pulse-chase analysis was done as described (Chen et al., 1993; Hochstrasser & Varshavsky, 1990). The KpnI-PstI fragments from pDOA4-8 and pDOA4-8$^{Ser571}$ were subcloned into either YEplac195 (Gietz & Sugino, 1988) or pRS424 (Christianson et al., 1992). To verify that the dominant-negative effect of doa4$^{Ser571}$ required expression of doa4$^{Ser571}$ protein, the unique ClaI site (FIG. 1a) was cleaved, and the 2-bp 5'-overhang was filled in with Klenow polymerase. Religation created an NruI site and resulted in a frameshift after codon 56 of doa4$^{Ser571}$. Ub-Pro-bgal degradation in (f) was measured in MHY612 cells. MHY612 (P. Chen and M.H., unpublished) bears a rad6D::LEU2 allele (Dohmen et al., 1991) in a strain otherwise isogenic with MHY501.

Levels of DOA4 mRNA in these cells were increased at least 20-fold above normal (FIG. 4b, lanes 1,2). Surprisingly, elevated expression of Doa4 accelerated, rather than inhibited, Deg1-bgal and α2 degradation (FIG. 5e). The turnover of α2 increased ~30–40% relative to cells bearing only the control plasmid (FIG. 5e). Under certain conditions, Ub-Pro-bgal turnover was also increased slightly by overproduction of Doa4 (data not shown). Thus, intracellular levels of Doa4 can be at least partially rate-limiting for ubiquitin-dependent protein degradation.

Example 3

A dominant-negative mutation in DOA4

Expression of the Doa4 active site mutant, doa4$^{Ser571}$ (FIG. 2), from a high-copy plasmid in wild-type cells inhibited degradation of all ubiquit-independent substrates tested (FIG. 5e,f). Overproduction of doa4$^{Ser571}$ also lead to cellular defects comparable to those resulting from deletion of DOA4, such as slower growth. High-copy doa4$^{Ser571}$ expression resulted in a ~30% increase in the doubling time of wild-type MHY 102 cells in minimal medium. That these abnormalities resulted from expression of doa4$^{Ser571}$ protein (rather than competition of the high-copy doa4$^{Ser571}$ gene or mRNA for a factor(s) required for expression of endogenous DOA4) was ascertained by inserting two extra nucleotides near the 5'-end of the doa4$^{Ser571}$ ORF (FIG. 3 legend). The resulting frameshift mutation completely eliminated the defect associated with high copy expression of doa4$^{Ser571}$.

Thus, the dominant-negative defect of doa4$^{Ser571}$ likely resulted from high level expression of a catalytically inactive protein. This could be explained as either a titration of substrate by the inactive protein, formation of an inactive Doa4 heteromer, or competition with normal Doa4 for binding to a component(s) of the proteolytic machinery, perhaps the 26S protease itself. The first possibility seems improbable given the abundance of ubiquitin pathway substrates in vivo and the fact that doa4$^{Ser571}$-substrate interactions would be self-limiting.

Example 4

The doa4 mutant is defective in the metabolism of ubiquitin conjugates in vivo

Figure 6A:
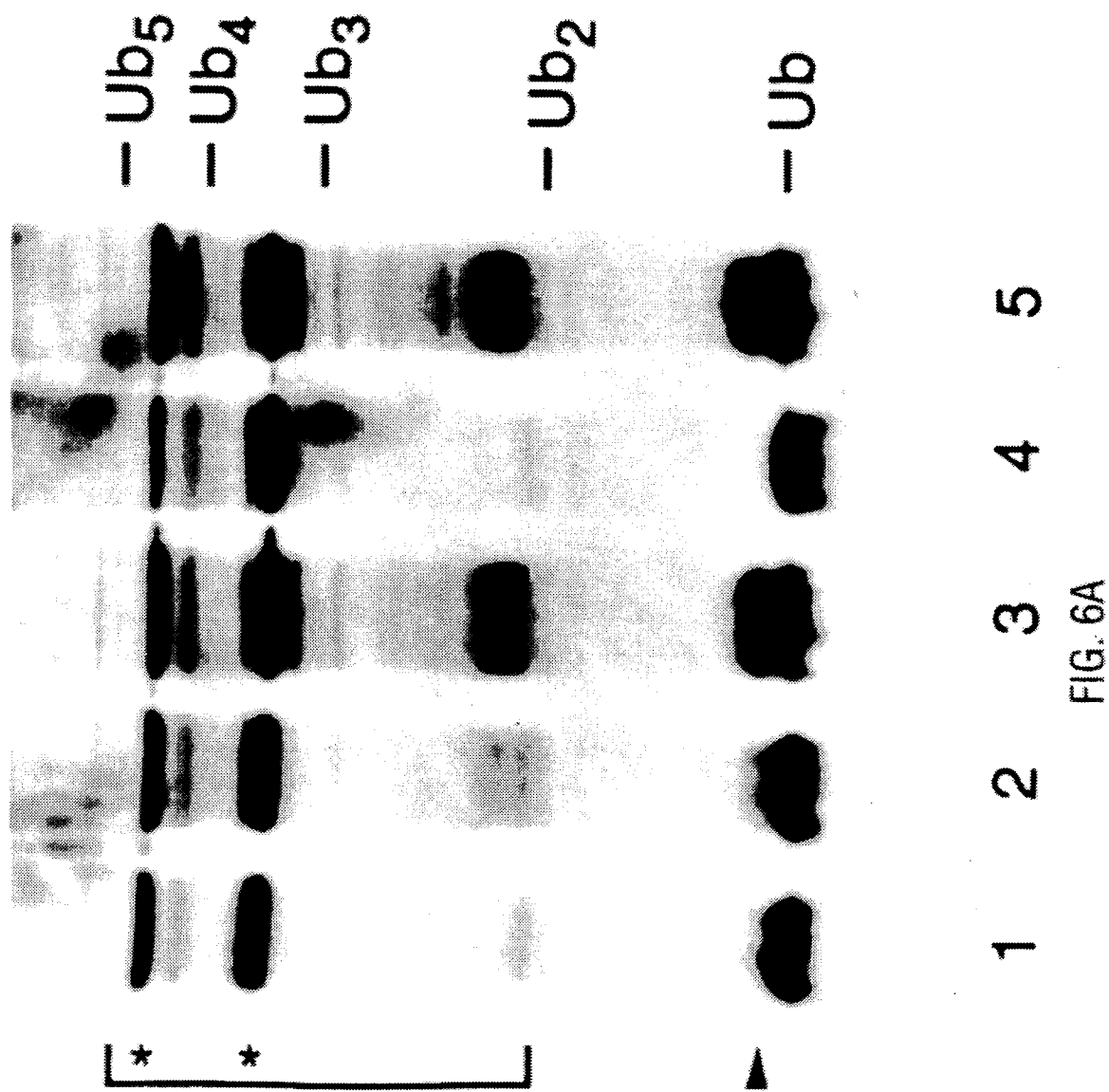
FIGS. 6a and 6b show analysis of Doa4 and a model of its action.
Figure 6B:
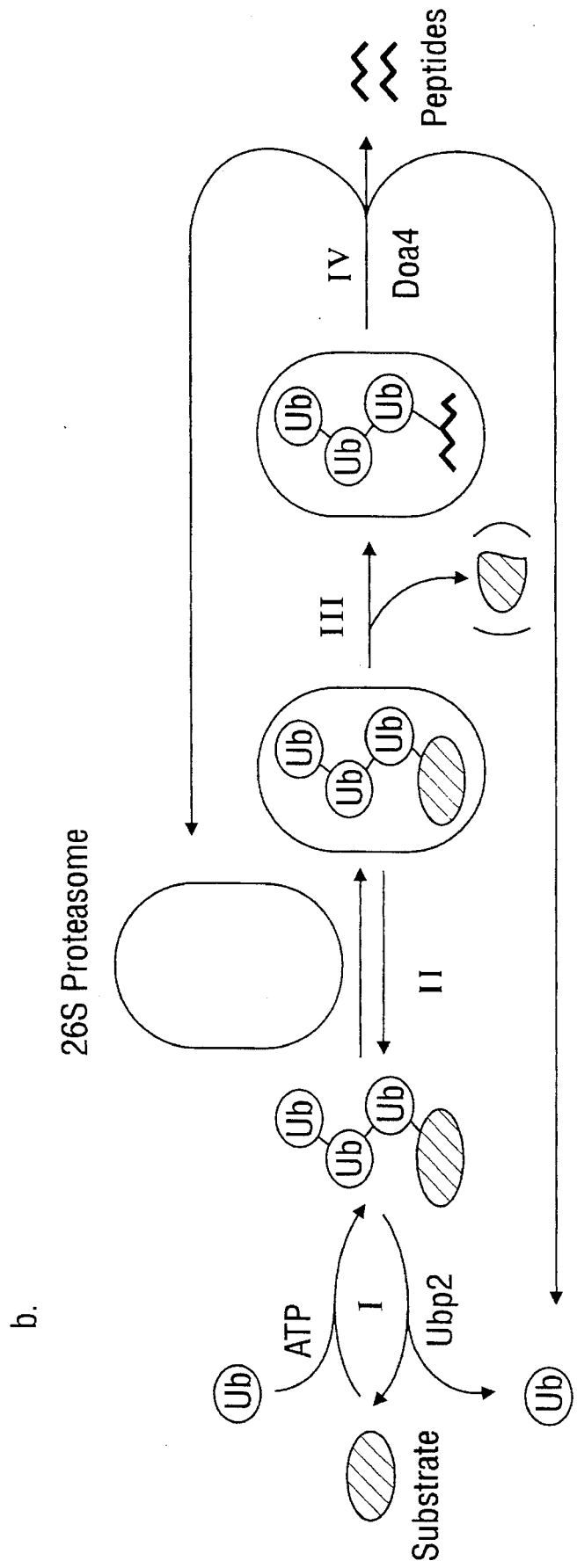

To gain insight into the mechanistic role(s) of the Doa4 enzyme in ubiquitin-depen-dent proteolysis, we examined intracellular ubiquitin and ubiquitin-protein conjugates by anti-ubiquitin immunoblot analysis (FIG. 6a). Exponentially growing cells in minimal media (10 ml) were harvested by centrifugation. Cells were disrupted by incubation in 50 ml of SDS loading buffer (Ausubel et al., 1989) at 100° C. for 10 min. Debris was cleared by centrifugation. ~10% of each supernatant (volumes were normalized to cell densities) was run on an 18% SDS-polyacrylamide gel; proteins were blotted onto PVDF. Ubiquitin-containing proteins were detected with an antiubiquitin antibody (East Acres Biologicals) and the ECL system. The indicated ubiquitin-containing species were also observed with an independent anti-ubiquitin antiserum (Deveraux et al., 1990). The two proteins marked by asterisks did not react with this antiserum.

Only a small decrease in free ubiquitin levels was observed in doa4-cells when compared to congenic wild-type cells (FIG. 6a, lanes 2–5). Moreover, expression of a ubiquitin gene from a strong promoter, which increases free ubiquitin levels ~100-fold (Ellison & Hochstrasser, 1991), did not compensate for loss of Doa4, as measured by either growth rate or Ub-Pro-bgal degradation (dam not shown). The most striking difference between DOA$^+$ and doa4 cells apparent in FIG. 6a was the accumulation of relatively small ubiquitin-containing species in the mutant (arrowhead and bracket). The smallest of these (arrowhead) was only slightly larger than ubiquitin itself; assuming this is a ubiquitin-oligopeptide conjugate,, the peptide(s) is unlikely to exceed ~8–15 residues based on comparisons with peptide-tagged ubiquitin derivatives (Hochstrasser et al., 1991; Ellison & Hochstrasser, 1992). Similarly, the electrophoretic mobilities of the bracketed ubiquitin-reactive species suggested they may represent small multiubiquitin chains (dimers, trimers, . . .) linked to a heterogeneous set of oligopeptides. Overexpression of Doa4 further reduced the low levels of these ubiquitin species in wild-type cells (FIG. 6a, lanes 1,2), indicating the rate of metabolism of these species was limited by intracellular Doa4 levels.

Example 4

The human tre-2 oncogene also encodes a deubiquitinating enzyme

The strongest similarity between Doa4 and proteins in the current databases was found with a set of proteins predicted to be encoded by a human oncogene, tre-2 (Nakamura, 1992). The tre-2 gene gives rise to at least two alternatively spliced mRNAs, both encoding two ORFs (Nakamura, 1992) (FIG. 2b). The similarity between the yeast and human proteins extends over several sequence blocks that comprise over 300 residues (FIG. 2a,c). Inasmuch as the yeast Ubp1, Ubp2, Ubp3, and Doa4 proteins are dissimilar to each other except in the two short stretches mentioned above, it is striking that the Doa4 and human tre-2 proteins show extensive similarity, suggesting they may represent a functionally distinct class of deubiquitinating enzymes. Recently, a putative mouse protooncoprotein, Unp, has been described (Gupta et al., 1992) that shows strong similarity to tre-2 and Doa-4 as well. Doa4 is also related to a Drosophila protein involved in eye and embryonic development, fat facets (faf) (Fischer-Vize et al., 1992) (FIG. 2). To determine whether the close sequence similarity of DOA4 and tre-2 reflected a similarity in enzymatic function, deubiquitinating activity of several tre-20RFs was measured. A GST-TRE213/ORF2 protein had catalytic activities comparable to Doa4, whereas GST-TRE210/ORF1 was inactive (FIG. 3a, lanes 12, 13; FIG. 3d, lanes 5,6). The lack of enzyme activity of GST-TRE210/ORF1 is consistent with the absence of the highly conserved His domain from this polypeptide (FIG. 2b). The TRE210/ORF1 protein was the only polypeptide found to be tumorigenic when individual ORFs derived from tre-2 were expressed at high levels in nude mice (Nakamura, 1992). Tumorigenicity was suppressed if TRE213/ORF2 was fused to TRE210/ORF1 to cream the long ORF that would be formed in a tre-2 mRNA bearing only the second of the two unique TRE213 segments (FIG. 2b). Correspondingly, we found that this "full-length" promin also had deubiquitinating activity (FIG. 3a, lane 14).

REFERENCES CITED

The references listed below as well as all references cited in the specification are incorporated herein by reference to the extent that: they supplement, explain, provide a background for or teach methodology, techniques and/or compositions employed herein.

Adelman et al. (1983) DNA 2:183.
Akil, H. et al. (1984) Annu. Rev. Neurosci. 7:223.
Attali, B. et al. (1989) J. Neurochem. 52:360.
Benovic et al. (1989) Science 246:235.
Bertin, B. et al. (1992) J. Biol. Chem. 267(12):8200.
Bero, et al. (1988) Mol. Pharmacol. 34:614.
Bertolucci, M. et al. Neurosci, Abstr. 18L1368.
Bolivar et al., (1977) Gene, 2:95.
Boshart et al. (1985) Cell 41:521.
Bouvier, M. et al. (1988) Mol. Pharmacol. 33:133.
Bradbury, A. F. et al. (1976) Nature 260:165.
Breder, C. D. et al. (1992). J. Neurosci 12:3920.
Chang et al., (1978) Nature, 375:615.
Chesselet et al. (1987) J. Comp. Neurol. 262:125.
Childers, S. (1991) Life Sci. 48:991.
Clark, J. A. et al. (1989) J. Pharmacol. Expt. Therapeut. 251:461.
Cotecchia et al. (1988) Proc. Natl. Acad. Sci. USA 85:7159.
Cowan, A. and Murray, C. (1990) Prog. Clin. Biol. Res. 328:303.
Crea et al., (1978) Proc. Natl. Acad. Sci. U.S.A, 75:5765.
Danboldt, N. C. et al. (1990) Biochemistry 29(28):6734.
Di Chiara, G. et al. (1992) Trends Pharmacol. Sci. 13:185.
Dohlman (1987) Biochemistry 26:2657.
Dohlman, H. G. (1991) Annu. Rev. Biochem. 60:166–170; 174–s176; 653–688.
Ferruti, P. and Tanzi, M. C., (1986) Cris. Rev. Ther. Drug Carrier Syst. 2:117–136.
Fiers et al. (1978) Nature 273:113.
Frielle, T. et al. (1988) Proc. Natl. Acad. Sci. USA 85:9484.
Gabizon, A. et al., (1990) Cancer Res. 50:6371–6378
Gioannini, T. L. et al. (1989) J. Mol. Recogn. 2:44.
Goeddel et al., (1979) Nature, 281:544.
Goeddel et al., (1980) Nucleic Acids Res., 8:4057.
Gransch, C. et al. (1988) J. Biol. Chem. 263:5853.
Hausdorff, et al. (1990) FASEB J 4:2881.
Hess et al., (1968) J. Adv. Enzyme Reg. 7:149.
Heyman et al. (1988) TIPS 9:134.
Hitzeman et al., (1980) J. Biol. Chem. 255:2073.
Holland et al., (1978) Biochemistry 17:4900.
Horstman, D. A. et al. (1990) J. Biol. Chem. 265:21590.
Hsia, J. A. et al. (1984) J. Biol. Chem. 259:1086.
Hughes, J. et al. (1975) Nature 258:577.
Itakura et al., (1977) Science, 198: 1056.
Jones, (1977) Genetics 85:12.
Kanaho et al. (1984) J. Biol. Chem. 259:7378.
Kennelly, P. J. et al. (1991) J. Biol. Chem. 266:15555.
King et al. (1990) Science 250:121.
Kingsman et al., (1979) Gene 7:141.
Kobilka, B. K. et al. (1987) J. Biol. Chem. 262:7321.
Kobilka, B. K. et al. (1988) Science 240:1310.
Koob, G. F. et al. (1992) Trends Neurosci. 15:186.
Koob, G. and Bloom, F. (1992) Science 242:715.
Kozasa et al. (1988) Proc. Natl. Acad. Sci USA 85:2081.
Kruse and Patterson, eds. (1973) Tissue Culture, Academic Press.
Kyte, J., and R. F. Doolittle (1982) J. Mol. Biol. 157:105.
Law, et al. (1983) Mol. Pharmacol. 23:26.
Law, S. F. and Reisine, T. (1992) Mol. Pharmacol. 42:398.
Law, S. et al. (1991) J. Biol. Chem. 266:17885.
Law, S. F. et al. (1993) J. Biol. Chem. 268:10721.
Loh, H. H. et al., (1990) Annu. Rev. Pharmacol. Toxicol. 30:123.
Loh, H. and Smith, A. (1990) Annu. Rev. Pharmacol. 30:123.
Lomasney et al. (1990) Proc. Natl. Acad. Sci. USA 87:5094.
Lutz, R. A. et al. (1992) J. enzyme Res. 12:267.
Mansour, A. et al. (1987) J. Neurosci. 7:2445.
Marullo et al. (1988) Proc. Natl. Acad. Sci. USA 85:7551.
Messing et al., Third Cleveland Symposium on Macromolecules and Recombinant DNA, Editor A. Walton, Elsevier, Amsterdam (1981).
Nathans et al. (1986 A) Science 232:193.
Nathans et al. (1986B) Science 232:203
Nestler, E. (1993) Crit. Rev. in Neurobiol. 7:23.
Nock, B. et al. (1988) Eur. J. Pharmacol. 154:27.
Okayarea et al. (1983) Mol. Cell Biol. 3:280.
Okuma, Y. and Reisine, T. (1992) J. Biol. Chem. 267:14826.
Olson, G. A. et al. (1989) Peptides 10:1253.
Ott, S. et al. (1988) J. Biol. Chem. 263:10524.
Payette et al. (1990) FEBS Lett. 266:21.
Pert, C. G. et al. (1973) Science 179:1011.
Pert, C. B. et al. (1974) Mol. Pharmacol. 10:868.
Pfeiffer, A. et al. (1986) Science 223:774.
Puttfarcken, P. S. et al. (1988) Mol. Pharmacol. 33:520.
Ranade, V. V. (1989) J. Clin. Pharmacol. 29:685–694
Raynor, K. and Reisine, T. (1989) J. Pharmacol. Expt. Therap. 251:510.
Regan et al. (1988) Proc. Natl. Acad. Sci. USA 85:6301.
Rens-Domiano et al. (1992) Mol. Pharmacol. 42:28.
Sambrook, J. et al. (1989) Molecular Cloning: A Laboratory Manual (Cold Spring Harbor Laboratory Press, Cold Spring Harbor, N.Y.).
Seeburg (1982) DNA 1:239.
Shook, J. E. et al. (1990) Am. Rev. Respir. Dis. 142:895.
Siebwenlist et al., (1980) Cell, 20:269.
Simon, E. J. (1991) Medicinal Res. Rev. 11:357.

Soghomonian et al. (1992) *Brain Res.* 576:68.
Stinchcomb et al., (1979) *Nature,* 282:39.
Stratford-Perricaudet et al. (1992).
Strotchman and Simon (1991).
Tallarida, R. and Murray, R. (1987) *Manual of Pharamcological calculations with computer programs,* 2nd ed.
Thomsen et al. (1984) *PNAS* 81:659.
Tortella, R. et al. (1981) *Life Sci.* 10:1039.
Tschemper et al., (1980) *Gene* 10:157.
Unterwald, E. M. et al. (1991) *Brain Res.* 562:57.
Unterwald, E. M. et al. (1987) *Eur. J. Pharmacol.* 133:275.
Weiss-Wunder, L. and Chesselet, M. F. (1991) *J. Comp. Neurol.* 303:478.
Xie, G-X., et al. (1992) *Proc. Natl. Acad. Sci. USA* 89:4124.
Yamada, Y. et al. (1992) *Proc. Natl. Acad. Sci. USA* 89:251.
Yasuda, K. et al. (1992) *J. Biol Chem.* 267:20422.
Yokota, Y. et al. (1992) *EMBO J.* 11:3585.
Zukin, R. S. et al. (1988) *Proc. Natl. Acad. Sci. USA* 85:4061.
Glotzer et al., *Nature* 349, 132-8 (1991).
Okazaki et al., *EMBO J.* 11, 2447-2456 (1992).
Hochstrasser et al., *Proc Nail Acad Sci U S A* 88, 4606-10 (1991).
Chen et al., *Cell* 74, 357-369 (1993).
Finley & Chau, *Annu Rev Cell Biol* 7, 25-69 (1991).
Hershko & Ciechanover, *Annu Rev Biochem* 61, 761-807 (1992).
Hochstrasser, *Curr. Opin. Cell Biol.* 4, 1024-1031 (1992).
Jentsch, *Ann. Rev. Genet.* 26, 177-205 (1992).
Varshavsky, *Cell* 69, 725-35 (1992).
Hochstrasser & Varshavsky, *Cell* 61, 697-708 (1990).
Rose, I. A. in *Ubiquitin* (eds. Rechsteiner, M.) 135-155 (Plenum Press, New York, 1988).
Hadari et al., *J Biol Chem* 267, 719-727 (1992).
Murakami et al., *Nature* 360, 597-9 (1992).
Rechsteiner, *J. Biol. Chem.* 268, 6065-6068 (1993).
Mayer & Wilkinson, *Biochemistry,* 28, 166-72 (1989).
Jonnalagadda et al., *J. Biol. Chem.* 264, 10637-10642 (1989).
Baker et al., *J Biol Chem* 267, 23364-75 (1992).
Miller et al., 7, 698-709 (1989).
Tobias & Varshavsky, *J Biol Chem* 266, 12021-8 (1991).
Nakamura et al., *Oncogene* 7, 733-41 (1992).
Chau et al., *Science* 243, 1576-83 (1989).
Cook et al., *J Biol Chem* 267, 16467-71 (1992).
Ellison & Hochstrasser, *J Biol Chem* 266, 21150-7 (1991).
Gupta et al., *Oncogene* 8, 2307-2310 (1993).
Fischer-Vize et al., *Development* 116, 985-1000 (1992).
Ozkaynak et al., *EMBO J.* 6, 1429-1439 (1987).
Orlowski, *Biochem.* 29, 10289-10297 (1990).
Klein, *FASEB J.* 7, 821-825 (1993).
Miller et al., *Cell* 36, 51-60 (1984).
Small et al., *Mol. Cell Biol.* 7, 1638-1645 (1987).
Struhl, *Proc. Natl. Acad. Sci., U.S.A.* 82, 8419-8423 (1985).
Singer et al., *Genes Devel.* 4, 636-645 (1990).
Rose et al., *Gene* 60, 237-243 (1987).
Gietz & Sugino, *Gene* 74, 527-534 (1988).
Ausubel et al., *Current Protocols in Molecular Biology* (John Wiley and Sons, New York, 1989).
Sharp & Li, *Nucleic Acids Res.* 15, 1281-1295 (1987).
De Virgilio et al., *Eur. J. Biochem.* 212, 315-323 (1993).
Dayhoff et al., *Meth. Enzymol.* 91, 534-545 (1988).
Altschul et al., *J. Mol. Biol.* 215, 403-410 (1990).
Tobias et al., *Science* 254, 1374-7 (1991).
Gallwitz & Sures, *Proc. Natl. Acad. Sci. U.S.A.* 77, 2546-2550 (1980).
Bachmair et al., *Science* 234, 179-186 (1986).
Christianson et al., *Gene* 110, 119-122 (1992).
Dohmen et al., *Proc Nail Acad Sci U S A* 88, 7351-7355 (1991).
Deveraux et al., *J Biol Chem* 265, 6323-9 (1990).

What is claimed is:

1. An isolated and purified polynucleotide that encodes a polypeptide comprising the amino acid sequence of SEQ ID NO: 2.

2. The isolated and purified polynucleotide of claim 1, wherein said polynucleotide comprises the nucleotide base sequence from about nucleotide position 271 to about nucleotide position 3048 of SEQ ID NO: 1.

3. An expression vector comprising a polynucleotide that encodes a polypeptide comprising the amino acid sequence of SEQ ID NO: 2.

4. A recombinant host cell transfected with a polynucleotide that encodes a polypeptide comprising the amino acid sequence of SEQ ID NO: 2.

5. An isolated yeast cell containing a mutated DOA4 gene, which mutated gene encodes a DOA4 enzyme that does not catalyze the deubiquitination of proteins.

6. The cell of claim 5 wherein said cell is designated MH11D5–8a or MHY 11D5–7b.

7. A process of preparing a deubiquitinating enzyme polypeptide comprising:

transfecting a cell with the polynucleotide of claim 1 to produce a transformed host cell; and maintaining the transformed host cell under biological conditions sufficient for expression of the polypeptide.

* * * * *

SEQUENCE LISTING ( 1 ) GENERAL INFORMATION:

( i i i ) NUMBER OF SEQUENCES: 44

( 2 ) INFORMATION FOR SEQ ID NO:1:

( i ) SEQUENCE CHARACTERISTICS:
( A ) LENGTH: 3328 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: /desc ="DNA"

( i x ) FEATURE:
( A ) NAME/KEY: CDS
( B ) LOCATION: 271..3048

( x i ) SEQUENCE DESCRIPTION: SEQ ID NO:1:

```
GATATCTATA  TAAGTGCAAA  ACTATAACCA  TTATTTATTT  GCTTCCACA   TTGTTTTACT    60

TCATTTGCTT  CAATATCGTT  CATTACGTTT  AGCGAATGGC  TAAGGCCTTG  TATTAGTAAA   120

AGCCTAGAAA  AAAAAAAAAA  AAAAAAAAAA  GGATATGATG  TTATATGATA  CGTGTAGTTC   180

ATGTATTTAT  CTTCGGTAGT  ATAGGGCAGA  TTTAAGACTG  AGTGTGCACG  CTTCCAAAGT   240

TTTTTTACT   ATTTGATACA  TGCTTAAGTT  ATGGAGCAGA  ATATTATTAG  TACCATAAGG   300
```

| | | | | | |
|---|---|---|---|---|---|
| GATGAGTGTA | TTCGTCACCG | GTCGAAGTAC | CTTACGATAG | CACAACTAAC | CGCTATTGCA | 360
| GAGGCTAAAA | TTAACGAATT | CATCATAACT | GGTAAGGCAA | AAGATCAAGA | TTTGAGCAGT | 420
| CTTCTAGATA | AATGCATCGA | TATTTTATCT | ATTTACAAGA | AGAACTCGAA | AGATATCAAA | 480
| AATATTATAT | CGTGCAAAAA | TAAGGGTGCA | ATGATTAGTT | CAAATTCCGT | AATGATTATT | 540
| CAATTAAATT | ATGTTTACTA | CAAGGTAATT | CACATTATTG | TAACAACCAA | TATTCCTCAT | 600
| TTAAGTGAAT | TCGCCAAGAT | TAAATTACAT | AAGAGCACGA | GTGATGAGGG | CAACGGTAAT | 660
| AACAACAATA | ATGAATTTCA | ACTCATGAAC | ATTTACAACA | CTTTGCTGGA | AACCTTATTA | 720
| AAAGATGAAA | ACATTGCAAA | AATAAAAAGT | TTCATTAAGT | CTTCCATAAA | ACAAACAAAA | 780
| TTGAACCATG | AGCAAGAAGA | ATGTAACCTG | ATGAGAACGG | GTTCCTATAT | CACTTCCAAT | 840
| CAATTAAACT | CCCTAATAAG | TTCATCAGCA | AATTCTGCTT | CCTCCCAAAT | GGAGATACTA | 900
| CTGATAGATA | TACGATCAAG | GTTGGAATTC | AACAAGTCAC | ATATTGATAC | AAAAAATATT | 960
| ATATGCCTGG | AGCCTATTTC | TTTTAAAATG | TCATATTCAG | ATCATGATTT | GGAGAAAAAA | 1020
| TCATTAATTA | CTTCTCCTAA | TAGTGAGATT | AAAATGTTTC | AAAGTAGAAA | TCTTTTCAAG | 1080
| TTTATCATTC | TCTATACAGA | CGCAAACGAA | TACAATGTTA | AACAGCAGTC | TGTCCTGTTG | 1140
| GACATTCTGG | TGAATCATTC | CTTGAAAAA | CCAATATCCG | ATGACTTTAC | CAAAATTTTC | 1200
| ATTCTGGAAT | CTGGTTTTCC | AGGTTGGCTT | AAGTCAAATT | ATGGGAGGCA | AGTATCATCA | 1260
| TCTTTTCCAT | CAAATAACAA | TATTAAAGAT | GATAGTGTTT | ATATTAATGG | TAACACTTCT | 1320
| GGCCTAAGTT | TACAACATTT | ACCTAAGATG | TCTCCCAGTA | TAAGACATTC | AATGGACGAC | 1380
| TCTATGAAAG | AAATGCTAGT | TGCGCCTACT | CCATTAAATC | ATCTTCAACA | ACAGCAACAA | 1440
| CAGCAATCAG | ACAATGATCA | TGTGCTAAAA | AGATCTTCAA | GTTTCAAAAA | ATTATTCTCA | 1500
| AATTATACGT | CTCCTAATCC | GAAGAATTCA | AATTCAAACT | TATATTCTAT | ATCTTCGTTG | 1560
| TCCATATCTA | GTTCACCATC | GCCTTTACCT | CTACATTCGC | CTGACCCAGT | TAAGGGCAAT | 1620
| TCATTCCGAA | TCAATTATCC | GGAAACGCCA | CATCTTTGGA | AAAACAGTGA | GACAGATTTT | 1680
| ATGACAAATC | AAAGAGAACA | GTTGAATCAC | AACTCTTTTG | CTCACATAGC | TCCTATCAAC | 1740
| ACGAAGGCCA | TCACTTCTCC | ATCAAGAACT | GCCACACCGA | AGTTACAACG | CTTCCCGCAA | 1800
| ACAATTAGTA | TGAACCTTAA | TATGAACTCC | AATGGACACA | GTTCTGCCAC | CTCTACCATT | 1860
| CAACCTTCGT | GTCTATCCTT | GTCTAATAAT | GACTCTTTAG | ATCATACAGA | TGTTACACCA | 1920
| ACTTCTTCTC | ATAATTATGA | CCTTGATTTC | GCGGTTGGTT | TGGAAAATCT | AGGAAATTCG | 1980
| TGTTACATGA | ACTGTATCAT | TCAGTGTATC | TTAGGTACAC | ACGAATTAAC | CCAAATCTTT | 2040
| TTGGACGATT | CATATGCTAA | ACACATCAAT | ATTAATAGTA | AGTTGGGATC | GAAAGGTATT | 2100
| CTGGCAAAAT | ATTTTGCAAG | GTTGGTTCAT | ATGATGTATA | AGGAACAGGT | TGATGGTTCA | 2160
| AAGAAAATTT | CCATATCACC | GATAAAATTT | AAATTGGCAT | GTGGATCTGT | TAACTCATTA | 2220
| TTTAAGACTG | CATCCCAACA | GGACTGCCAA | GAGTTTTGCC | AATTCCTTCT | AGATGGTCTT | 2280
| CATGAAGACT | TGAACCAATG | CGGTTCAAAC | CCACCTTTGA | AGGAGCTTTC | TCAAGAAGCT | 2340
| GAGGCGAGAA | GAGAAAAACT | GTCTTTGCGA | ATTGCCTCGT | CAATTGAGTG | GAACGATTC | 2400
| TTGACTACTG | ATTTCAGTGT | TATTGTCGAC | TTATTTCAGG | ACAATACGC | CTCACGACTA | 2460
| AAATGTAAAG | TCTGTAGTCA | TACCTCGACA | ACATACCAAC | CTTTTACGGT | GCTGTCAATC | 2520
| CCTATTCCTA | AAAAAAATTC | CCGAAATAAT | ATTACCATTG | AAGATTGTTT | CAGAGAGTTC | 2580
| ACCAAATGTG | AGAACTTGGA | AGTGGATGAG | CAATGGTTGT | GCCCACATTG | TGAAAAAGG | 2640
| CAGCCCTCCA | CGAAACAATT | GACAATAACG | AGATTACCGA | GGAATCTGAT | AGTCCATTTA | 2700

```
AAGAGATTTG ATAATTTATT AAACAAAAAT AATGACTTCG TCATATACCC TTTTTTGTTG    2760

GACTTGACTC CATTTTGGGC CAATGATTTT GACGGGGTTT TTCCTCCAGG TGTTAATGAC    2820

GATGAACTAC CAATAAGGGG ACAAATACCA CCTTTTAAGT ATGAATTATA TGGTGTAGCA    2880

TGCCACTTTG GTACTTTGTA TGGTGGTCAT TATACAGCCT ATGTGAAAAA GGGATTAAAG    2940

AAGGGATGGC TATATTTTGA TGATACCAAA TATAAACCTG TCAAAAACAA AGCCGATGCA    3000

ATTAACTCTA ATGCATACGT TTTGTTTTAT CACCGCGTCT ACGGTGTTTG ATTCATTTGA    3060

ATAAATAACT GAAAACCGTT GTCTATACAC TTTTTTTCCC GTTCAACATG GCATATCATT    3120

ATTTCCATCT AAGGTCAAAG TAAAAACCC TAAATACAAA TGATTTATTT TAACGGTAAC     3180

AAACGAACTT TTTTTTAGAA GGTGTAAAGA TGAGATCACG CCCAGATTTT GTCTTCCTCC    3240

TGTGCATCTC TTGGATTGAT GATTTTCCTT TCTACCATAA TACGTCATGA AAGTATGTA    3300

AATATTTATA GCATTACATA TATCTTTT                                     3328
```

( 2 ) INFORMATION FOR SEQ ID NO:2:

( i ) SEQUENCE CHARACTERISTICS:
        ( A ) LENGTH: 926 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met Glu Gln Asn Ile Ile Ser Thr Ile Arg Asp Glu Cys Ile Arg His
  1               5                  10                  15

Arg Ser Lys Tyr Leu Thr Ile Ala Gln Leu Thr Ala Ile Ala Glu Ala
             20                  25                  30

Lys Ile Asn Glu Phe Ile Ile Thr Gly Lys Ala Lys Asp Gln Asp Leu
         35                  40                  45

Ser Ser Leu Leu Asp Lys Cys Ile Asp Ile Leu Ser Ile Tyr Lys Lys
     50                  55                  60

Asn Ser Lys Asp Ile Lys Asn Ile Ile Ser Cys Lys Asn Lys Gly Ala
 65                  70                  75                  80

Met Ile Ser Ser Asn Ser Val Met Ile Ile Gln Leu Asn Tyr Val Tyr
                 85                  90                  95

Tyr Lys Val Ile His Ile Ile Val Thr Thr Asn Ile Pro His Leu Ser
            100                 105                 110

Glu Phe Ala Lys Ile Lys Leu His Lys Ser Thr Ser Asp Glu Gly Asn
        115                 120                 125

Gly Asn Asn Asn Asn Asn Glu Phe Gln Leu Met Asn Ile Tyr Asn Thr
    130                 135                 140

Leu Leu Glu Thr Leu Leu Lys Asp Glu Asn Ile Ala Lys Ile Lys Ser
145                 150                 155                 160

Phe Ile Lys Ser Ser Ile Lys Gln Thr Lys Leu Asn His Glu Gln Glu
                165                 170                 175

Glu Cys Asn Leu Met Arg Thr Gly Ser Tyr Ile Thr Ser Asn Gln Leu
            180                 185                 190

Asn Ser Leu Ile Ser Ser Ser Ala Asn Ser Ala Ser Ser Gln Met Glu
        195                 200                 205

Ile Leu Leu Ile Asp Ile Arg Ser Arg Leu Glu Phe Asn Lys Ser His
    210                 215                 220

Ile Asp Thr Lys Asn Ile Ile Cys Leu Glu Pro Ile Ser Phe Lys Met
225                 230                 235                 240
```

```
Ser Tyr Ser Asp His Asp Leu Glu Lys Lys Ser Leu Ile Thr Ser Pro
            245             250             255

Asn Ser Glu Ile Lys Met Phe Gln Ser Arg Asn Leu Phe Lys Phe Ile
            260             265             270

Ile Leu Tyr Thr Asp Ala Asn Glu Tyr Asn Val Lys Gln Gln Ser Val
            275             280             285

Leu Leu Asp Ile Leu Val Asn His Ser Phe Glu Lys Pro Ile Ser Asp
    290             295             300

Asp Phe Thr Lys Ile Phe Ile Leu Glu Ser Gly Phe Pro Gly Trp Leu
305             310             315                         320

Lys Ser Asn Tyr Gly Arg Gln Val Ser Ser Ser Phe Pro Ser Asn Asn
            325             330             335

Asn Ile Lys Asp Asp Ser Val Tyr Ile Asn Gly Asn Thr Ser Gly Leu
            340             345             350

Ser Leu Gln His Leu Pro Lys Met Ser Pro Ser Ile Arg His Ser Met
        355             360             365

Asp Asp Ser Met Lys Glu Met Leu Val Ala Pro Thr Pro Leu Asn His
370             375             380

Leu Gln Gln Gln Gln Gln Gln Ser Asp Asn Asp His Val Leu Lys
385             390             395             400

Arg Ser Ser Ser Phe Lys Lys Leu Phe Ser Asn Tyr Thr Ser Pro Asn
            405             410             415

Pro Lys Asn Ser Asn Ser Asn Leu Tyr Ser Ile Ser Ser Leu Ser Ile
            420             425             430

Ser Ser Ser Pro Ser Pro Leu Pro Leu His Ser Pro Asp Pro Val Lys
            435             440             445

Gly Asn Ser Phe Arg Ile Asn Tyr Pro Glu Thr Pro His Leu Trp Lys
    450             455             460

Asn Ser Glu Thr Asp Phe Met Thr Asn Gln Arg Glu Gln Leu Asn His
465             470             475             480

Asn Ser Phe Ala His Ile Ala Pro Ile Asn Thr Lys Ala Ile Thr Ser
            485             490             495

Pro Ser Arg Thr Ala Thr Pro Lys Leu Gln Arg Phe Pro Gln Thr Ile
            500             505             510

Ser Met Asn Leu Asn Met Asn Ser Asn Gly His Ser Ser Ala Thr Ser
            515             520             525

Thr Ile Gln Pro Ser Cys Leu Ser Leu Ser Asn Asn Asp Ser Leu Asp
    530             535             540

His Thr Asp Val Thr Pro Thr Ser Ser His Asn Tyr Asp Leu Asp Phe
545             550             555             560

Ala Val Gly Leu Glu Asn Leu Gly Asn Ser Cys Tyr Met Asn Cys Ile
            565             570             575

Ile Gln Cys Ile Leu Gly Thr His Glu Leu Thr Gln Ile Phe Leu Asp
            580             585             590

Asp Ser Tyr Ala Lys His Ile Asn Ile Asn Ser Lys Leu Gly Ser Lys
            595             600             605

Gly Ile Leu Ala Lys Tyr Phe Ala Arg Leu Val His Met Met Tyr Lys
    610             615             620

Glu Gln Val Asp Gly Ser Lys Lys Ile Ser Ile Ser Pro Ile Lys Phe
625             630             635             640

Lys Leu Ala Cys Gly Ser Val Asn Ser Leu Phe Lys Thr Ala Ser Gln
            645             650             655

Gln Asp Cys Gln Glu Phe Cys Gln Phe Leu Leu Asp Gly Leu His Glu
            660             665             670
```

| | | | | | | | | | | | | | | | |
|---|---|---|---|---|---|---|---|---|---|---|---|---|---|---|---|
|Asp|Leu|Asn|Gln|Cys|Gly|Ser|Asn|Pro|Pro|Leu|Lys|Glu|Leu|Ser|Gln|
| | |675| | | |680| | |  |685| | | | | |
|Glu|Ala|Glu|Ala|Arg|Arg|Glu|Lys|Leu|Ser|Leu|Arg|Ile|Ala|Ser|Ser|
| |690| | | |695| | | |700| | | | | | |
|Ile|Glu|Trp|Glu|Arg|Phe|Leu|Thr|Thr|Asp|Phe|Ser|Val|Ile|Val|Asp|
|705| | | |710| | | |715| | | | | | |720|
|Leu|Phe|Gln|Gly|Gln|Tyr|Ala|Ser|Arg|Leu|Lys|Cys|Lys|Val|Cys|Ser|
| | | |725| | | |730| | | | |735| | | |
|His|Thr|Ser|Thr|Thr|Tyr|Gln|Pro|Phe|Thr|Val|Leu|Ser|Ile|Pro|Ile|
| | |740| | | | |745| | | | |750| | | |
|Pro|Lys|Lys|Asn|Ser|Arg|Asn|Asn|Ile|Thr|Ile|Glu|Asp|Cys|Phe|Arg|
| |755| | | | |760| | | | |765| | | | |
|Glu|Phe|Thr|Lys|Cys|Glu|Asn|Leu|Glu|Val|Asp|Glu|Gln|Trp|Leu|Cys|
| |770| | | | |775| | | |780| | | | | |
|Pro|His|Cys|Glu|Lys|Arg|Gln|Pro|Ser|Thr|Lys|Gln|Leu|Thr|Ile|Thr|
|785| | | |790| | | |795| | | | | | |800|
|Arg|Leu|Pro|Arg|Asn|Leu|Ile|Val|His|Leu|Lys|Arg|Phe|Asp|Asn|Leu|
| | | | |805| | | |810| | | | | |815| |
|Leu|Asn|Lys|Asn|Asn|Asp|Phe|Val|Ile|Tyr|Pro|Phe|Leu|Leu|Asp|Leu|
| | |820| | | | |825| | | |830| | | | |
|Thr|Pro|Phe|Trp|Ala|Asn|Asp|Phe|Asp|Gly|Val|Phe|Pro|Pro|Gly|Val|
| | |835| | | |840| | | | |845| | | | |
|Asn|Asp|Asp|Glu|Leu|Pro|Ile|Arg|Gly|Gln|Ile|Pro|Pro|Phe|Lys|Tyr|
|850| | | | |855| | | | |860| | | | | |
|Glu|Leu|Tyr|Gly|Val|Ala|Cys|His|Phe|Gly|Thr|Leu|Tyr|Gly|Gly|His|
|865| | | |870| | | | |875| | | | | |880|
|Tyr|Thr|Ala|Tyr|Val|Lys|Lys|Gly|Leu|Lys|Lys|Gly|Trp|Leu|Tyr|Phe|
| | | | |885| | | |890| | | | | |895| |
|Asp|Asp|Thr|Lys|Tyr|Lys|Pro|Val|Lys|Asn|Lys|Ala|Asp|Ala|Ile|Asn|
| | |900| | | | |905| | | |910| | | | |
|Ser|Asn|Ala|Tyr|Val|Leu|Phe|Tyr|His|Arg|Val|Tyr|Gly|Val| | |
| |915| | | | |920| | | |925| | | | | |

( 2 ) INFORMATION FOR SEQ ID NO:3:

( i ) SEQUENCE CHARACTERISTICS:
        ( A ) LENGTH: 193 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

| | | | | | | | | | | | | | | | |
|---|---|---|---|---|---|---|---|---|---|---|---|---|---|---|---|
|Ala|Val|Gly|Leu|Glu|Asn|Leu|Gly|Asn|Ser|Cys|Tyr|Met|Asn|Cys|Ile|
|1| | | |5| | | | |10| | | | |15| |
|Ile|Gln|Cys|Ile|Leu|Gly|Thr|His|Glu|Leu|Thr|Gln|Ile|Phe|Leu|Asp|
| | | |20| | | | |25| | | | |30| | |
|Asp|Ser|Tyr|Ala|Lys|His|Ile|Asn|Ile|Asn|Ser|Lys|Leu|Gly|Ser|Lys|
| | |35| | | | |40| | | | |45| | | |
|Gly|Ile|Leu|Ala|Lys|Tyr|Phe|Ala|Arg|Leu|Val|His|Met|Met|Tyr|Lys|
| |50| | | | |55| | | | |60| | | | |
|Glu|Gln|Val|Asp|Gly|Ser|Lys|Lys|Ile|Ser|Ile|Ser|Pro|Ile|Lys|Phe|
|65| | | | |70| | | | |75| | | | |80|
|Lys|Leu|Ala|Cys|Gly|Ser|Val|Asn|Ser|Leu|Phe|Lys|Thr|Ala|Ser|Gln|
| | | | |85| | | | |90| | | | |95| |

| Gln | Asp | Cys | Gln     | Glu | Phe | Cys | Gln     | Phe | Leu | Asp | Gly     | Leu | His | Glu |
|     |     |     | 100     |     |     |     | 105     |     |     |     |         | 110 |     |     |

| Asp | Leu | Asn     | Gln | Cys | Gly | Ser     | Asn | Pro | Pro | Leu | Lys     | Glu | Leu | Ser | Gln |
|     |     | 115     |     |     |     |         | 120 |     |     |     |         | 125 |     |     |     |

| Glu | Ala | Glu | Ala     | Arg | Arg | Glu     | Lys | Leu | Ser | Leu | Arg     | Ile | Ala | Ser | Ser |
|     |     |     | 130     |     |     |         | 135 |     |     |     |         | 140 |     |     |     |

| Ile | Glu | Trp | Glu | Arg | Phe     | Leu | Thr | Thr | Asp     | Phe | Ser | Val | Ile | Val | Asp |
| 145 |     |     |     |     | 150     |     |     |     | 155     |     |     |     |     |     | 160 |

| Leu | Phe | Gln | Gly     | Gln | Tyr | Ala | Ser     | Arg | Leu | Lys | Cys     | Lys | Val | Cys | Ser |
|     |     |     | 165     |     |     |     |         | 170 |     |     |         |     |     | 175 |     |

| His | Thr | Ser | Thr     | Thr | Tyr | Gln | Pro     | Phe | Thr | Val | Leu     | Ser | Ile | Pro | Ile |
|     |     |     | 180     |     |     |     |         | 185 |     |     |         |     |     | 190 |     |

Pro ( 2 ) INFORMATION FOR SEQ ID NO:4:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:4:

| Ile | Thr | Ile | Glu | Asp | Cys | Phe | Arg | Glu | Phe | Thr | Lys | Cys | Glu | Asn | Leu |
| 1   |     |     |     | 5   |     |     |     |     | 10  |     |     |     |     | 15  |     |

| Glu | Val | Asp | Glu     | Gln | Trp | Leu | Cys     | Pro | His | Cys | Glu     | Lys | Arg | Gln | Pro |
|     |     |     | 20      |     |     |     | 25      |     |     |     |         | 30  |     |     |     |

| Ser | Thr | Lys     | Gln | Leu | Thr | Ile     | Thr | Arg | Leu | Pro | Arg     | Asn | Leu | Ile | Val |
|     |     | 35      |     |     |     | 40      |     |     |     |     |         | 45  |     |     |     |

| His | Leu | Lys | Arg | Phe | Asp |
|     |     |     |     |     |     |
|     |     | 50  |     |     |     |

( 2 ) INFORMATION FOR SEQ ID NO:5:

( i ) SEQUENCE CHARACTERISTICS:
        ( A ) LENGTH: 63 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:5:

| Ala | Thr | Gly | Leu | Ser | Asn | Leu | Gly | Asn | Thr | Cys | Phe | Met | Asn | Ser | Ser |
| 1   |     |     |     | 5   |     |     |     |     | 10  |     |     |     |     | 15  |     |

| Ile | Gln | Cys | Val     | Ser | Asn | Thr | Gln     | Pro | Leu | Thr | Gln     | Tyr | Phe | Ile | Ser |
|     |     |     | 20      |     |     |     |         | 25  |     |     |         |     |     | 30  |     |

| Gly | Arg | His     | Leu | Tyr | Glu | Leu     | Asn | Arg | Thr | Asn | Pro     | Ile | Gly | Met | Lys |
|     |     | 35      |     |     |     |         | 40  |     |     |     |         | 45  |     |     |     |

| Gly | His | Met     | Ala | Lys | Cys | Tyr     | Gly | Asp | Leu | Val | Gln     | Glu | Leu | Trp |
|     |     | 50      |     |     |     |         | 55  |     |     |     |         | 60  |     |     |

( 2 ) INFORMATION FOR SEQ ID NO:6:

( i ) SEQUENCE CHARACTERISTICS:
        ( A ) LENGTH: 67 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:6:

Ser Gly Thr Gln Lys Ser Val Ala Pro Leu Lys Leu Arg Arg Thr Ile
1               5                   10                  15

Ala Lys Tyr Ala Pro Lys Phe Asp Gly Phe Gln Gln Gln Asp Ser Gln
            20                  25                  30

Glu Leu Leu Ala Phe Leu Leu Asp Gly Leu His Glu Asp Leu Asn Arg
            35                  40                  45

Val His Glu Lys Pro Tyr Val Glu Leu Lys Asp Ser Asp Gly Arg Pro
        50                  55                  60

Asp Trp Glu
65

( 2 ) INFORMATION FOR SEQ ID NO:7:

( i ) SEQUENCE CHARACTERISTICS:
        ( A ) LENGTH: 52 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

Val Ala Ala Glu Ala Trp Asp Asn His Leu Arg Arg Asn Arg Ser Ile
1               5                   10                  15

Ile Val Asp Leu Phe His Gly Gln Leu Arg Ser Gln Val Lys Cys Lys
            20                  25                  30

Thr Cys Gly His Ile Ser Val Arg Phe Asp Pro Phe Asn Phe Leu Ser
            35                  40                  45

Leu Pro Leu Pro
        50

( 2 ) INFORMATION FOR SEQ ID NO:8:

( i ) SEQUENCE CHARACTERISTICS:
        ( A ) LENGTH: 54 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:8:

Ile Asn Leu Asp Ser Cys Leu Arg Ala Phe Thr Ser Glu Glu Glu Leu
1               5                   10                  15

Gly Glu Ser Glu Met Tyr Tyr Cys Ser Lys Cys Lys Thr His Cys Leu
            20                  25                  30

Ala Thr Lys Lys Leu Asp Leu Trp Arg Leu Pro Pro Phe Leu Ile Ile
            35                  40                  45

His Leu Lys Arg Phe Gln
        50

( 2 ) INFORMATION FOR SEQ ID NO:9:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

Gly Leu Val Asn Asp Gly Asn Thr Cys Phe Met Asn Ser Val Leu Gln
1               5                   10                  15

Ser Leu ( 2 ) INFORMATION FOR SEQ ID NO:10:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

Gly Ile Asn Asn Ile Gly Asn Thr Cys Tyr Leu Asn Ser Leu Leu Gln
1               5                   10                  15

Tyr Tyr ( 2 ) INFORMATION FOR SEQ ID NO:11:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Gly Leu Gly Asn Leu Gly Asn Thr Cys Phe Met Asn Ser Ala Leu Gln
1               5                   10                  15

Cys Leu ( 2 ) INFORMATION FOR SEQ ID NO:12:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Gly Leu Ser Asn Leu Gly Asn Thr Cys Phe Met Asn Ser Ser Ile Gln
1               5                   10                  15

Cys Val ( 2 ) INFORMATION FOR SEQ ID NO:13:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Gly Leu Glu Asn Leu Gly Asn Ser Cys Tyr Met Asn Cys Ile Ile Gln
1               5                   10                  15

Cys Ile ( 2 ) INFORMATION FOR SEQ ID NO:14:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:14:

Gly Leu Lys Asn Ala Gly Ala Thr Cys Tyr Met Asn Ser Val Leu Gln
1               5                   10                  15

Gln Leu ( 2 ) INFORMATION FOR SEQ ID NO:15:

( i ) SEQUENCE CHARACTERISTICS:
  ( A ) LENGTH: 18 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:15:

Gly Ile Ile Asn Arg Ala Asn Ile Cys Phe Met Ser Ser Val Leu Gln
1               5                   10                  15

Val Leu ( 2 ) INFORMATION FOR SEQ ID NO:16:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:16:

Gly Asn Thr Cys Phe Met Asn Ser
1               5

( 2 ) INFORMATION FOR SEQ ID NO:17:

( i ) SEQUENCE CHARACTERISTICS:
  ( A ) LENGTH: 14 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:17:

Tyr Ser Leu Arg Ser Val Ile Val His Tyr Gly Thr His Asn
1               5                   10

( 2 ) INFORMATION FOR SEQ ID NO:18:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:18:

Tyr Gly His Tyr Ile Ala Phe Arg (2) INFORMATION FOR SEQ ID NO:19:

(i) SEQUENCE CHARACTERISTICS:
        (A) LENGTH: 19 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

```
Trp Trp Arg Ile Ser Asp Glu Thr Val Tyr Val Val Asp Glu Ala Glu
 1               5                  10                  15

Val Leu Ser
```

(2) INFORMATION FOR SEQ ID NO:20:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:20:

```
Thr Pro Gly Val Phe Met Leu Phe Tyr
 1               5
```

(2) INFORMATION FOR SEQ ID NO:21:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:21:

```
Tyr Ser Leu Phe Ser Val Phe Ile His Arg Gly Glu Ala Ser
 1               5                  10
```

(2) INFORMATION FOR SEQ ID NO:22:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:22:

```
Tyr Gly His Tyr Trp Ile Tyr Ile
 1               5
```

(2) INFORMATION FOR SEQ ID NO:23:

(i) SEQUENCE CHARACTERISTICS:
        (A) LENGTH: 29 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:23:

```
Asn  Arg  Asn  Gly  Ile  Trp  Arg  Lys  Tyr  Asn  Asp  Glu  Thr  Ile  Ser  Glu
1              5                        10                       15

Val  Gln  Glu  Glu  Glu  Val  Phe  Asn  Phe  Asn  Glu  Gly  Asn
               20                   25
```

( 2 ) INFORMATION FOR SEQ ID NO:24:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
Thr  Ala  Thr  Pro  Tyr  Phe  Leu  Val  Tyr
1                   5
```

( 2 ) INFORMATION FOR SEQ ID NO:25:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Tyr  Asp  Leu  Ile  Ala  Val  Ser  Asn  His  Tyr  Gly  Ala  Met  Gly
1                   5                             10
```

( 2 ) INFORMATION FOR SEQ ID NO:26:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

```
Val  Gly  His  Tyr  Thr  Ala  Tyr  Ala
1                   5
```

( 2 ) INFORMATION FOR SEQ ID NO:27:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

```
Lys  Asn  Arg  Leu  Asn  Gly  Lys
1                   5
```

( 2 ) INFORMATION FOR SEQ ID NO:28:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

Trp Tyr Tyr Phe Asp Asp Ser Ser Val Ser Leu Ala Ser Glu Asp Gln
1               5                   1 0                  1 5

Ile Val ( 2 ) INFORMATION FOR SEQ ID NO:29:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:29:

Thr Lys Ala Ala Tyr Val Leu Phe Tyr
1               5

( 2 ) INFORMATION FOR SEQ ID NO:30:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:30:

Tyr Asn Leu Tyr Ala Ile Ser Cys His Ser Gly Ile Leu Ser
1               5                   1 0

( 2 ) INFORMATION FOR SEQ ID NO:31:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:31:

Gly Gly His Tyr Ile Thr Tyr Ala
1               5

( 2 ) INFORMATION FOR SEQ ID NO:32:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:32:

Trp Tyr Cys Tyr Asn Asp Ser Ser Cys Glu Glu Leu His Pro Asp Glu
1               5                   1 0                  1 5

Ile Asp ( 2 ) INFORMATION FOR SEQ ID NO:33:

( i ) SEQUENCE CHARACTERISTICS:
      ( A ) LENGTH: 9 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:33:

Thr Asp Ser Ala Tyr Ile Leu Phe Tyr
1               5

(2) INFORMATION FOR SEQ ID NO:34:

(i) SEQUENCE CHARACTERISTICS:
(A) LENGTH: 14 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:34:

Tyr Glu Leu Tyr Gly Val Ala Cys His Phe Gly Thr Leu Tyr
1               5                   10

(2) INFORMATION FOR SEQ ID NO:35:

(i) SEQUENCE CHARACTERISTICS:
(A) LENGTH: 8 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:35:

Gly Gly His Tyr Thr Ala Tyr Val
1               5

(2) INFORMATION FOR SEQ ID NO:36:

(i) SEQUENCE CHARACTERISTICS:
(A) LENGTH: 24 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:36:

Gly Leu Lys Lys Gly Trp Leu Tyr Phe Asp Asp Thr Lys Tyr Lys Pro
1               5                   10                  15

Val Lys Asn Lys Ala Asp Ala Ile
            20

(2) INFORMATION FOR SEQ ID NO:37:

(i) SEQUENCE CHARACTERISTICS:
(A) LENGTH: 9 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:37:

Asn Ser Asn Ala Tyr Val Leu Phe Tyr
1               5

(2) INFORMATION FOR SEQ ID NO:38:

( i ) SEQUENCE CHARACTERISTICS:
 ( A ) LENGTH: 14 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:38:

Tyr Glu Leu Thr Gly Ile Val Val His Ser Gly Gln Ala Ser
1               5                   10

( 2 ) INFORMATION FOR SEQ ID NO:39:

( i ) SEQUENCE CHARACTERISTICS:
 ( A ) LENGTH: 54 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:39:

Gly Gly His Tyr Phe Ser Tyr Ile Leu Ser Lys Asn Pro Ala Asn Gly
1               5                   10                  15

Lys Cys Gln Trp Tyr Lys Phe Asp Asp Gly Glu Val Thr Glu Cys Lys
                20                  25                  30

Met His Glu Asp Glu Glu Met Lys Ala Glu Cys Phe Gly Gly Glu Asn
            35                  40                  45

Ala Tyr Met Leu Phe Tyr
        50

( 2 ) INFORMATION FOR SEQ ID NO:40:

( i ) SEQUENCE CHARACTERISTICS:
 ( A ) LENGTH: 24 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:40:

Tyr Lys Leu Thr Gly Val Ile Tyr His His Gly Val Ser Ser Asp Gly
1               5                   10                  15

Gly His Tyr Thr Ala Asp Val Tyr
                20

( 2 ) INFORMATION FOR SEQ ID NO:41:

( i ) SEQUENCE CHARACTERISTICS:
 ( A ) LENGTH: 5 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:41:

His Ser Glu His Asn
1               5

( 2 ) INFORMATION FOR SEQ ID NO:42:

( i ) SEQUENCE CHARACTERISTICS:
 ( A ) LENGTH: 35 amino acids
 ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:42:

Trp Tyr Arg Ile Asp Asp Val Asn Ile Thr Glu Leu Glu Asp Asp Asp
1               5                   10                  15

Val Leu Lys Gly Gly Glu Glu Ala Ser Asp Ser Arg Thr Ala Tyr Ile
            20                  25                  30

Leu Met Tyr
        35

(2) INFORMATION FOR SEQ ID NO:43:

(i) SEQUENCE CHARACTERISTICS:
    (A) LENGTH: 4 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:43:

Gly Gly His Tyr
1

(2) INFORMATION FOR SEQ ID NO:44:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:44:

Ala Tyr His Leu Phe Tyr
1               5